(12) United States Patent
Schüttrumpf et al.

(10) Patent No.: US 10,000,748 B2
(45) Date of Patent: Jun. 19, 2018

(54) FACTOR IX VARIANTS WITH CLOTTING ACTIVITY IN ABSENCE OF THEIR COFACTOR AND/OR WITH INCREASED F.IX CLOTTING ACTIVITY AND THEIR USE FOR TREATING BLEEDING DISORDERS

(71) Applicant: DRK-BLUTSPENDEDIENST BADEN-WÜRTTEMBERG-HESSEN GGMBH, Frankfurt am Main (DE)

(72) Inventors: Jörg Schüttrumpf, Frankfurt (DE); Patricia Quade-Lyssy, Mainz-Kastel (DE); Peter Milanov, Frankfurt (DE); Erhard Seifried, Frankfurt am Main (DE)

(73) Assignee: DRK-BLUTSPENDEDIENST BADEN-WÜRTTEMBERG-HESSEN GGMBH, Frankfurt am Main (DE)

( * ) Notice: Subject to any disclaimer, the term of this patent is extended or adjusted under 35 U.S.C. 154(b) by 0 days. days.

(21) Appl. No.: 15/103,183

(22) PCT Filed: Dec. 3, 2014

(86) PCT No.: PCT/EP2014/076435
§ 371 (c)(1),
(2) Date: Jun. 9, 2016

(87) PCT Pub. No.: WO2015/086406
PCT Pub. Date: Jun. 18, 2015

(65) Prior Publication Data
US 2016/0304851 A1  Oct. 20, 2016

(30) Foreign Application Priority Data
Dec. 9, 2013 (EP) .................................. 13196284

(51) Int. Cl.
| | |
|---|---|
| *A61K 31/711* | (2006.01) |
| *C07H 21/04* | (2006.01) |
| *C12N 9/64* | (2006.01) |
| *C07K 14/745* | (2006.01) |
| *A61K 38/48* | (2006.01) |
| *C12Q 1/56* | (2006.01) |
| *A61K 38/00* | (2006.01) |

(52) U.S. Cl.
CPC .......... *C12N 9/644* (2013.01); *A61K 38/4846* (2013.01); *C07K 14/745* (2013.01); *C12Q 1/56* (2013.01); *C12Y 304/21022* (2013.01); *A61K 38/00* (2013.01); *G01N 2333/9645* (2013.01); *G01N 2500/04* (2013.01); *G01N 2500/20* (2013.01)

(58) Field of Classification Search
CPC .. A61K 38/36; A61K 38/4846; C07K 14/745; C12N 9/644; C12Y 304/21022
See application file for complete search history.

(56) References Cited

U.S. PATENT DOCUMENTS 8,778,870 B2 * 7/2014 Madison ................ C12N 9/644
514/1.1

FOREIGN PATENT DOCUMENTS

| WO | WO 2007/149406 A2 | 12/2007 |
|---|---|---|
| WO | WO 2010/012451 A1 | 2/2010 |

OTHER PUBLICATIONS

Quade-Lyssy et al. Next generation of FIX muteins with FVIII-independent activity for alternative treatment of hemophilia A. Journal of Thrombosis and Haemostasis. Nov. 2014, vol. 12, No. 11, pp. 1861-1873.*
Gui, T. et al., "Abnormal hemostasis in knock-in mouse carrying a variant of factor IX with impaired binding to collagen type IV," *Journal of Thrombosis and Haemostasis*, 2009, 7:1843-1851.
Kao, Chung-Yang et al., "Incorporation of the factor IX Padua mutation into FIX-Triple improves clotting activity in vitro and in vivo," *Thromb Haemost*, 2013, 110:244-256.
Lin, C.N. et al., "Generation of a novel factor IX with augmented clotting activities in vitro and in vivo," *Journal of Thrombosis and Haemostasis*, 2010, 8:1773-1783.
Milanov, Peter et al., "Engineered factor IX variants bypass FVIII and correct hemophilia A phenotype in mice," *Blood*, Jan. 12, 2012, 119(2):602-611.
Orlova, N.A. et al., "Coagulation Factor IX for Hemophilia B Therapy," *Acta Naturae*, 2012, 4(2):62-73.
Quade-Lyssy, P. et al., "Oral gene therapy for hemophilia B using chitosan-formulated FIX mutants," *Journal of Thrombosis and Haemostasis*, 2014, 12:932-942.
Schüttrumpf, Jörg et al., "Factor IX variants improve gene therapy efficacy for hemophilia B," *Blood*, Mar. 15, 2005, 105(6):2316-2323.

* cited by examiner

*Primary Examiner* — Jeffrey E. Russel
(74) *Attorney, Agent, or Firm* — Saliwanchik, Lloyd & Eisenschenk

(57) ABSTRACT

The present invention relates to variants of factor IX (F.IX) or activated factor IX (F.IXa), wherein the variant is characterized in that it has clotting activity in absence of its cofactor. The present invention furthermore relates to variants of factor IX (F.IX) or activated factor IX (F.IXa), wherein the variant is characterized in that it has increased F.IX clotting activity compared to wildtype. The present invention furthermore relates to the use of these variants for the treatment and/or prophylaxis of bleeding disorders, in particular hemophilia A and/or hemophilia B or hemophilia caused or complicated by inhibitory antibodies to F.VIII. The present invention also relates to further variants of factor IX (F.IX) which have desired properties and can, thus be tailored for respective specific therapeutic applications.

7 Claims, 38 Drawing Sheets

FIG. 7A

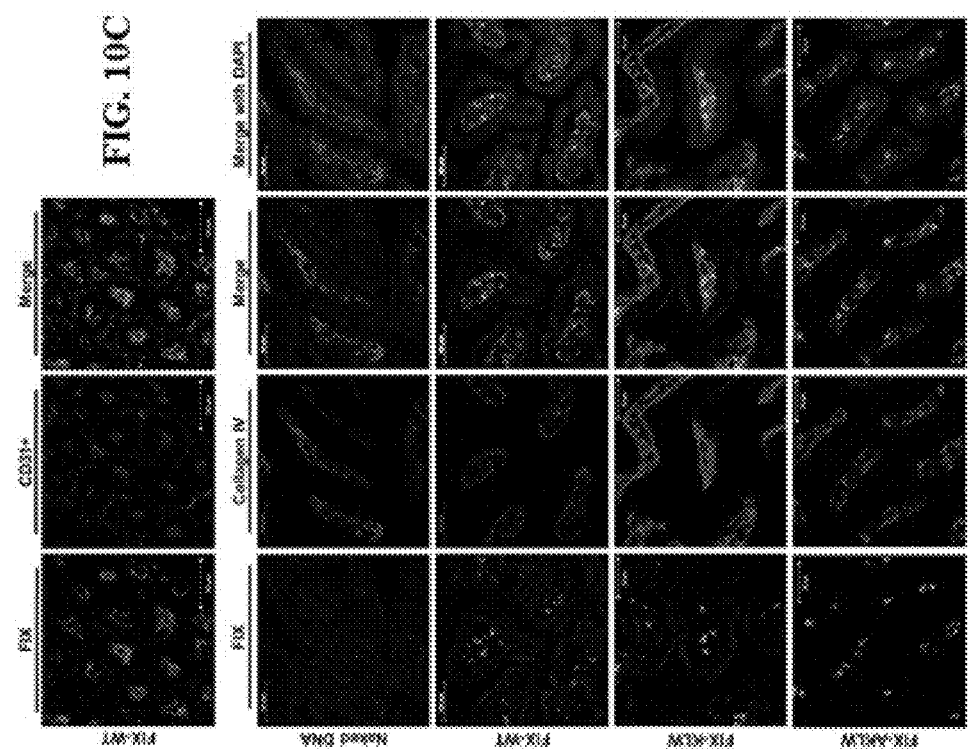
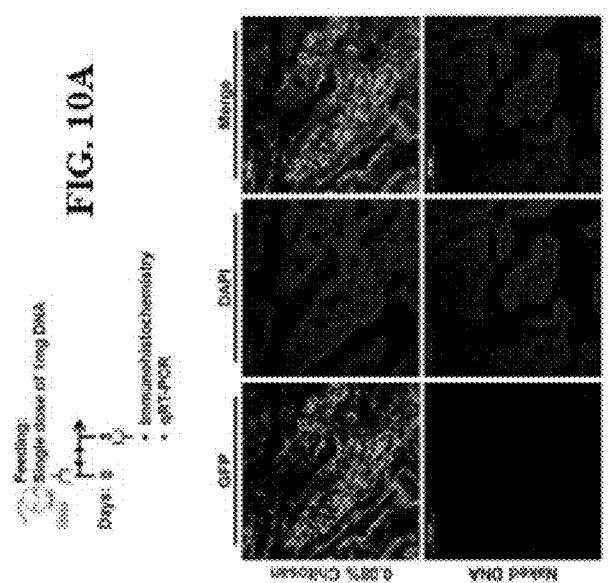
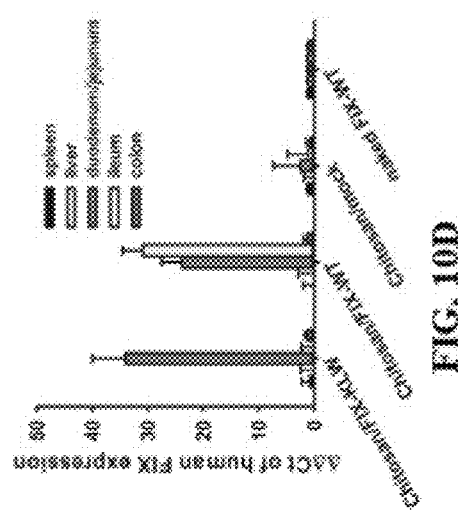
FIG. 10A  FIG. 10B  FIG. 10C  FIG. 10D

FACTOR IX VARIANTS WITH CLOTTING ACTIVITY IN ABSENCE OF THEIR COFACTOR AND/OR WITH INCREASED F.IX CLOTTING ACTIVITY AND THEIR USE FOR TREATING BLEEDING DISORDERS

CROSS REFERENCE TO A RELATED APPLICATION

This application is a National Stage Application of International Application Number PCT/EP2014/076435, filed Dec. 3, 2014; which claims priority to European Application No. 13196284.7, filed Dec. 9, 2013.

The Sequence Listing for this application is labeled "SeqList-08Jun16.txt", which was created on Jun. 8, 2016, and is 7 KB. The entire content is incorporated herein by reference in its entirety.

The present invention relates to variants of factor IX (F.IX) or activated factor IX (F.IXa), wherein the variant is characterized in that it has clotting activity in absence of its cofactor. The present invention furthermore relates to variants of factor IX (F.IX) or activated factor IX (F.IXa), wherein the variant is characterized in that it has increased F.IX clotting activity compared to wildtype. The present invention furthermore relates to the use of these variants for the treatment and/or prophylaxis of bleeding disorders, in particular hemophilia A and/or hemophilia B or hemophilia caused or complicated by inhibitory antibodies to F.VIII. The present invention also relates to further variants of factor IX (F.IX) which have desired properties and can, thus be tailored for respective specific therapeutic applications.

BACKGROUND OF THE INVENTION

Coagulation Factor IX

The blood coagulation factor IX (F.IX) plays a central role in the coagulation cascade. F.IX is a trypsin-like vitamin K-dependent serine protease that circulates in the plasma as a single chain inactive zymogen (DiScipio et al., 1977; Davie et al., 1991). Factor IX is activated by either factor XIa or by factor VIIa-tissue factor in a $Ca^{2+}$ dependent manner. The activation requires cleavage of two peptide bonds by either the activated factor VII (F.VIIa)-tissue factor complex or activated factor XI (F.XIa) (Fujikawa et al., 1974; Lindquist et al., 1978) to remove a 35-residue activation peptide.

F.IX is a multi-domain protein. An N-terminal γ-carboxy glutamic acid (GLA) domain is followed by two epidermal growth factor-like (EGF) repeats, the activation peptide (AP) and a C-terminal serine protease domain with a trypsin-like active site (DiScipio et al., 1978). This domain structure defines the serine protease family of clotting factors (Furie and Furie, 1988), including also factor II (F.II), factor VII (F.VII), factor X (F.X), factor XI (F.XI), factor XII (F.XII), and protein C (PC). Within this family, F.IXa has unique proteolytic properties. Complex formation of F.IXa with F.VIIIa on a phospholipid surface increases reactivity against the natural substrate F.X $10^6$-fold (Duffy and Lollar, 1992), while virtually no cleavage of peptides with corresponding F.X sequences was observed (McRae et al., 1981).

Freedman et al. (1996) proposed that the membrane binding site of factor IX resides in amino acid residues 1-11. In particular leucine 6, phenylalanine 9 and valine 10 were identified to form a hydrophobic site on the exterior of the FIX protein which buries inside the lipid bilayer.

Chang et al. (2002) describe that residues 102-108 in the EGF2-like domain of F.IX are important for proper binding to F.X. Wilkinson et al. obtained similar results for residues 88-109 (but not Arg94) and proposed their importance for assembly of the F.X activating complex on phospholipid vesicles or platelets (Wilkinson et al., 2002-a, Wilkinson et al., 2002-b).

Activated factor IX (F.IXa) then activates factor X (F.X) in a reaction that is dependent on the presence of calcium ions, a membrane surface (phospholipid), and a nonenzymatic protein cofactor, activated factor VIII (F.VIIIa) (Davie et al., 1991).

The importance of F.IXa in hemostasis is reflected by the occurrence of the bleeding disorder hemophilia B in individuals carrying mutations in the F.IX gene (Gianelli et al., 1998). F.IXa displays only very little proteolytic activity against natural or synthetic substrates in the absence of its cofactor F.VIIIa. Binding of F.VIIIa results in a $10^6$-fold increase in proteolytic activity for F.X, whereas the activity with peptidic substrates remains less affected (Duffy and Lollar, 1992; McRae et al., 1981). The latter substrate-dependent activity of F.IXa modulation is similarly observed for the related coagulation enzymes activated PC (co-factor Protein S), F.Xa (co-factor Factor Va), F.VIIa (cofactor tissue factor), and FIIa (co-factor thrombomodulin), which in the presence of their cofactors, achieve a significant activity or specificity change with their natural substrates. (Mann et al. 2003). All coagulation serine proteases share extensive structural and functional homology.

Furthermore, the coagulation factors IXa (F.IXa) and Xa (F.Xa) both cleave natural substrates effectively only with a cofactor at a phospholipid surface. Hopfner et al. (1997) investigated variants of truncated F.IXa (rf9a) and F.Xa (rf10a) in *E. coli* to identify determinants of the difference in the amidolytic activity of F.IXa which is $10^4$-fold lower than that of F.Xa. Based on the crystal structures of F.IXa and F.Xa four characteristic active site components (namely Glu219, the 148-loop, Ile213, the 99-loop, based on chymotrypsin numbering) were subsequently exchanged between rf9a and rf10a. Furthermore, combining all four mutations essentially introduced F.Xa properties into rf9a, i.e. the amidolytic activity was increased 130-fold with F.Xa substrate selectivity.

Enzymatically, F.IXa is characterized by its very low amidolytic activity that is not improved in the presence of cofactor, factor VIIIa (F.VIIIa), distinguishing F.IXa from all other coagulation factors. Activation of the F.IXa-F.VIIIa complex requires its macromolecular substrate, factor X (F.X). The 99-loop positioned near the active site partly accounts for the poor activity of F.IXa because it adopts a conformation that interferes with canonical substrate binding in the subsites S2-S4. Sichler et al. (2003) disclose that residues Lys-98 and Tyr-99 (chymotrypsin numbering) are critically linked to the amidolytic properties of F.IXa. Exchange of Tyr-99 with smaller residues resulted not only in an overall decreased activity but also in impaired binding in S1. Replacement of Lys-98 with smaller and uncharged residues increased activity. Simultaneous mutagenesis of Lys-98, Tyr-177, and Tyr-94 (rf9-Y94F/K98T/Y177T, chymotrypsin numbering)) produced an enzyme with 7000-fold increased activity and altered specificity towards factor Xa. Sichler et al. (2003) concluded, that these residues account for the low factor IXa activity. Sichler et al. (2003) concluded, that this triple mutant rf9-Y94F/K98T/Y177T (chymotrypsin numbering) probably mimics the conformational changes that are physiologically induced by cofactor and substrate binding.

WO 2010/012451 discloses Factor IX variants with clotting activity in absence of their cofactor and their use for treating bleeding disorders. In WO 2010/012451, the inventors demonstrated that in particular the engineered Factor IX variantITV, containing the mutations V181I, K265T and I383V, is able to bypass factor VIII and correct hemophilic phenotype of F.VIII-knockout mice in the presence of neutralizing antibodies (Milanov et al., 2012).

Hemophilia

The best-known coagulation factor disorders are the hemophilias. Hemophilia is the name of a family of hereditary genetic disorders that impair the body's ability to control blood clotting, or coagulation. Haemophilia A, the most common form, is caused by a mutation of the factor VIII (F.VIII) gene, leading to a deficiency in F.VIII. The inheritance is X-linked recessive; hence, males are affected while females are carriers or very rarely display a mild phenotype. 1 in 5,000 males are affected. Hemophilia B, also known as factor IX (F.IX) deficiency, is the second most common type of hemophilia, but hemophilia B is far less common than hemophilia A.

These genetic deficiencies may lower blood plasma clotting factor levels of coagulation factors needed for a normal clotting process. When a blood vessel is injured, a temporary scab does form, but the missing coagulation factors prevent fibrin formation which is necessary to maintain the blood clot. Thus a haemophiliac does not bleed more intensely than a normal person, but for a much longer amount of time. In severe haemophiliacs even a minor injury could result in blood loss lasting days, weeks, or not ever healing completely. The critical risk here is with normally small bleeds which due to missing F.VIII take long times to heal. In areas such as the brain or inside joints this can be fatal or life debilitating. The bleeding with external injury is normal, but incidence of late re-bleeding and internal bleeding is increased, especially into muscles, joints, or bleeding into closed spaces. Major complications include hemarthrosis, hemorrhage, gastrointestinal bleeding, and menorrhagia.

Though there is no cure for haemophilia, it can be controlled with regular infusions of the deficient clotting factor, i.e. F.VIII in haemophilia A or F.IX in haemophilia B.

In western countries, common standards of care for hemophilia fall into one of two categories: (i) prophylaxis or (ii) on-demand. Prophylaxis involves the infusion of coagulation factor on a regular schedule in order to keep clotting levels sufficiently high to prevent spontaneous bleeding episodes. On-demand treatment involves treating bleeding episodes once they arise.

However, some haemophiliacs develop antibodies (inhibitors) against the replacement factors given to them, so the amount of the factor has to be increased or non-human replacement products must be given, such as porcine F.VIII or modified variants thereof, see e.g. WO 01/68109 A1 (Emory University).

If a patient becomes refractory to replacement coagulation factor as a result of circulating inhibitors, this may be overcome with recombinant human factor VII (Novo-Seven®), see also EP 1 282 438 B1 and EP 1 282 439 B1 (Novo Nordisk). A limitation of this approach so far is the short half life of factor VIIa (2 to 3 hours) compared to factor VIII (10 to 14 hours) or factor IX (18 to 30 hours), respectively and depending on the preparation, which makes prophylactic therapy with factor VIIa difficult. Further, the risks of using an already activated protease, like factor VIIa, over prolonged time intervals might carry risks, including thrombotic risks, risks through constant activation of the vascular endothelium and vessel damage, risk of pro-coagulant signalling which could promote tumor growth or metastasis, etc.

WO 02/40544 A2 discloses mutant human factor IX comprising mutations in the heparin binding domain, which decrease the affinity of the mutant human F.IX for heparin compared to wild type F.IX, and their use in the therapeutic intervention of hemophilia B.

Gene Therapy

Hemophilia is ideal for a gene therapeutic approach since the required coagulation is circulating in the blood stream and may therefore be expressed basically everywhere in the body. Further, studies with prophylactic treatment of patients with a severe form of the disease have demonstrated that a minimal elevation of circulating coagulation factor above 1% can already improve the clinical outcome and avoid the majority of lesions caused by the disease, i.e. joint destruction. Several gene therapy approaches have been developed, but testing is still in the early clinical stages. The most promising approaches are currently for the treatment of hemophilia B with adeno-associated viral vectors (AAV).

Intramuscular injection AAV to skeletal muscle of humans with hemophilia B is safe, but higher doses are required to achieve therapeutic factor IX levels. However, dose escalation is not possible in this approach, since the risk of the formation of inhibitory antibodies depends on the amount of F.IX antigen expressed in the muscle per injection site. Estimation in a hemophilia B dog model led to the conclusion, that more than 400 intramuscular injections would be necessary to obtain F.IX expression levels of around 1% in humans (Arruda et al., 2004). This procedure, therefore, is not applicable to humans. The efficacy of this approach is hampered by the retention of F.IX in muscle extracellular spaces and by the limiting capacity of muscle to synthesize fully active F.IX at high expression rates. To overcome these limitations, Schuettrumpf et al. (2005) constructed AAV vectors encoding F.IX variants for muscle- or liver-directed expression in hemophilia B mice. Circulating F.IX levels following intramuscular injection of AAV-F.IX-K5A/V10K (F.IX numbering), a variant with low-affinity to extracellular matrix, were 2-5 fold higher compared with wild-type (WT) F.IX, while the protein-specific activities remained similar. Expression of F.IX-R338A generated a protein with 2- or 6-fold higher specific activity than F.IX-WT following vector delivery to skeletal muscle or liver, respectively. F.IX-WT and variant forms provide effective hemostasis in vivo upon challenge by tail-clipping assay. Importantly, intramuscular injection of AAV-F.IX variants did not trigger antibody formation to F.IX in mice tolerant to F.IX-WT. Besides of the mentioned R338A variant, first described by Chang et al. (1998), another variant, V86A, with higher specific F.IX activity has been described (Chang et al. 2002).

The application of gene therapy strategies for hemophilia A in comparison to hemophilia B is further complicated by the higher immunogenicity and the bigger size of the F.VIII compared to F.IX.

Thus, there is a need in the art for providing further improved means and methods for the treatment and/or prophylaxis of bleeding disorders, in particular hemophilia A and/or B.

Thus, the present invention aims to further improve the methods and means for the treatment and/or prophylaxis of bleeding disorders as present in the prior art and it is, thus, an objective of the present invention to provide further improved methods and means which allow for an effective, specific and targeted treatment and/or prophylaxis of bleeding disorders, in particular hemophilia A and/or B.

Variant Proteins of Factor IX with Clotting Activity in Absence of their Cofactor According to the present invention this object is solved by providing a variant of factor IX (F.IX) or activated factor IX (F.IXa), wherein the variant of F.IX is characterized in that it has clotting activity in absence of its cofactor, wherein the cofactor is factor VIII (F.VIII) or activated factor VIII (F.VIIIa).

The term "variants" as used herein preferably refers to amino acid substitution, addition (insertion) or deletion variants or derivatives of the naturally occurring protein. Variants comprise furthermore an amino acid sequence comprising modified amino acid(s), unnatural amino acid(s) or peptidomimetic(s) or further compounds which can mimic a peptide backbone/structure. Variants can also comprise the substitution or coupling with parts of other molecules or coupling with other molecules.

Amino acid substitutions comprise conservative as well as non conservative replacement by other amino acids or by isosteres (modified amino acids that bear close structural and spatial similarity to protein amino acids), amino acid additions or isostere additions.

Conservative amino acid substitutions typically relate to substitutions among amino acids of the same class. These classes include, for example,
- amino acids having uncharged polar side chains, such as asparagine, glutamine, serine, threonine and tyrosine;
- amino acids having basic side chains, such as lysine, arginine, and histidine;
- amino acids having acidic side chains, such as aspartic acid and glutamic acid; and
- amino acids having nonpolar side chains, such as glycine, alanine, valine, leucine, isoleucine, proline, phenylalanine, methionine, tryptophan, and cysteine.

Factor IX (F.IX) within this patent application refers to the human F.IX protein and cDNA described by Kurachi and Davie, 1982.

Refseq NM_000133 for mRNA/cDNA (SEQ ID NO. 1), and

Refseq NP_000124 for protein sequence (SEQ ID NO. 2).

The amino acid sequence of SEQ ID NO. 2 contains the signal peptide and the pro-peptide of F.IX. The actual numbering starts at −46(Met); +1 is Tyr.

There are several naturally occurring polymorphisms in the gene as well as the amino acid sequence of F.IX. A list from the Hemophilia B Mutation Database, King's College London (see www.kcl.ac.uk/ip/petergreen/haemBdatabase.html) is shown below. For example, the most frequent polymorphism is at position 147 where threonine can be found in 67% and alanine in 33% of the population. Interestingly, the less frequent alanine is present in the only available recombinant F.IX therapeutic.

| Name | Nuc No | Base Change | AA_Change | Frequency |
|---|---|---|---|---|
| | −1186 | C→T | | 52% |
| | −793 | G→A | | 44% |
| MseI | −698 | C→T | | 44% |
| BamHI (i) | −561 | T→G | | 6% |
| | 25 | A→G | | Reported once |
| | 37 | G→A | −44, R→H | Reported once |
| | 48 | A→T | −40, I→F | Reported once |
| | 181 | C→A | | rare |
| | 192 | A→G | | 19% |

-continued

| Name | Nuc No | Base Change | AA_Change | Frequency |
|---|---|---|---|---|
| | 353 | C→T | | rare |
| | 709 | A→G | | rare |
| | 1778 | C→T | | 3/10 |
| | 2627 | T→C | | 6/10 |
| | 3747 | C→A | | 6/10 |
| | 3756 | T→C | | 6/10 |
| TaqI (iii) | 3797 | C→T | | 6/10 |
| | 3905 | A→T | | 6/10 |
| DdeI | 5505 | −50 | | 76% |
| | 6550 | G→C | | Reported once |
| | 6575 | C→G | | polymorphic in Brazil |
| Pointe-a-Pitre (Guadeloupe) | 6596 | G→T | | Reported once |
| XmnI | 7076 | G→ | | 71% |
| TaqI (ii) | 9731 | ? | | Reported once |
| | 10512 | A→G | | Reported 5 times |
| TaqI (i) | 11111 | T→ | | 65% |
| | 13275 | C→T | | 1/10 |
| MspI | 15625 | A→G | | 78% |
| | 17397 | T→G | | 1/10 |
| | 20002 | C→A | | 4/10 |
| MnlI (Malmo) | 20421 | G→A | 147, A→T | 33% |
| | 20512 | T→C | 178, F→L | Reported once |
| | 27731 | C→G | | 5/10 |
| | 28364 | T→C | | rare |
| | 29335 | G→A | | 1/10 |
| | 29497 | G→T | | 1/10 |
| | 29509 | T→C | | rare |
| | 29532 | C→T | | 4/10 |
| | 29648 | G→A | | 4/10 |
| | 29650 | A→G | | rare |
| | 30134 | T→C | 227, V→V | Reported 7 times |
| | 30802 | +A | | Reported 4 times |
| | 30890 | C→T | 257, H→Y | Reported 3 times |
| | 31012 | C→T | 297, N→N | Reported once |
| | 31093 | G→A | 324, Q→Q | Reported once |
| | 31103 | G→A | 328, V→I | Reported once |
| | 32770 | T→C | | 19% |
| | 32847 | T→C | | "c" allele frequent; "t" allele seen 4 times |

Activated factor IX (F.IXa) within this patent application refers to the activated F.IX molecule through cleavage of the 35 amino acid activation peptide as described above.

Since both coagulation factors F.IX and F.VIII always have to be activated before they can exhibit their function both F.IX/F.IXa or F.VIII/F.VIIIa can be used as synonyms.

For the numbering of the amino acid residues the F.IX numbering system is used (according to Kurachi and Davie, 1982, except when indicated otherwise). By some authors in the art, the chymotrypsinogen numbering is used for the description of certain amino acids in homology to the serine protease chymotrypsin. For the present invention the chymotrypsin numbering is only used when explicitly indicated herein.

The "clotting activity" or "functional activity" of F.IX can also be referred to as specific F.IX activity, which is usually measured in Unit/milligram (U/mg). Since one Unit (1 U) of F.IX is referred to as the amount of F.IX in 1 milliliter (ml) of normal human plasma, which corresponds to 5000 ng F.IX, the usual specific activity is around 200 U/mg. Since the specific activity of F.IX is defined as protease activity in the plasma in presence of F.VIII, there is no definition in use in the art for (clotting) activity in absence of cofactor F.VIII. Therefore, the clotting activity in absence of F.VIII, also called "F.VIII-like activity", is expressed herein as percentage of the activity, which an equal amount of wild type F.IX would exhibit in the presence of F.VIII.

Thus, a F.IX variant has "clotting activity" in absence of its cofactor, when it corrects the blood coagulation deficiency caused by the absence of clotting F.VIII in the blood, which in case of a disease can either be due to absence of the F.VIII protein, presence of a defective F.VIII protein, or inhibition of the F.VIII protein, for example by inhibitory antibodies.

The assay system used in the present invention for determining "clotting activity" or "functional activity" of the variants of a vitamin K-dependent serine protease of the coagulation cascade, preferably of F.IX variants, is an one stage assay based on the aPTT. The activated partial thromboplastin time (aPTT or APTT) is a performance indicator measuring the efficacy of both the "intrinsic" (now referred to as the contact activation pathway) and the common coagulation pathways. Apart from detecting abnormalities in blood clotting, it is also used to monitor the treatment effects with heparin, a major anticoagulant. For the determination of the F.VIII or F.IX activity levels in a sample, the test is performed by spiking the sample into F.VIII or F.IX deficient plasma for measurement of the F.VIII or F.IX activity, respectively. This test is referred to as F.VIII or F.IX one stage assay. Now, F.VIII independent activity of a F.IX variant can be determined by one stage assay and using F.VIII deficient plasma.

Briefly, blood is collected with oxalate or citrate which arrest coagulation by binding calcium. The plasma is separated from the corpuscular parts of the blood by centrifugation. In the case of recombinantly expressed and purified proteins, the protein is diluted in imidazole buffer.

The sample is mixed and added to standardized factor (VIII or IX) deficient plasma. In order to activate the intrinsic pathway, phospholipid, an activator (such as silica, celite, kaolin, ellagic acid), and calcium (to reverse the anticoagulant effect of the oxalate) are mixed into the plasma sample. The time is measured until a thrombus (clot) forms. The test is termed "partial" due to the absence of tissue factor from the reaction mixture (see Langdell et al., 1953).

Preferably, the variants of factor IX according to the invention have clinical relevant clotting activity (or clotting activity with clinical relevance), i.e. clotting activity which makes the variants suitable for clinical applications, as disclosed herein below.

A preferred clotting activity with clinical relevance is 1% or more clotting activity of the variant in absence of cofactor F.VIII, wherein 100% refers to the activity of wild type F.IX in presence of cofactor F.VIII or F.VIIIa.

Around 1% sustained factor VIII or factor IX levels are enough in prophylactic treatment regimens to prevent major bleeding complications in severe hemophilia patients. To reach a 1% level in a severe hemophilia A patient with a factor IX variant which has "1% F.VIII-like" activity in absence of F.VIII, F.IX variant levels of 100% of normal (around 5000 ng/ml) additional to the already physiologically present F.IX would be necessary. Such a treatment seems feasible and therefore the clinically relevant "factor VIII-like" activity is estimated at 1%.

In an embodiment the variant factor IX of the invention comprises a modification of the 99-loop, preferably by amino acid substitutions, insertions and/or deletions. A modification of the 99-loop can also be achieved by affecting the loop structure by amino acid substitutions, insertions and/or deletions of adjacent amino acid residues or residues interacting otherwise with the 99-loop.

The 99-loop or insertion loop 80-90 (according to chymotrypsinogen numbering) of factor IX encompasses amino acid residues 256 to 268 (F.IX numbering). The 99-loop is positioned near the active site and plays a role in the activation of F.IX. According to Sichler et al. (2003), Tyr-177 locks the 99-loop in an inactive conformation which, in the physiologic complex, is released by cofactor F.VIIIa. F.X is then able to rearrange the unlocked 99-loop and subsequently binds to the active site cleft.

In WO 2010/012451, the inventors demonstrated that in particular the engineered Factor IX variantITV, containing the mutations V181I, K265T and I383V, is able to bypass factor VIII and correct hemophilic phenotype of F.VIII-knockout mice in the presence of neutralizing antibodies (Milanov et al., 2012). In the present invention, additional modifications are provided to generate even more efficacious F.IX molecules in absence of its cofactor F.VIII as well as to generate potent F.IX variants with increased specific activity in presence of its cofactor F.VIII by combination of different single mutations contributing to an increased activity.

The present invention provides a variant of factor IX (F.IX) or activated factor IX (F.IXa), wherein the variant of F.IX is characterized in that it has clotting activity in absence of its cofactor, wherein the cofactor is factor VIII (F.VIII) or activated factor VIII (F.VIIIa).

Said variant factor IX or activated factor IX comprises at least one amino acid substitution in position 265 in combination with amino acid substitution V181I and/or I383V.

The variant with an amino acid substitution in position 265 (preferably K265T or K265A) in combination with amino acid substitution V181I and/or I383V is called the "basis variant factor IX" herein.

Preferably, the variant factor IX according to the invention comprises at least one further amino acid substitution in a position selected from the group of 255 to 269, 383, 181, 6, 44, 72, 75, 102, 105, 122, 185, 224, 263, 338 and/or a modification of the 99-loop.

More preferably, the variant factor IX comprises at least an amino acid substitution selected from K265T, K265A, I383V, V181I, L6F, Q44H, W72R, F75V, S102N, S102K, S102P, S102R, S102Q, S102W, N105S, K122R, E185D, E185S, E185F, E185K, E185P, E185Q, E185R, E224G, E243D, I263S, R338E, T376A and/or a modification of the 99-loop.

The variant factor IX according to the invention comprises at least one amino acid substitution in position 265 in combination with amino acid substitution V181I and/or I383V, and further comprises amino acid substitution(s) in position(s) selected from the group of 6, 11, 25, 44, 54, 72, 75, 78, 86, 89, 102, 105, 113, 119, 122, 125, 135, 139, 154, 159, 185, 195, 196, 211, 219, 222, 224, 236, 243, 251, 260, 262, 263, 268, 289, 299, 302, 304, 310, 319, 330, 334, 336, 338, 366, 368, 376, 383, 386, 391, 392, 394, 399 and/or a modification of the 99-loop, preferably 255 to 269, 383, 6, 44, 72, 75, 102, 105, 122, 185, 224, 263, 338 and/or a modification of the 99-loop, more preferably 6, 102 and/or 185.

In a preferred embodiment, the further amino acid substitution(s) is/are selected from the group of L6F, Q11R, F25L, Q44H, N54D, W72R, F75V, E78D, V86A, N89D, S102N, N105S, E113V, E119V, K122R, E125D, V135A, Q139E, D154N, T159S, E185D, Q195L, V196I, V211I, A219V, C222Y, E224G, I263S, H236L, E243D, I251V, N260K, A262D, I263S, H268D, H268R, C289R, F299T, F302Y, S304F, G310R, K319R, L330I, A334S, R338E, L336H, G366R, P368S, P368I, T376A, I383A, T386A, M391K, K392E, K394R, T399S and/or a modification of the 99-loop, preferably L6F, Q44H, W72R, F75V, S102N, S102K, S102P, S102R, S102Q, S102W, N105S, K122R, E185D, E185S, E185F, E185K, E185P, E185Q, E185R, E224G, E243D, I263S, R338E, T376A and/or a modification of the 99-loop, more preferably L6F, S102N and/or E185D.

In a preferred embodiment, the variant factor IX comprises an amino acid substitution in position 265 (position 98 according to chymotrypsinogen numbering) which is preferably selected from K265T, K265A, K265D, K265E, K265F, K265G, K265H, K265I, K265N, K265S and K265V, more preferably K265T, K265A, in combination with further amino acid substitutions.

In a preferred embodiment, said basis variant factor IX comprises at least an amino acid substitution of the following groups:

| Group A | clotting activity in absence of cofactor F.VIII (F.VIII-independent activity) increased compared to wild type |
| Group B | clotting activity in absence of cofactor F.VIII wherein the F.VIII-independent clotting activity is increased compared to the respective clotting activity of the basis variant |

| | Amino acid position | Amino acid substitution |
|---|---|---|
| Group A | 11, 25, 44, 75, 78, 89, 105, 113, 154, 159, 185, 211, 224, 263, 302, 310, 336 | Q11R, F25L, Q44H, F75V, E78D, N89D, N105S, E113V, D154N, T159S, E185D, V211I, E224G, I263S, F302Y, G310R, L336H |
| Group B | 6, 72, 102, 122, 185, 338, 376 | L6F, W72R, S102N or other amino acid substitution (preferably selected from S102K, S102P, S102R, S102Q, S102W), K122R, E185D or other amino acid substitution (preferably selected from E185S, E185F, E185K, E185P, E185Q, E185R), R338E, T376A |

The amino acid substitution in position 265 is preferably selected from K265T, K265A, K265D, K265E, K265F, K265G, K265H, K265I, K265N, K265S and K265V, preferably K265T, K265A.

In a preferred embodiment, the further amino acid substitution(s) is/are selected from position(s) 6, 102 and 185, preferably,
L6F, S102N, S102K, S102P, S102R, S102Q, S102W, E185D, E185S, E185F, E185K, E185P, E185Q, E185R,
wherein in one embodiment, the amino acid substitution in position 265 is K265T or K265A.

The variant factor IX according to the invention is preferably selected from
variant V181I/K265T/I383V/L6F,
variant V181I/K265T/I383V/S102N,
variant V181I/K265T/I383V/E185D,
variant V181I/K265T/I383V/E185S,
variant V181I/K265T/I383V/L6F/S102N,
variant V181I/K265T/I383V/L6F/S102K,
variant V181I/K265T/I383V/S102N/E185D, and
variant V181I/K265T/I383V/S102N/E185S.

The variant factor IX according to the invention is preferably selected from
variant V181I/K265A/I383V/L6F,
variant V181I/K265A/I383V/S102N,
variant V181I/K265A/I383V/E185D,
variant V181I/K265A/I383V/E185S,
variant V181I/K265A/I383V/L6F/S102N,
variant V181I/K265A/I383V/L6F/S102K,
variant V181I/K265A/I383V/S102N/E185D, and
variant V181I/K265A/I383V/S102N/E185S.

More preferably, the variant factor IX according to the invention is selected from
variant V181I/K265A/I383V/L6F, and
variant V181I/K265A/I383V/E185D.

Variant Proteins of Factor IX with Increased F.IX Clotting Activity

According to the present invention this object is solved by providing a variant of factor IX (F.IX) or activated factor IX (F.IXa), wherein the variant of F.IX is characterized in that it has increased clotting activity in presence of its cofactor compared to wild type,
wherein the cofactor is factor VIII (F.VIII) or activated factor VIII (F.VIIIa).

The term "increased clotting activity in presence of its cofactor" is also called herein as "hyperfunctional F.IX activity".

The variant factor IX according to the invention comprises preferably an amino acid substitution in a position selected from the group of
5, 6, 10, 11, 44, 72, 75, 78, 102, 105, 122, 135, 159, 185, 186, 211, 224, 243, 262, 263, 268, 327, 338, 367, 368, 376, 383, 394,
preferably the amino acid substitution R338L or R338E in combination with at least one of K5A, K5F, L6F, V10K, V10F, V10R, Q11R, Q11H, Q11K, Q44H, W72R, F75V, E78D, S102N, N105S, K122R, V135A, T159S, E185D, D186E, V211I, E224G, E243D, A262D, I263S, H268R, R327S, N367D, P368I, T376A, I383A, K394R,
more preferably K5A, L6F, Q11R, Q44H, W72R, F75V, E78D, S102N, N105S, K122R, E185D, D186E, V211I, E224G, E243D, I263S, T376A, K394R.

Preferably, the variant factor IX according to the invention comprises at least one amino acid substitution in a position selected from the group of
5, 6, 10, 11, 44, 72, 75, 102, 105, 122, 185, 224, 243, 263, 338, 376.

The present invention provides a variant of factor IX (F.IX) or activated factor IX (F.IXa), wherein the variant of F.IX is characterized in that it has increased clotting activity in presence of its cofactor compared to wild type, wherein the cofactor is factor VIII (F.VIII) or activated factor VIII (F.VIIIa).

Said variant factor IX or activated factor IX comprises at least one amino acid substitution in position 338 (preferably R338L or R338E) in combination with an amino acid substitution in position 377 (preferably S377W).

In a preferred embodiment, said variant factor IX comprising an amino acid substitution in position 338 (preferably R338L or R338E) in combination with an amino acid substitution in position 377 (preferably S377W), comprises at least an amino acid substitution of the following groups:

| Group D | increased clotting activity in presence of cofactor F.VIII (F.VIII-dependent activity) increased compared to wild type |

| | Amino acid position | Amino acid substitution |
|---|---|---|
| Group D | 5, 6, 10, 11, 44, 72, 75, 102, 105, 122, 185, 211, 224, 243, 263, 338, 376 | K5A, L6F, Q11R, Q44H, W72R, F75V, E78D, S102N, N105S, K122R, E185D, D186E, V211I, E224G, E243D, I263S, R338E, T376A, K394R |

The present invention provides a variant of factor IX (F.IX), which is characterized in that it has increased clotting activity in presence of its cofactor compared to wild type, wherein the cofactor is factor VIII (F.VIII) or activated factor VIII (F.VIIIa), said variant factor IX or activated factor IX comprising an amino acid substitution in position 338 in combination with amino acid substitution(s) in position(s) selected from the group of 4, 5, 6, 10, 11, 44, 72, 75, 78, 102, 105, 122, 135, 159, 185, 186, 211, 224, 243, 262, 263, 265, 268, 327, 367, 368, 376, 377, 383, 394, preferably 4, 5, 6, 10, 11, 44, 72, 75, 102, 105, 122, 185, 224, 243, 263, 265, 376, 377, more preferably 377, 10, 4, 5 and/or 265.

In a preferred embodiment, the further amino acid substitution(s) is/are selected from the group of G4Y, K5A, K5F, L6F, V10K, V10F, V10R, Q11R, Q11H, Q11K, Q44H, W72R, F75V, E78D, S102N, N105S, K122R, V135A, T159S, E185D, D186E, V211I, E224G, E243D, A262D, I263S, K265T, H268R, R327S, N367D, P368I, T376A, S377W, I383A, K394R, preferably K5A, L6F, Q11R, Q44H, W72R, F75V, E78D, S102N, N105S, K122R, E185D, D186E, V211I, E224G, E243D, I263S, K265T, T376A, S377W, K394R, more preferably S377W, V10K, G4Y, K5A and/or K265T.

In a preferred embodiment, the variant factor IX comprises the amino acid substitution in position 338 in combination with an amino acid substitution in position 5, an amino acid substitution in position 10, and/or an amino acid substitution in position 377.

Preferably, the amino acid substitution in position 338 is R338L or R338E, wherein the amino acid substitution in position 5 is K5A, wherein the amino acid substitution in position 10 is V10K, and/or wherein the amino acid substitution in position 377 is S377W.

The variant factor IX according to the invention is preferably selected from variant V10K/R338L
variant R338L/S377W
variant V10K/R338L/S377W
variant V10K/R338L/S377W/L6F
variant V10K/R338L/S377W/E243D
variant V10K/R338L/S377W/E224G
variant V10K/R338L/S377W/L6F/E224G
variant V10K/R338L/S377W/E243D/E224G
variant V10K/R338L/S377W/K265T
variant K5A/R338L
variant K5A/R338L/S377W
variant K5A/V10K/R338L/S377W
variant G4Y/V86A/R338L/S377W, and
variant G4Y/V86A/R338L/S377W/K265T.

Disclaimer:

The present invention does not encompass a variant factor IX already disclosed in the earlier application of the inventors WO 2010/012451. In particular the present invention does not encompass:

single variants: R338A, S377W, G4Y, V86A, K265T, K265A
variant G4Y/V10K,
variant S340T/R338A/Y345T,
variant R338A/S377W,
variant S360A/R338A/S377W,
variant V86A/R338A/S377W,
variant G4Y/R338A/S377W,
variant R338A/K265T,
variant K265T/R338A/I383V,
variant Y259F/K265T/R338A/T340S/Y345T,
variant V181I, K265T/I383V,
variant V181I/K265T/R338A/S377W/I383V.

Furthermore, the present invention does not encompass the following variants, such as disclosed in Chang et al., 1998, WO 99/03496 A1, US 2008/167219 A1, Chang et al., 2002, or Kao et al., 2013 or reviewed in Quade-Lyssy et al., 2012:

single variants: K5A, V10K, V86A, E277A, R338A, R338L,
single variants: S102A, E113A, K122A, N105A,
variant K5A/V10K,
variant V86A/E277A,
variant E277A/R338A,
variant V86A/E277A/R338A,
variant V86A/E277A/R338L,
variant Y259F/K265T/Y345T.

Conjugates

In a preferred embodiment, the variants of factor IX according to the invention comprise a further compound or moiety, which is preferably covalently attached to the variant (conjugate).

Preferably, the further compound or moiety is selected from a protein, such as albumin,
a label, such as chromophor, fluorophor, isotope, and/or
a bio-/polymer, such as chitosan, PEG.

In one embodiment, the chitosan-conjugates are suitable for gene therapy, such as for oral gene delivery of the F.IX variants.

Nucleic Acids of the F.IX Variants and Pharmaceutical Compositions

According to the present invention the above object is furthermore solved by providing nucleic acids encoding the variant factor IX according to the present invention.

A "nucleic acid" refers to DNA, RNA and derivatives thereof, DNA and/or RNA comprising modified nucleotides/nucleosides.

Preferably, the nucleic acid is operably linked to a promoter and/or terminator sequence. Preferred promoter and/or terminator sequences are the human alpha1 anti-trypsin promoter, the hepatic locus control region 1, or the cytomegalovirus promoter and a polyadenylation signal of human or bovine growth hormone of the Simianese Virus 40.

The skilled artisan is able to select suitable promoter and/or terminator sequences.

A nucleic acid is "operably linked" to a promoter and/or terminator sequence when the transcription/translation of the nucleic acid is controlled by the respective promoter/terminator, preferably in a cell and by the cellular transcription/translation machinery, such that e.g. the encoded protein can be obtained from the nucleic acid.

Preferably, the nucleic acid is an expression plasmid, a gene therapy or delivery construct, a sequence encoded in a gene transfer vector, a gene sequence used for DNA modification or repair, or similar.

Preferred gene therapy or delivery constructs are viral and non-viral vectors, such as adeno-associated viral vectors (AAV), plasmid vectors, or minicircle vectors, as described e.g. in Schuettrumpf et al., 2005 and Milanov et al., 2012, or chitosan nanoparticles.

A preferred gene therapy or delivery construct is a minicircle vector, such as a minicircle under the control of a liver-directed or a CMV promoter.

For example, such as for in vivo expression, a nucleic acid encoding the variant F.IX according to the present invention (e.g. a F.IX expression cassette) is introduced into a minicircle producer plasmid, such as pMC.BESPX-MCS2 (System Biosciences), and controlled by e.g. the strong liver-specific enhancer/promoter HCR/hAAT (hepatic locus control region 1/human α-1-antitrypsin) or the CMV promoter.

Such minicircle vectors can be administered by injection, parenterally, or orally when encapsulated in chitosan nanoparticles.

For details, see Example 1.

A preferred gene therapy or delivery construct are chitosan nanoparticles, which are particularly suitable for oral gene delivery and are described in the art, see Mao et al., 2001 or Bowman & Leong, 2006.

The nanoparticles contain chitosan and the nucleic acid, preferably DNA.

Chitosan, a non-toxic and biodegradable polysaccharide derived from partial deacetylation of chitin, can be used to form nanoparticles as a potent oral drug and gene delivery system, reviewed in Bowman & Leong, 2006. Nanoparticles are formed through electrostatic interaction between anionic DNA and cationic chitosan protecting the encapsulated DNA from digestion and enhancing uptake in the gut by improving intestinal trans- and paracellular permeability and its mucoadhesive nature.

For details, see Example 2

According to the present invention the object is furthermore solved by providing a pharmaceutical composition comprising at least one variant of factor IX (F.IX) of the invention or at least one nucleic acid of the invention, and optionally pharmaceutically acceptable carrier(s) and/or excipient(s).

Suitable pharmaceutically acceptable carrier(s) and/or excipient(s) are known in the art. The skilled artisan will selected the preferred pharmaceutically acceptable carrier(s) and/or excipient(s) depending on the intended application of the pharmaceutical composition, such as disorder to be treated, patient to be treated, treatment regimen etc.

Medical Uses

According to the present invention the object is furthermore solved by providing the variants of factor IX, as disclosed in the present invention or the nucleic acids encoding them or the pharmaceutical compositions of the invention for the diagnosis, prevention and/or treatment of diseases.

The disease to be diagnosed, prevented and or treated is preferably a bleeding disorder or bleeding.

A "bleeding disorder" is preferably hemophilia A and/or hemophilia B, hemophilia caused or complicated by inhibitory antibodies to factor VIII, by a deficiency of factor VIII or factor IX, or by the presence of a non functional factor VIII or factor IX protein, or any other bleeding or bleeding tendency.

Preferably, the bleeding disorder is hemophilia A, hemophilia caused or complicated by inhibitory antibodies to factor F.VIII or F.VIIIa, hemophilia B.

Preferably, the bleeding disorder or bleeding is a bleeding disorder where by-passing agents are used, including e.g. neonatal coagulopathies; severe hepatic disease; high-risk surgical procedures; traumatic blood loss; bone marrow transplantation; thrombocytopenias and platelet function disorders; urgent reversal of oral anticoagulation; congenital deficiencies of factors V, VII, X, and XI; and von Willebrand disease with inhibitors to von Willebrand factor, blood loss in connection with large injuries, cerebral bleedings, thrombocyte function disorders.

Preferably, the variant of factor IX (F.IX), the nucleic acid or the pharmaceutical composition of the invention are used for protein infusion therapy, cellular therapy, gene delivery or therapy and/or prophylaxis of a bleeding disorder or bleeding.

In one embodiment, gene therapy or delivery comprises the use of a gene therapy or delivery construct that comprises the variant of factor IX (F.IX), the nucleic acid or the pharmaceutical composition.

Preferred gene therapy or delivery constructs are viral and non-viral vectors, such as adeno-associated viral vectors (AAV), plasmid vectors, or minicircle vectors, as described e.g. in Schuettrumpf et al., 2005 and Milanov et al., 2012, or chitosan nanoparticles.

Such minicircle vectors can be administered by injection, parenterally, or orally.

The variants of the present invention are suitable tools to treat patients with bleeding disorder using protein administration, or cell- or gene therapeutic administration (viral, DNA, RNA, or other vectors). Diseases for treatment are hemophilia A and B, also caused or complicated by inhibitory antibodies to FVIII, for treatment of bleeding and for prophylactic therapy.

The inventors have shown that the variants of the present invention
- improve thrombin generation dose-dependent in the absence of F.VIII and show marginal effects in the presence of F.VIII in comparison to wild type F.IX,
- improve F.X activation in the presence and absence of F.VIII,
- correct clotting time in presence of inhibitory antibodies against F.VIII (confirming the function of the tested F.IX variants also in presence of F.VIII inhibitors),
- are not pre-activated but zymogen-like,
- correct coagulation and stop bleeding in vivo (being the first evidence that F.IX variants can serve as hemostatically active therapeutics in vivo), For further details, see Examples 6-8 and FIGS. 1-7.

Screening Method

According to the present invention, the object is furthermore solved by providing a method for screening of anticoagulant compounds (anticoagulants), preferably substances that directly inhibit F.IXa.

Such a method comprises the use of at least one variant factor IX of the present invention, as defined herein.

In such a method, no further components of the tenase complex are necessary (wherein "tenase" refers to complex of the activated forms of the blood coagulation factors factor VIII (F.VIIIa) and factor IX (F.IXa). It forms on a phospholipid surface in the presence of calcium and is responsible for the activation of factor X).

An advantageous aspect of the described variants is, that without need for F.VIIIa and higher activity towards both, F.X cleavage and chromogenic substrate cleavage, the variants are suitable tools in diagnostic testing systems or for the development and screening for direct F.IXa inhibitory substances, which since a long time are desired as anticoagulants, but for which no effective screening was possible, due to the low efficacy of F.IXa without assembly in the tenase complex.

A screening method according to the invention is preferably a method for identifying a compound which binds to a variant factor IX of the present invention and/or which modulates its activity,
preferably comprising the following steps:
providing compounds/substances to be tested,
providing at least one variant factor IX of the present invention,
contacting a compound/substance to be tested with the at least one variant factor IX of the present invention,
determining whether the compound/substance binds to the at least one variant factor IX,
optionally, determining whether the compound/substance modulates the activity of the at least one variant factor IX.

The following examples and drawings illustrate the present invention without, however, limiting the same thereto.

BRIEF DESCRIPTION OF THE DRAWINGS

Figure 7A:
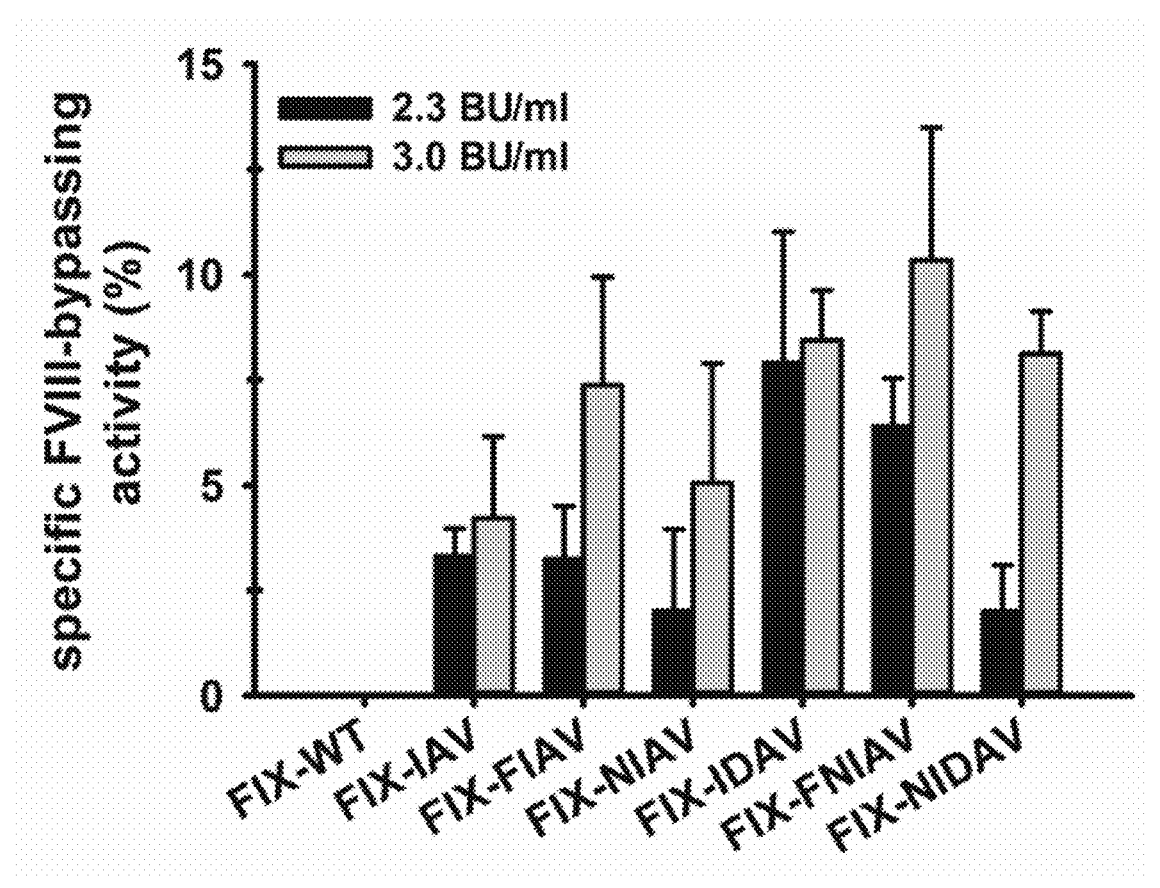

FIGS. 7A-7B In vitro efficacy of F.IX variants
(7A) Clotting activity of F.IX variants in the presence of FVIII neutralizing antibodies.
(7B) Activation status of F.IX variants.
FIGS. 10A-10D In vivo transfection efficiency after oral administration of chitosan-DNA nanoparticles to HB mice.
(10A) Time schedule.
(10B) Immunostaining of reporter gene GFP in small intestine after oral administration of a single dose of unformulated and chitosan formulated eGFP. GFP staining remained undetectable in liver, spleen and colon.
(10C) Delivery of chitosan formulated FIX-WT or hyperfunctional FIX muteins to small intestine after oral administration of a single dose.
(10D) mRNA expression in tissues after single feeding determined by quantitative RT-PCR 72 h post-treatment. Data represent means±SD, n=3/group.

EXAMPLES

Example 1

Figure 1A:
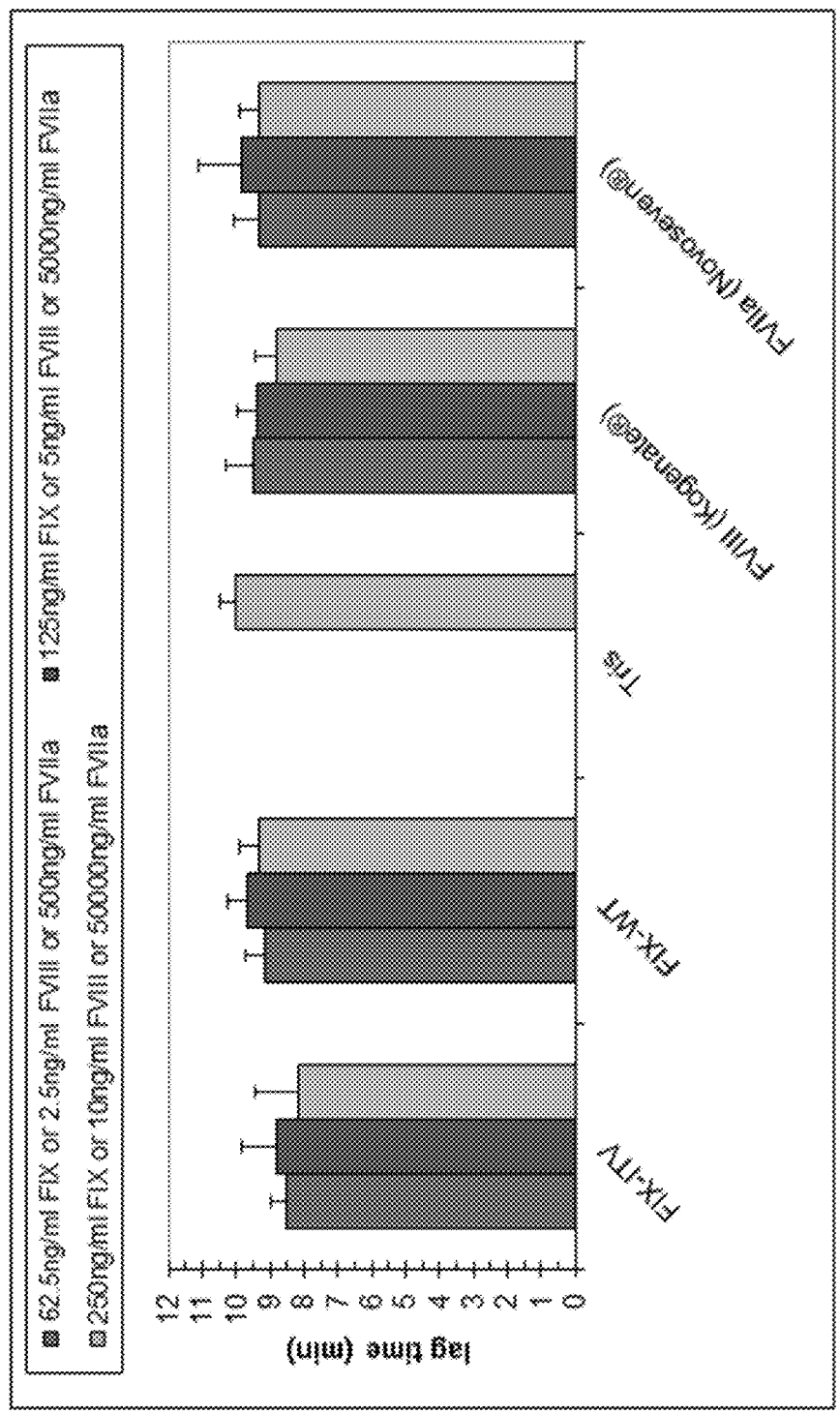
FIGS. 1A-1E TGA of F.IX variant ITV in F.VIII-deficient plasma
(RD 1:20)
(1A) lag time. (1B) peak thrombin. (1C) velocity index. (1D) AUC. (1E) Representative graph.
Figure 1B:
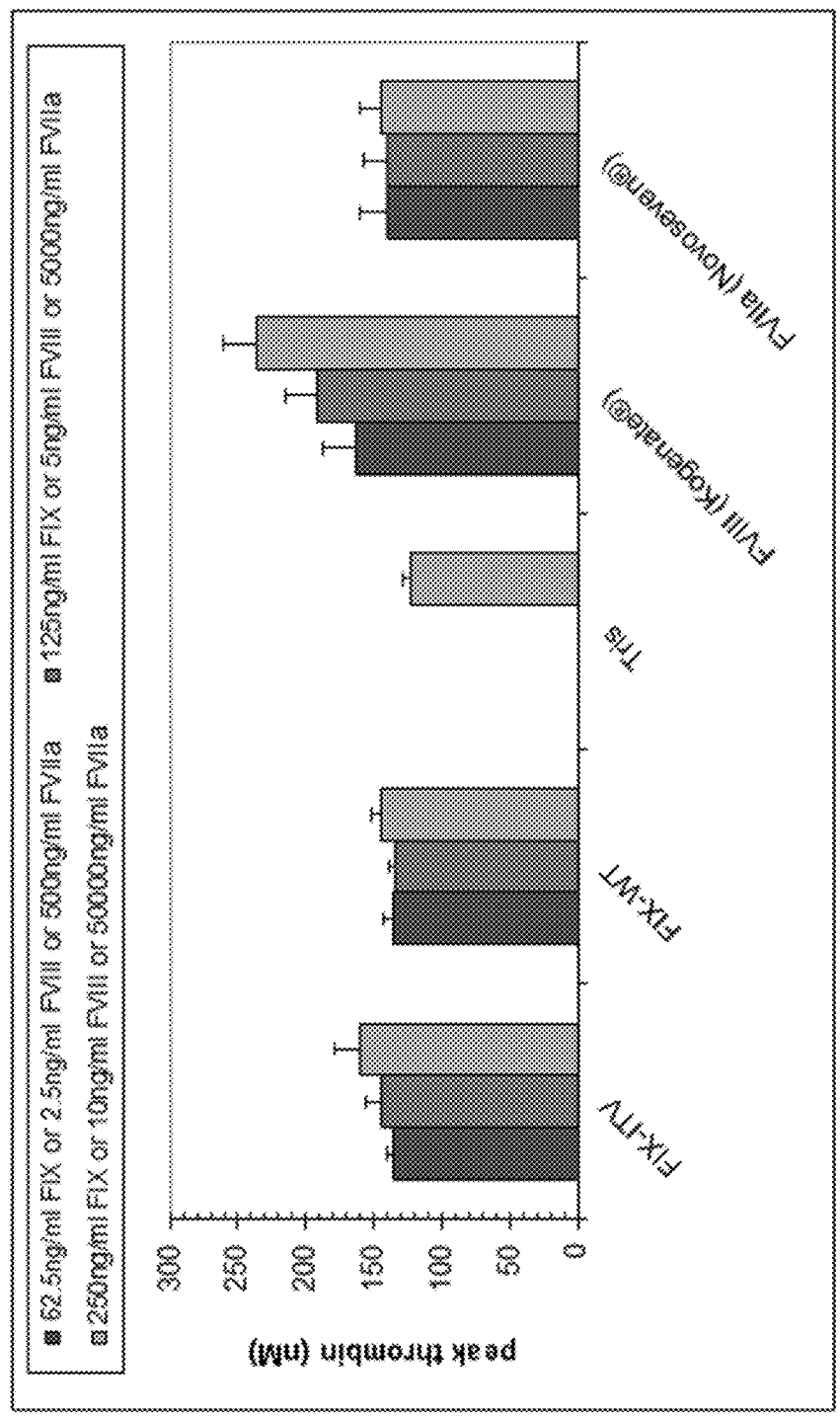
Figure 1C:
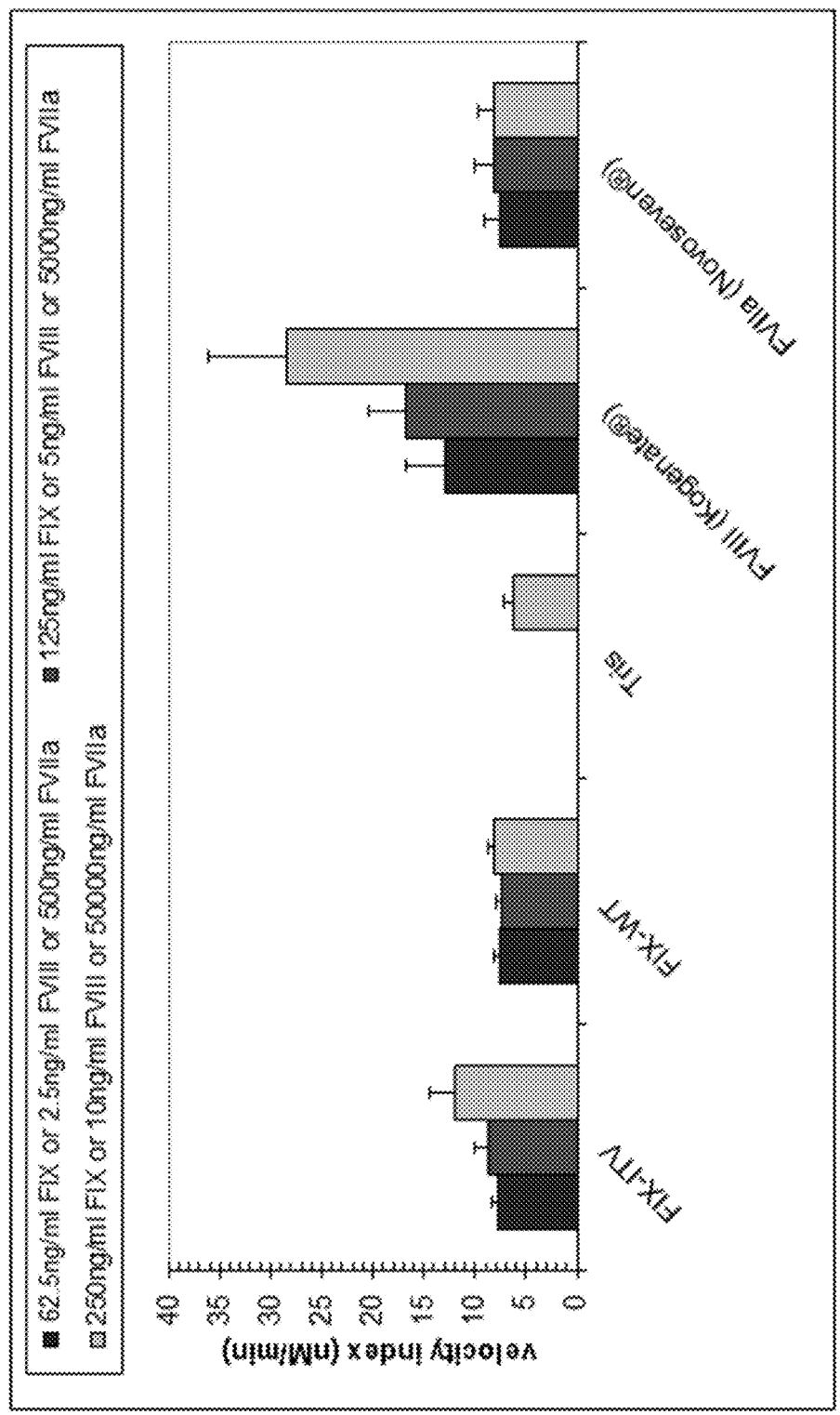
Figure 1D:
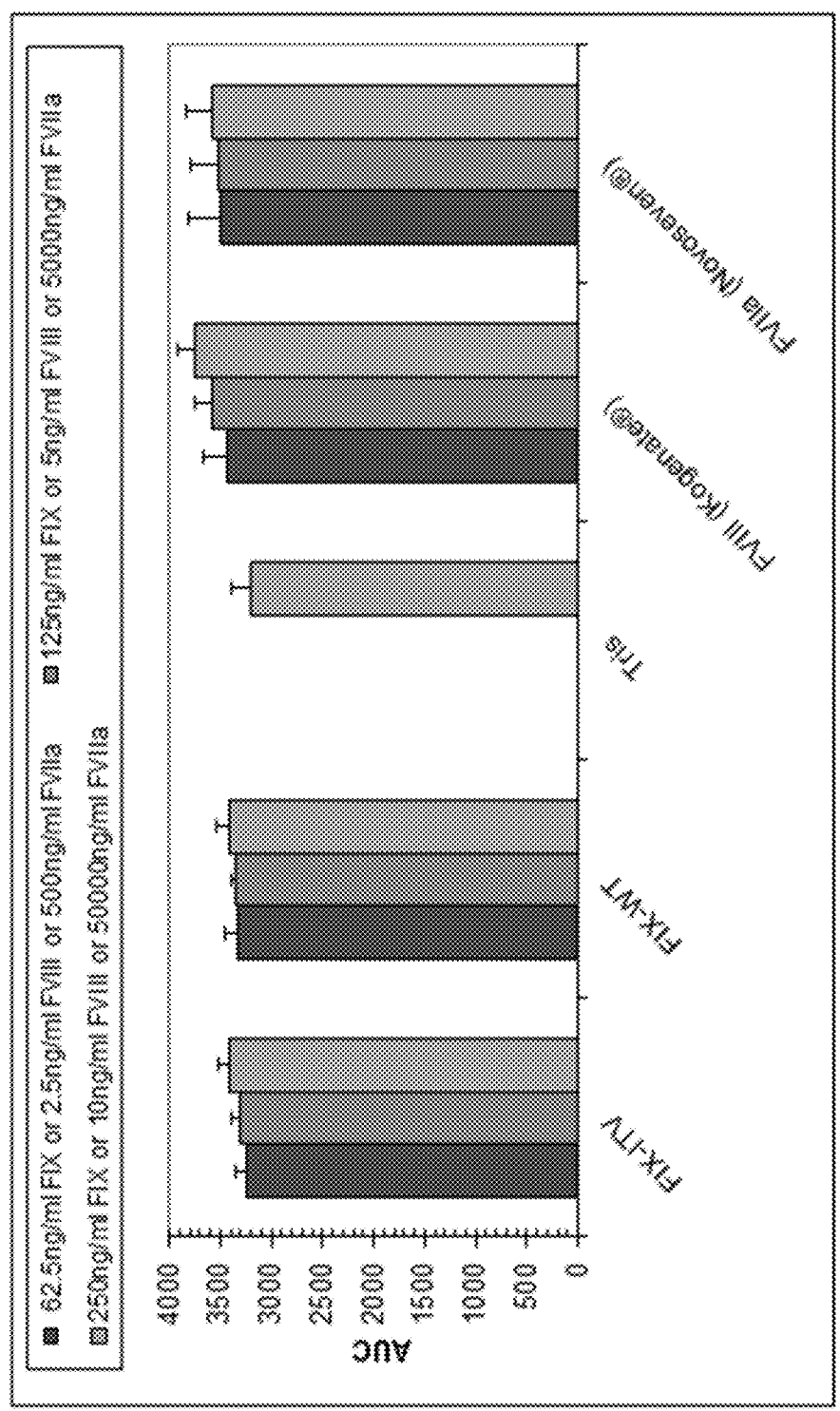
Figure 1E:
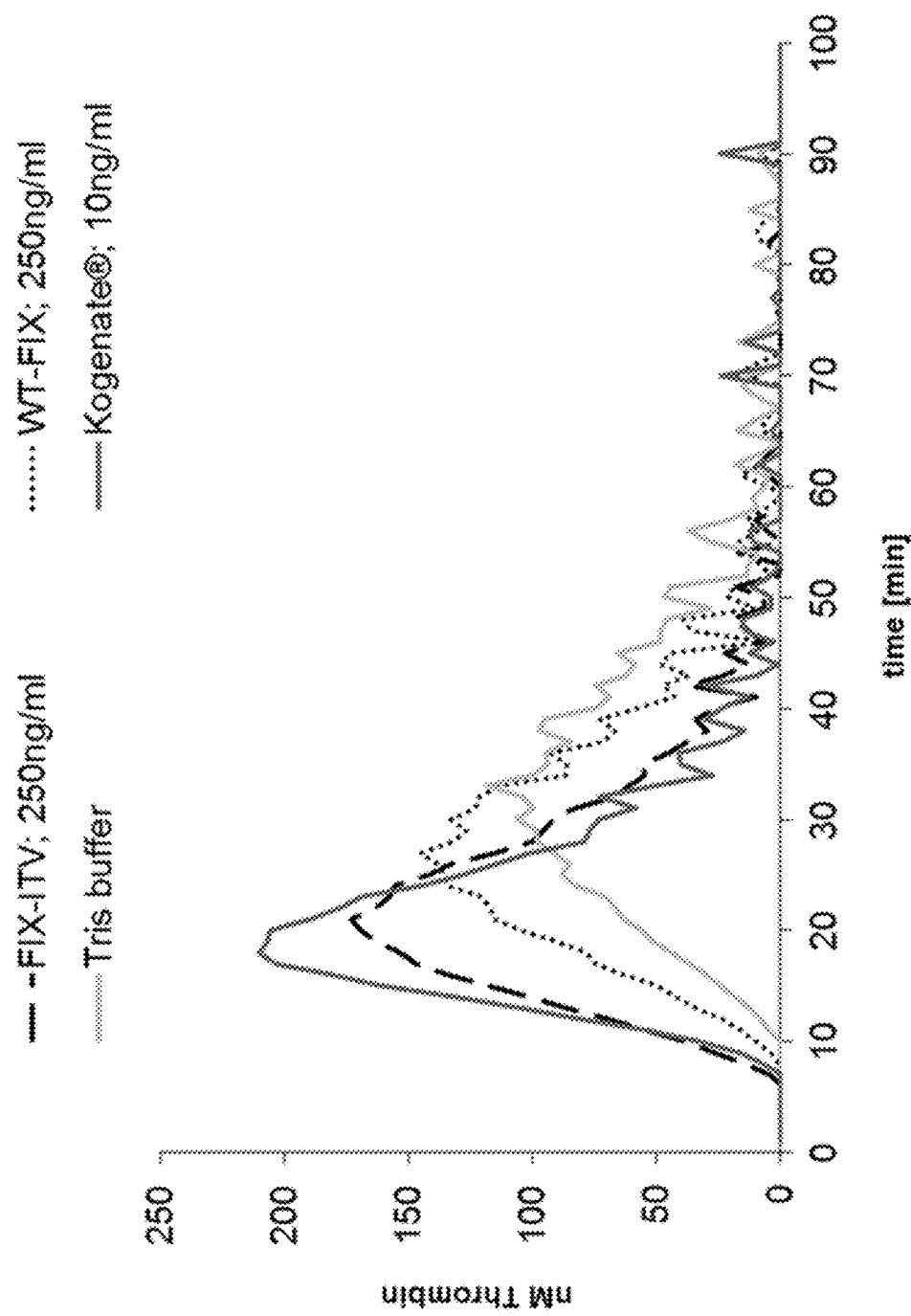
Figure 2A:
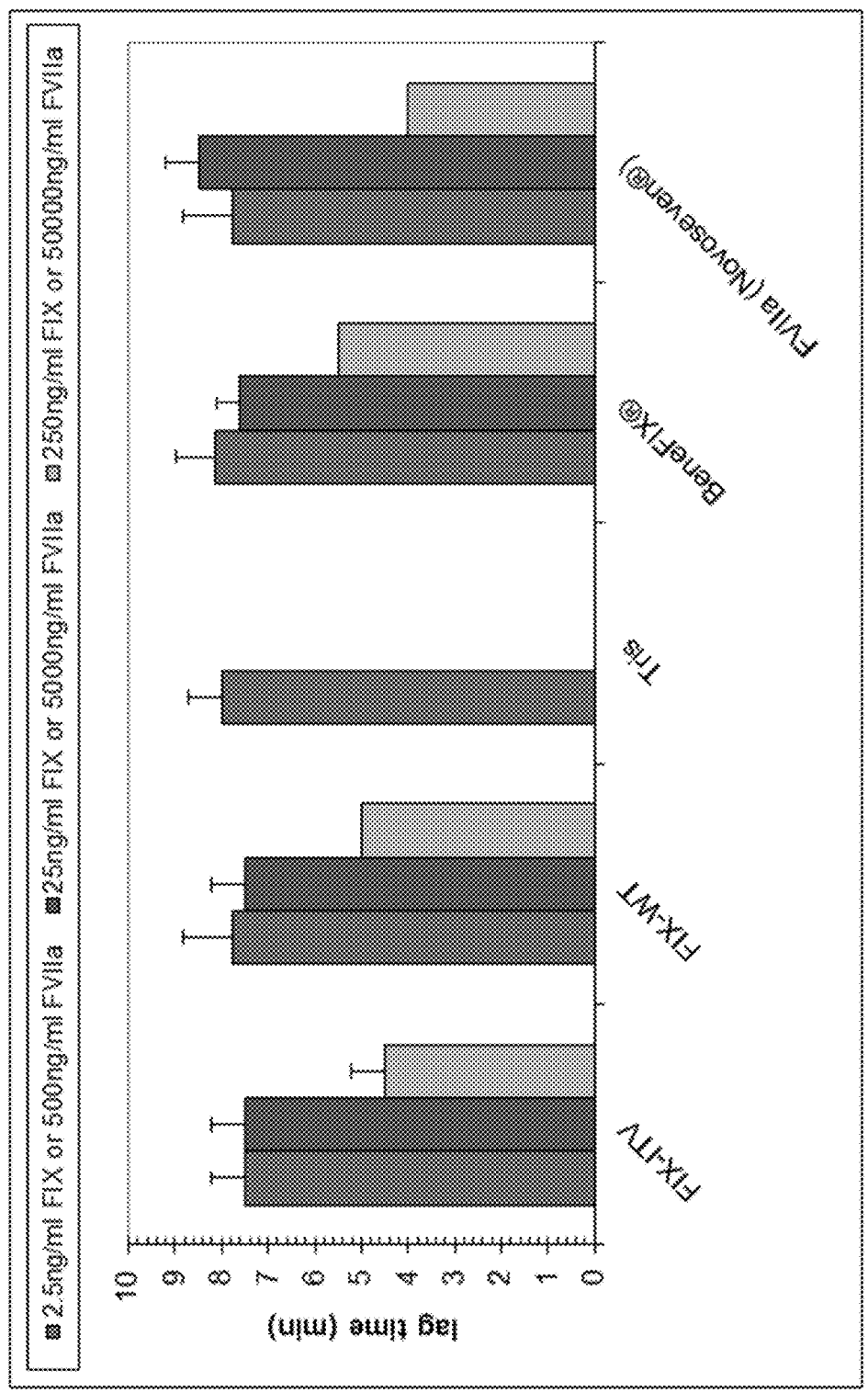
FIGS. 2A-2E TGA of F.IX variant ITV in F.VIII-deficient plasma
(RD 1:20)
(2A) lag time. (2B) peak thrombin. (2C) velocity index. (2D) AUC. (2E) Representative graph.
Figure 2B:
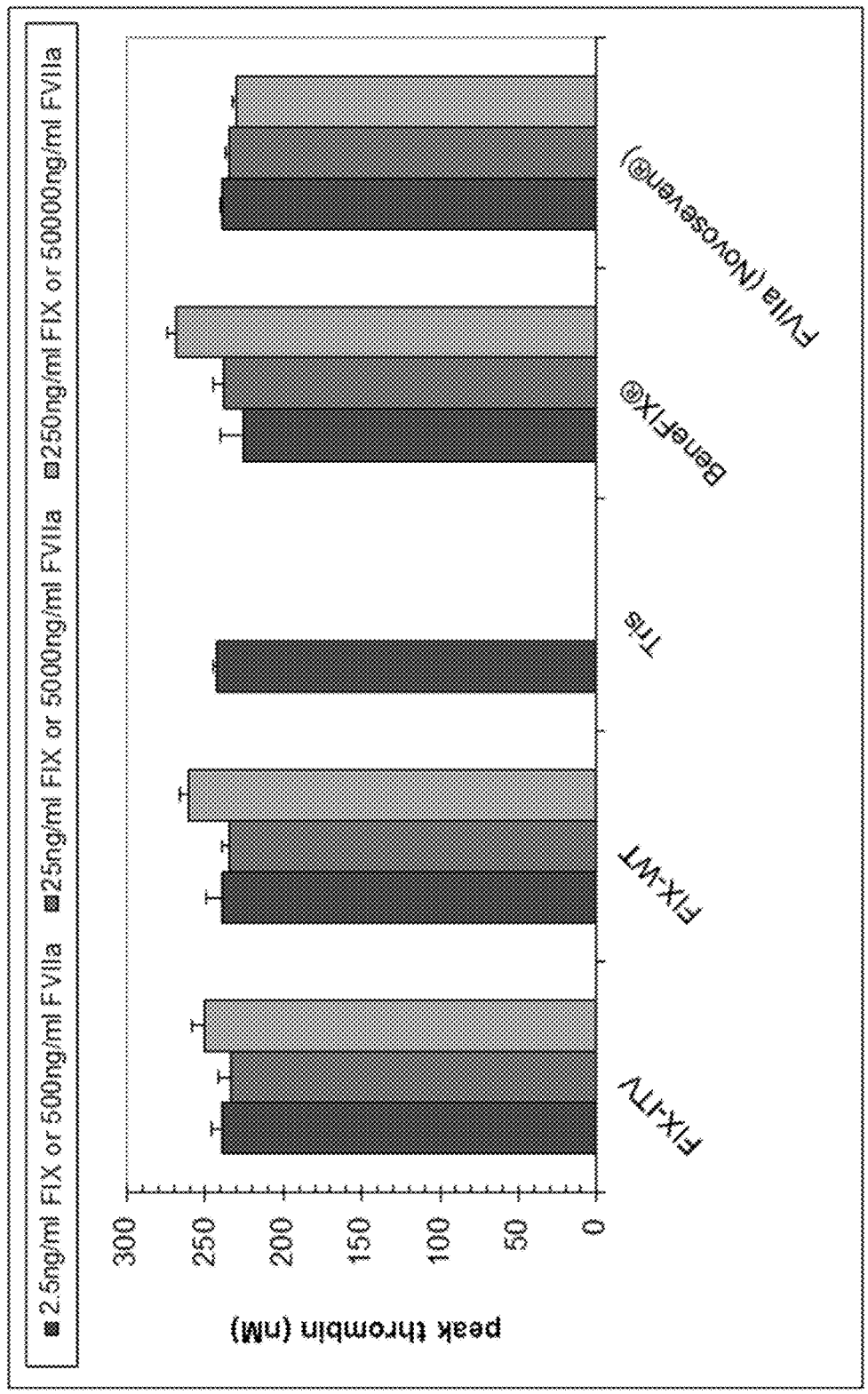
Figure 2C:
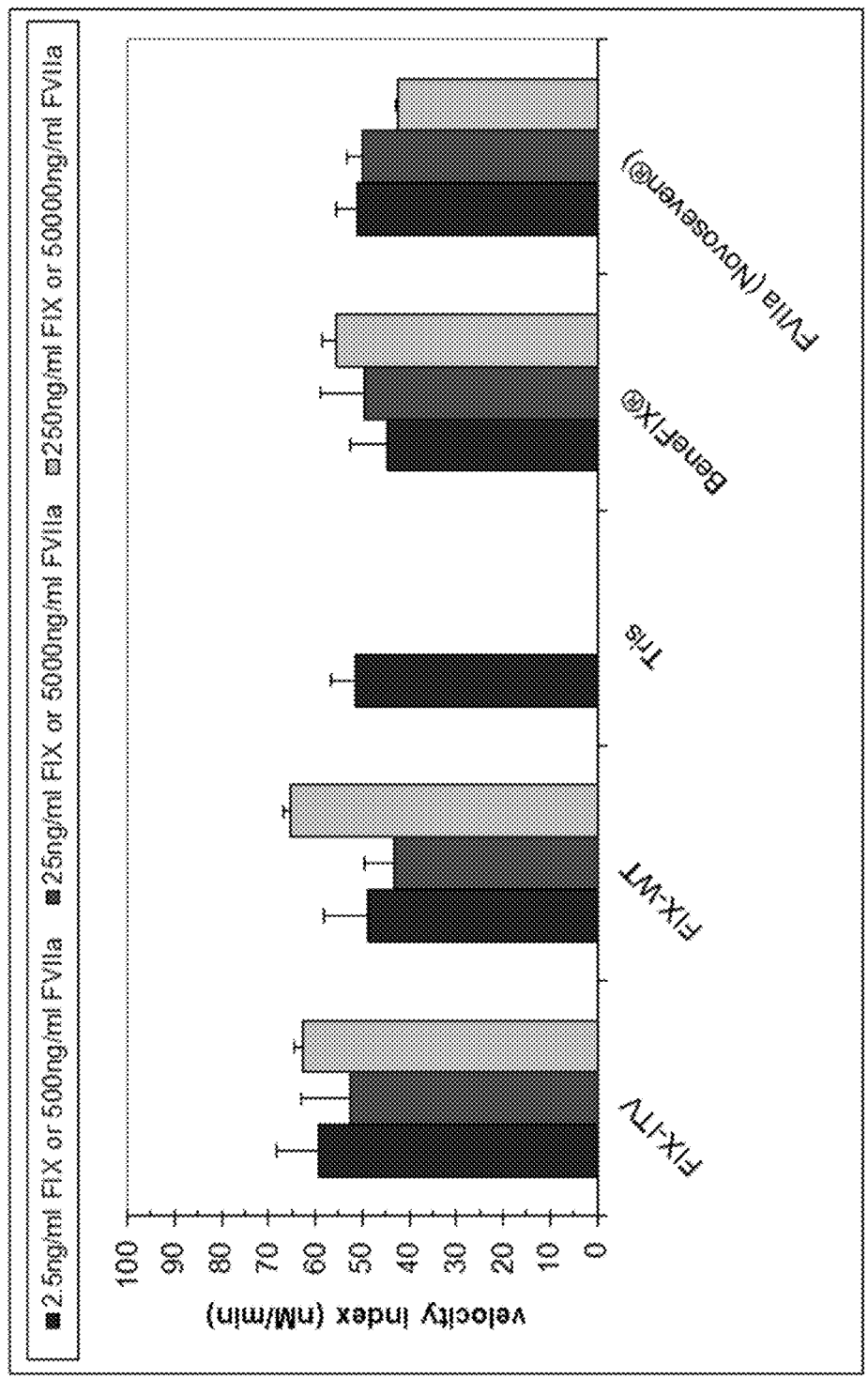
Figure 2D:
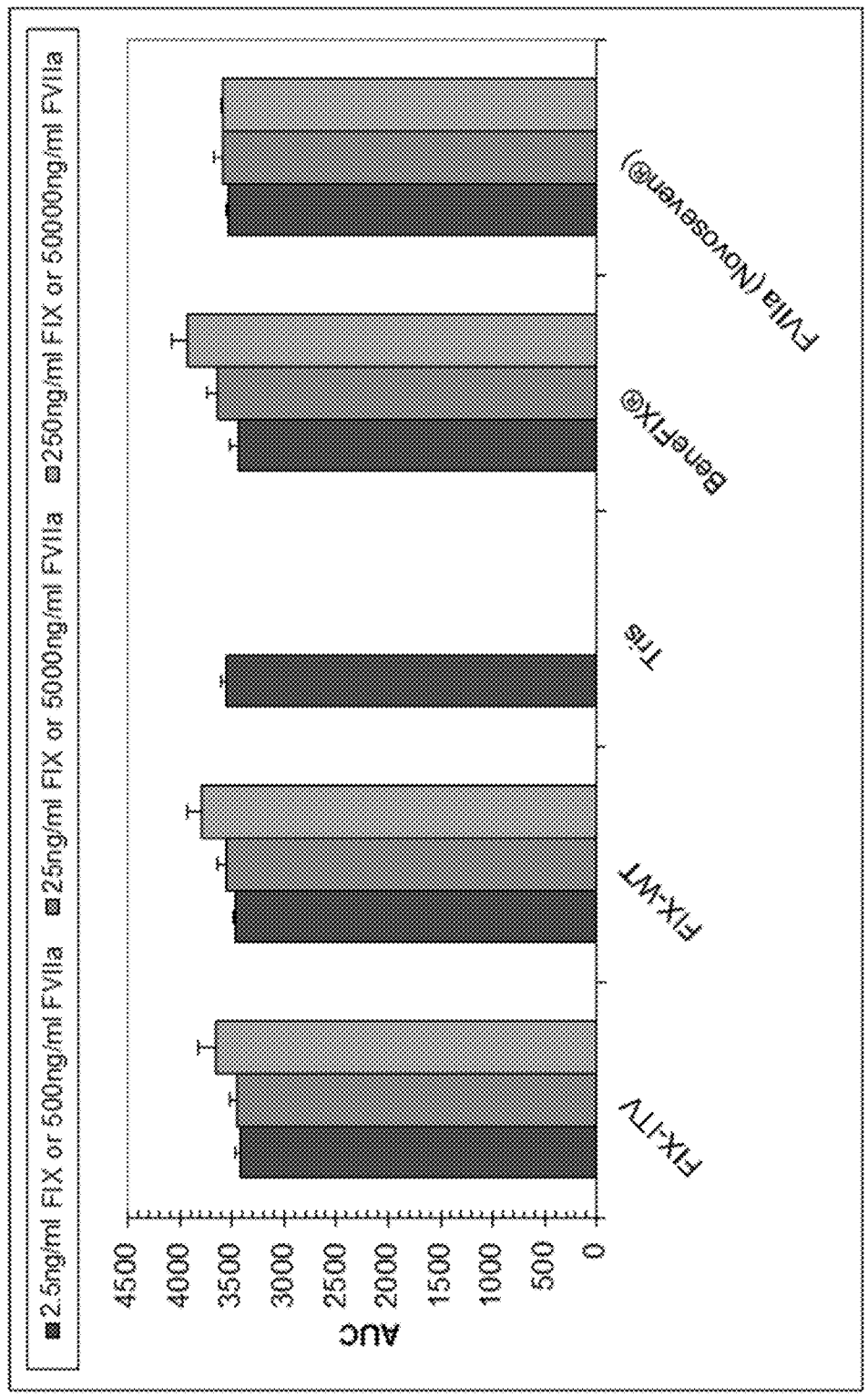
Figure 2E:
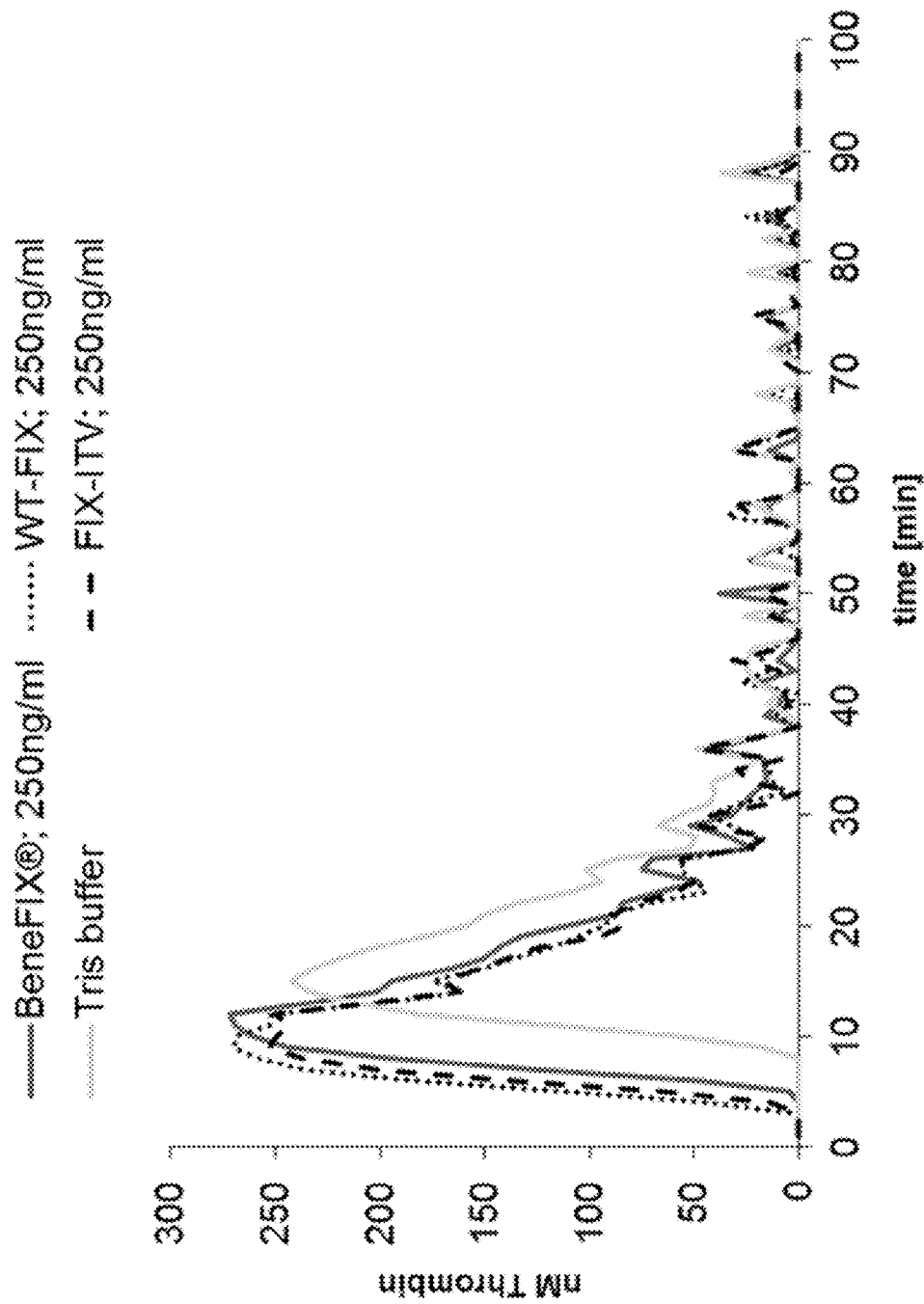
Figure 3A:
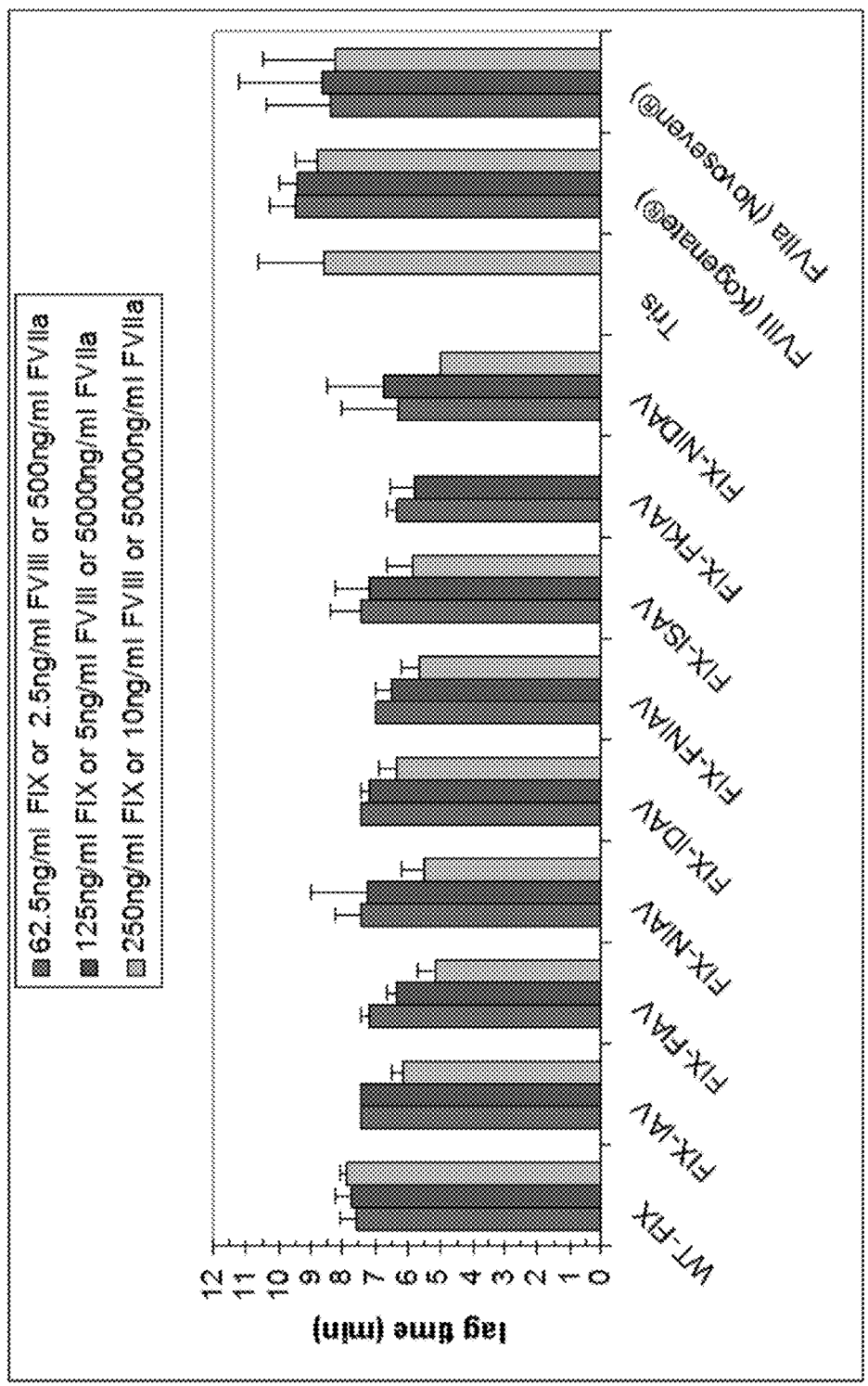
FIGS. 3A-3E TGA of F.IX variants with F.VIII-independent activity in F.VIII-deficient plasma
(RD 1:20)
(3A) lag time. (3B) peak thrombin. (3C) velocity index. (3D) AUC. (3E) Representative graph.
Figure 3B:
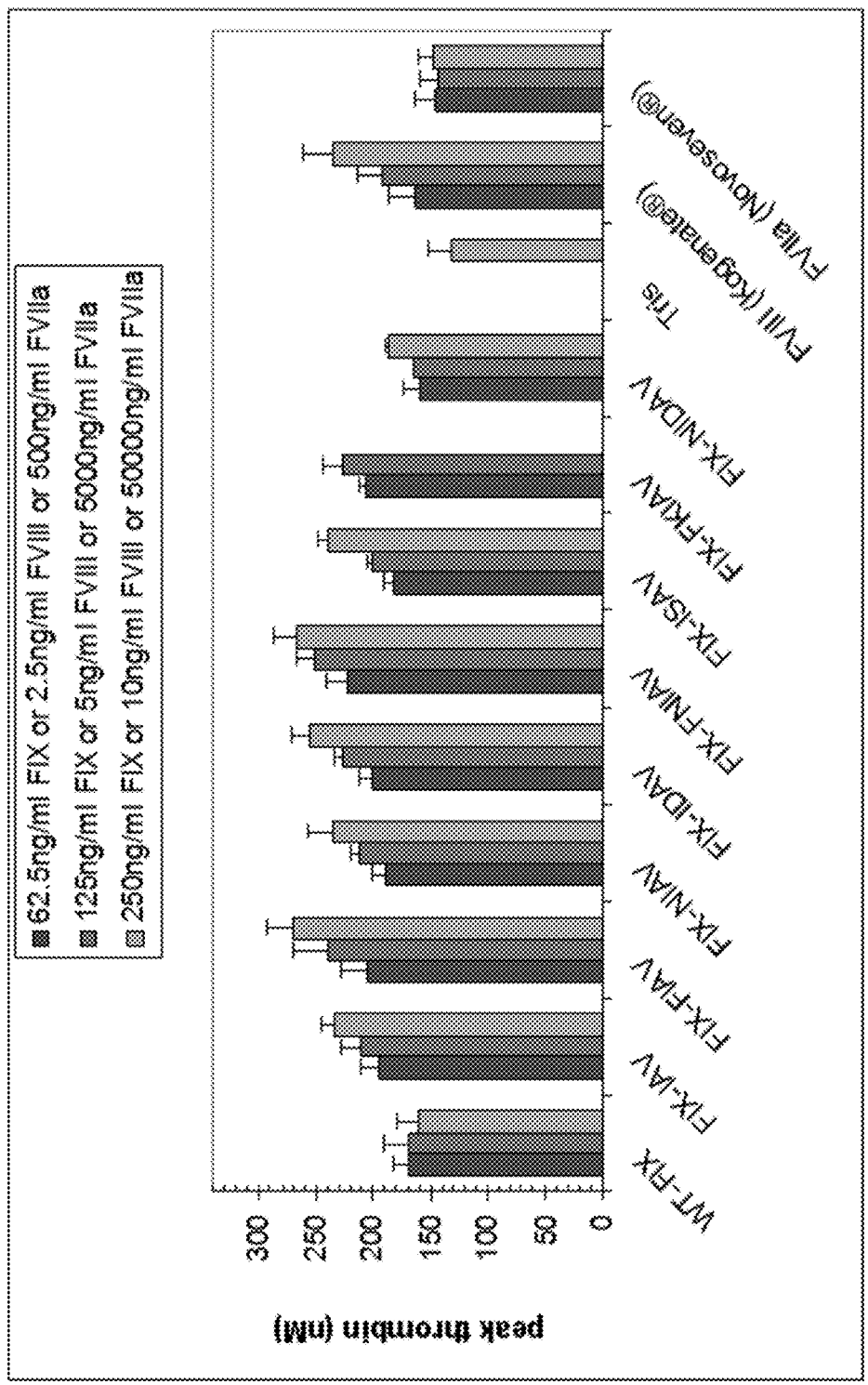
Figure 3C:
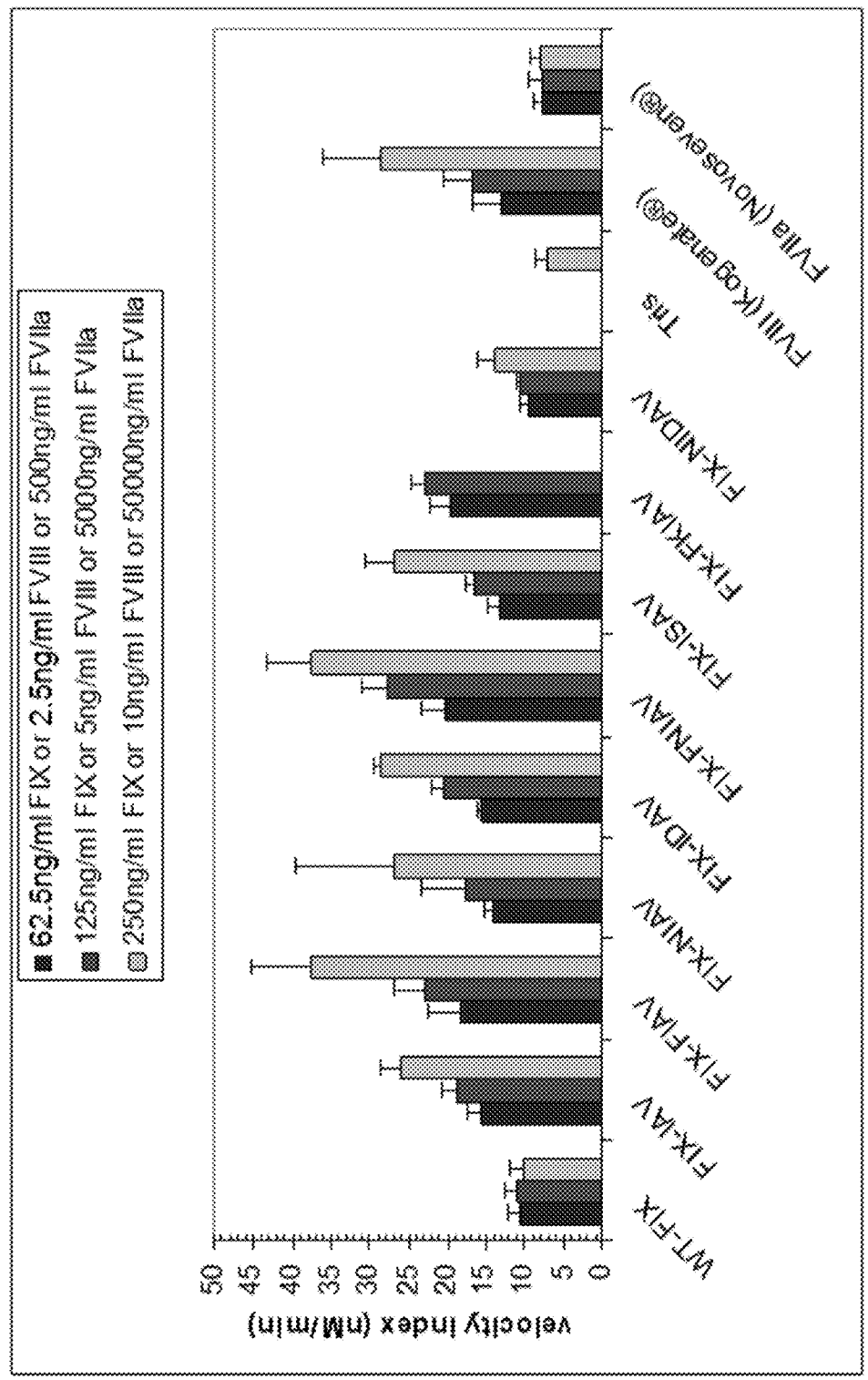
Figure 3D:
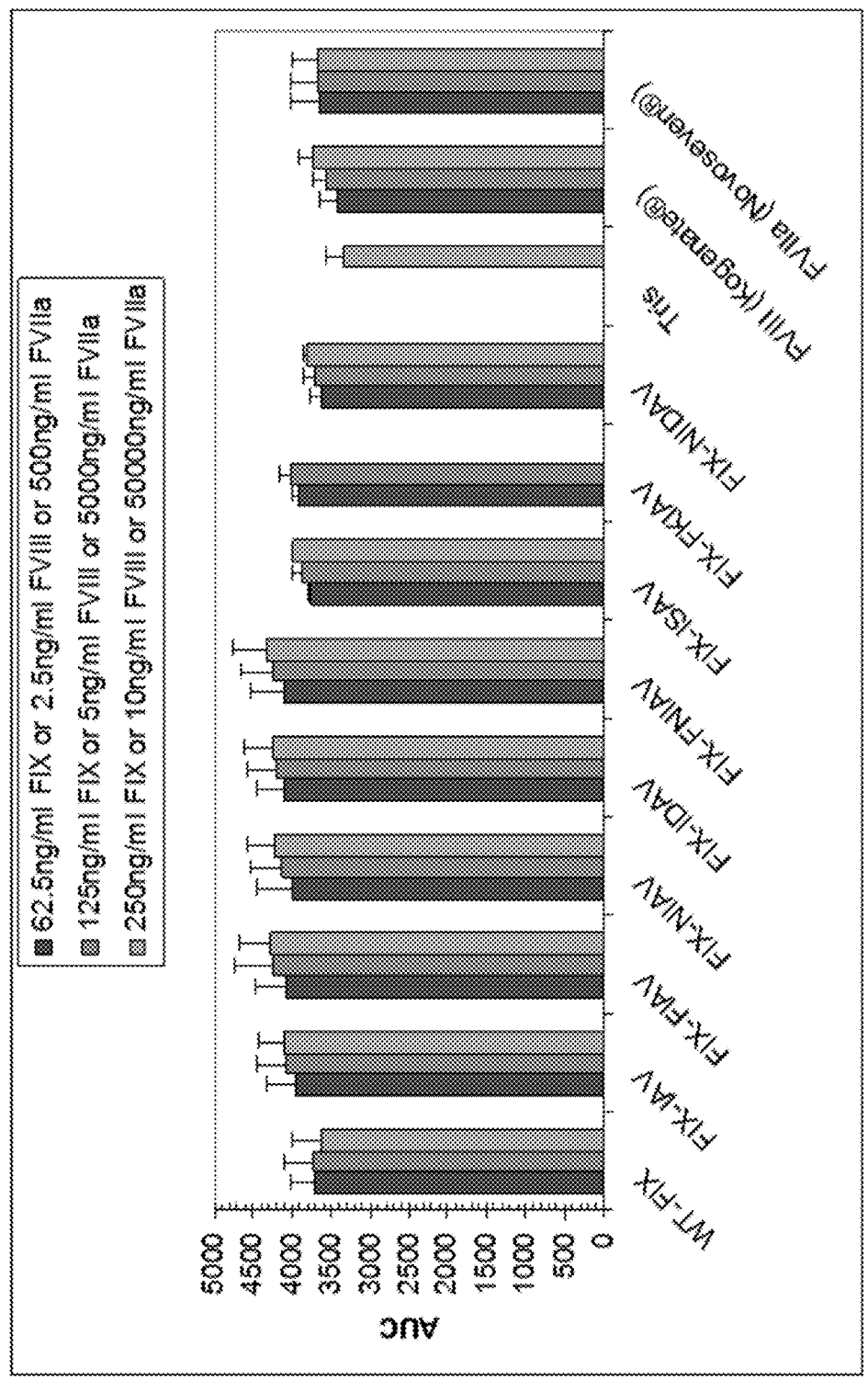
Figure 3E:
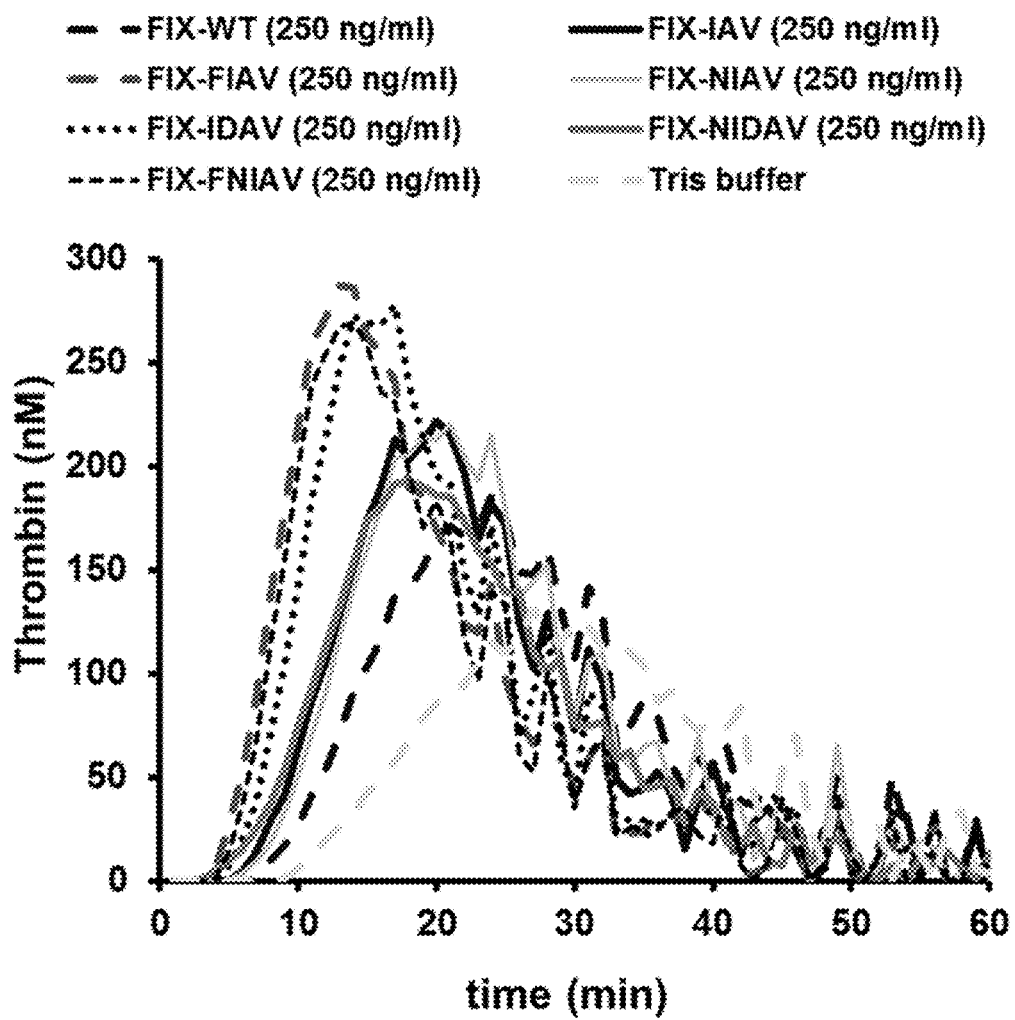
Figure 4A:
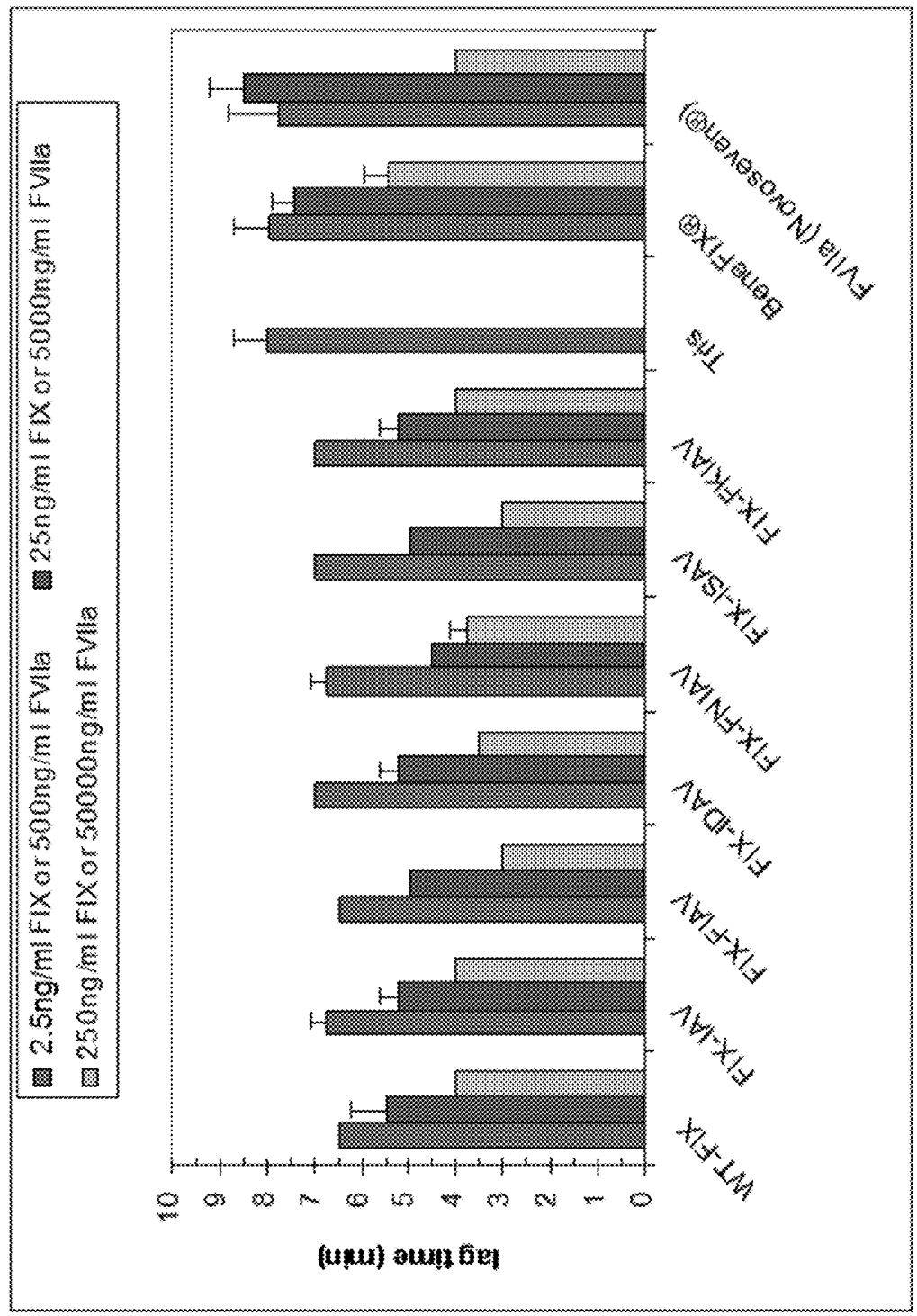
FIGS. 4A-4E TGA of F.IX variants with F.VIII-independent activity in F.IX-deficient plasma
(RD 1:100)
(4A) lag time. (4B) peak thrombin. (4C) velocity index. (4D) AUC. (4E) Representative graph.
Figure 4B:
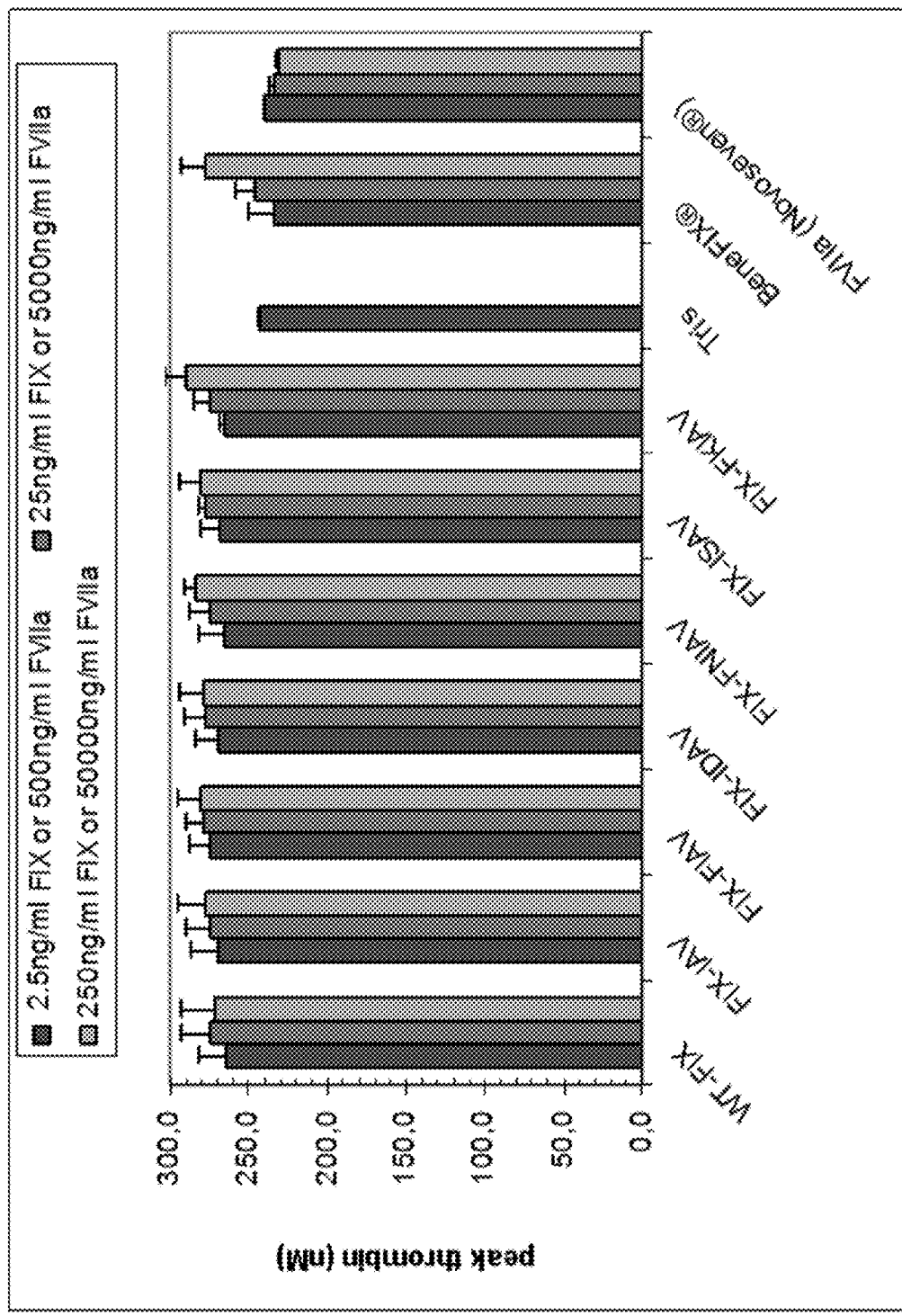
Figure 4C:
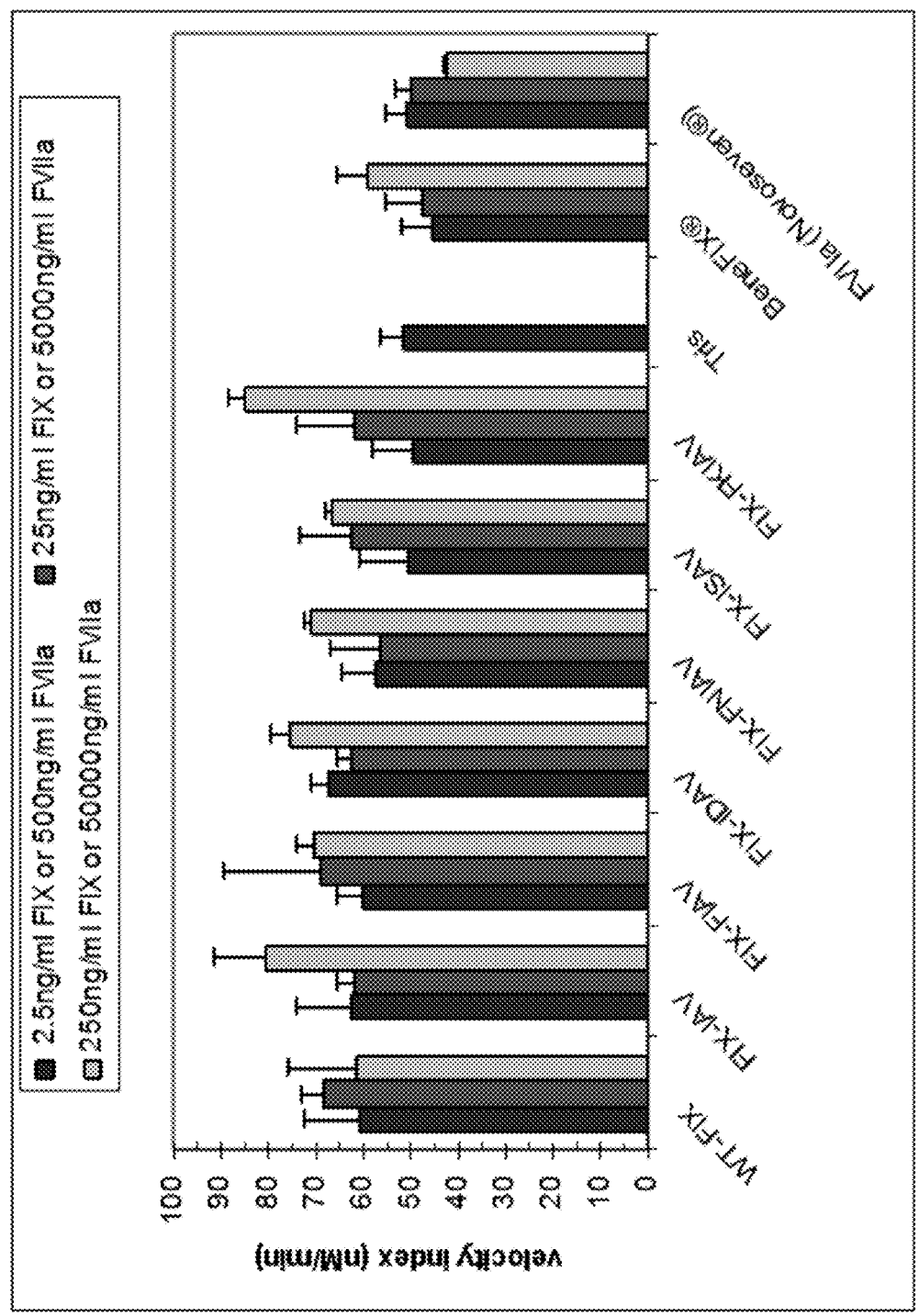
Figure 4D:
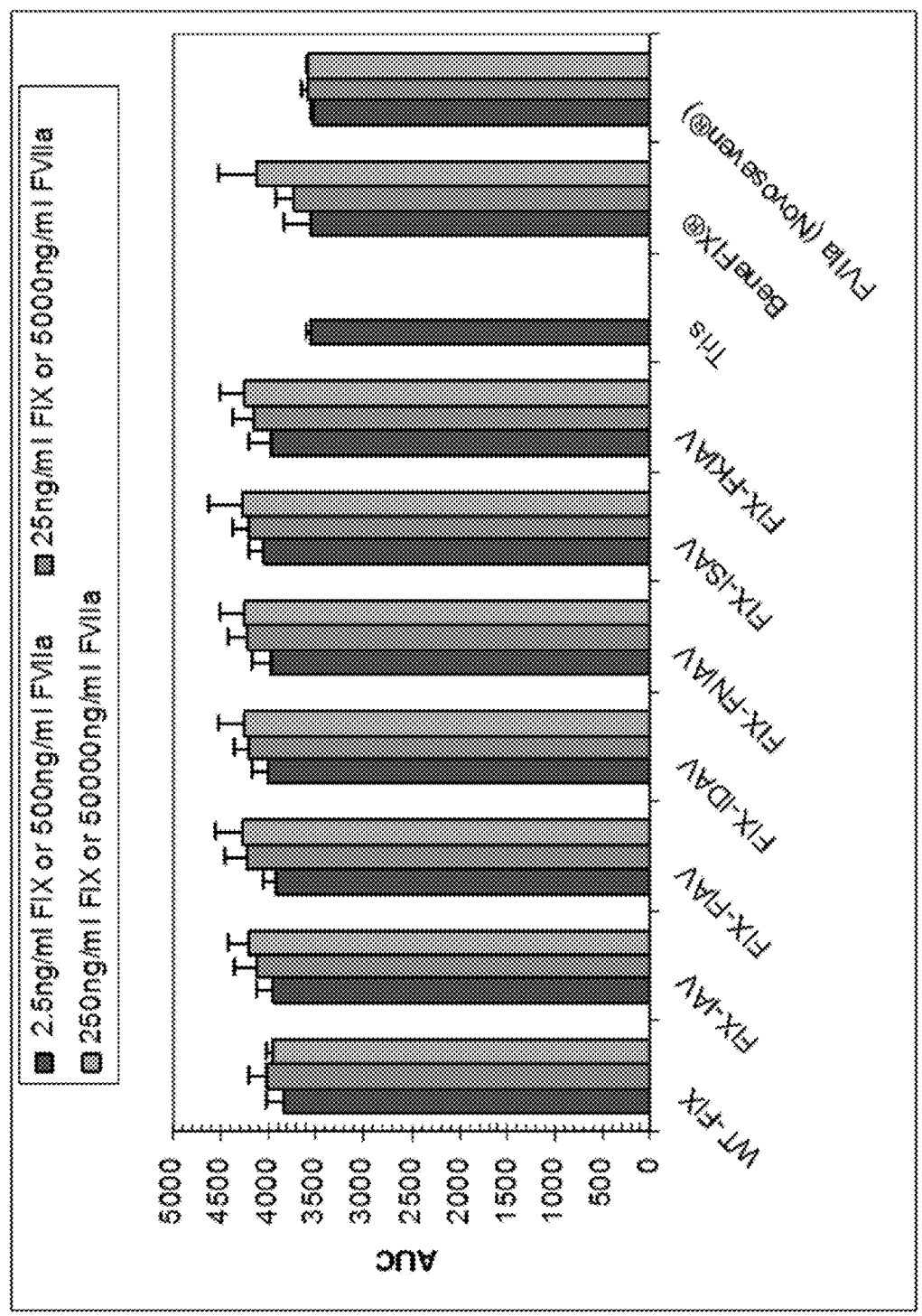
Figure 4E:
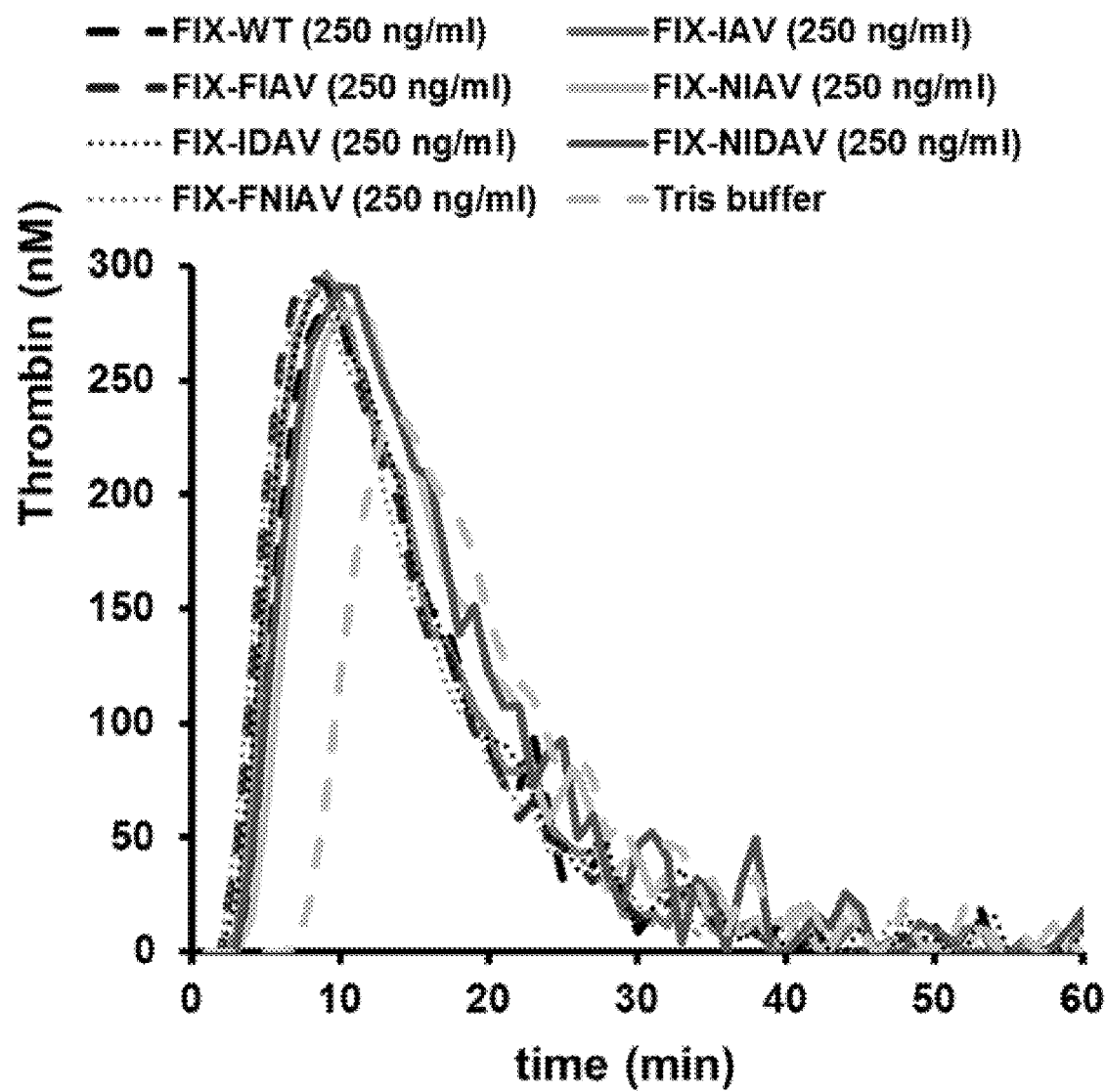
Figure 5A:
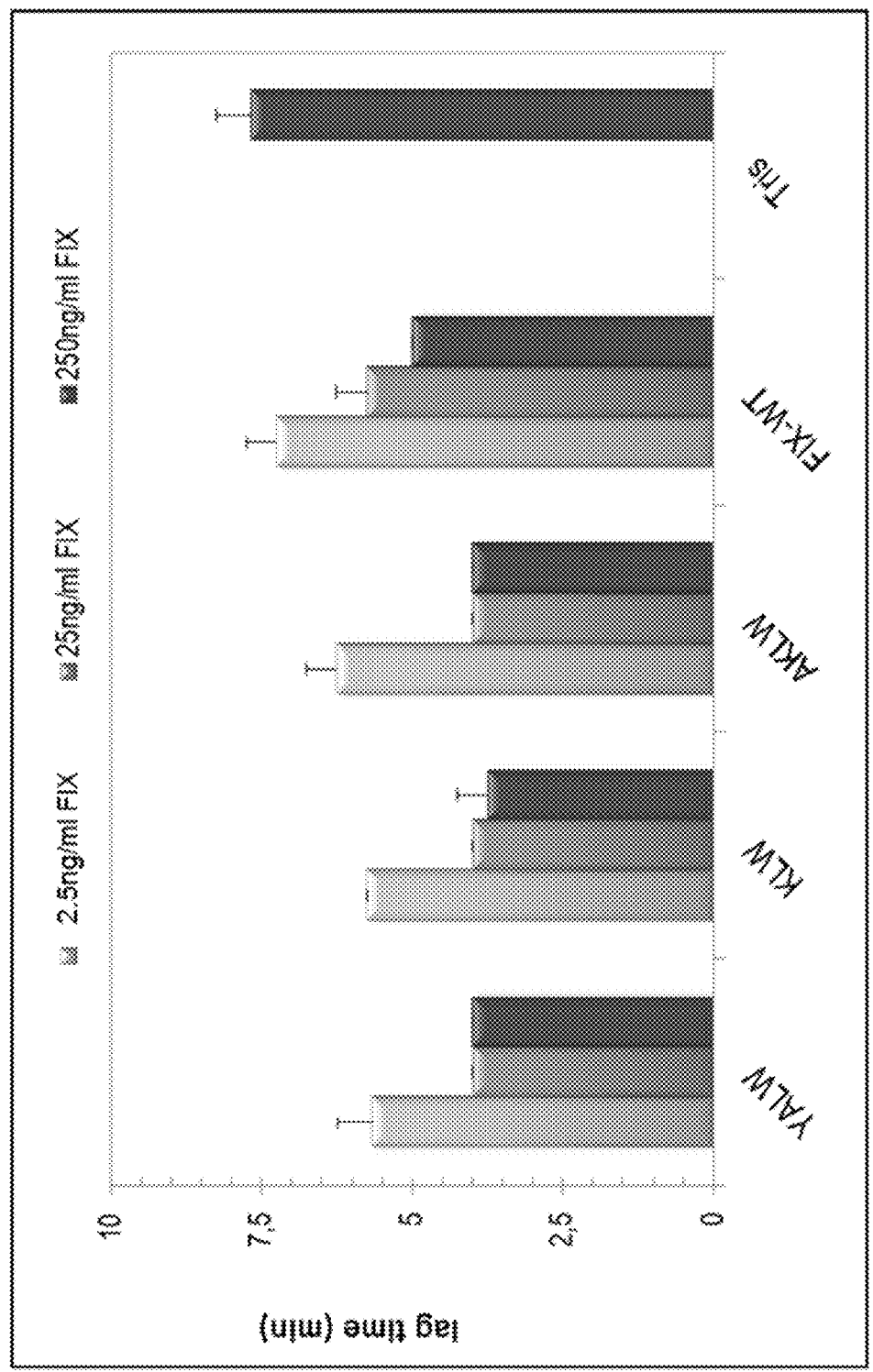
FIGS. 5A-5E TGA of F.IX variants with hyperfunctional F.IX activity in F.IX-deficient plasma
(RD 1:100)
(5A) lag time. (5B) peak thrombin. (5C) velocity index. (5D) AUC. (5E) Representative graph.
Figure 5B:
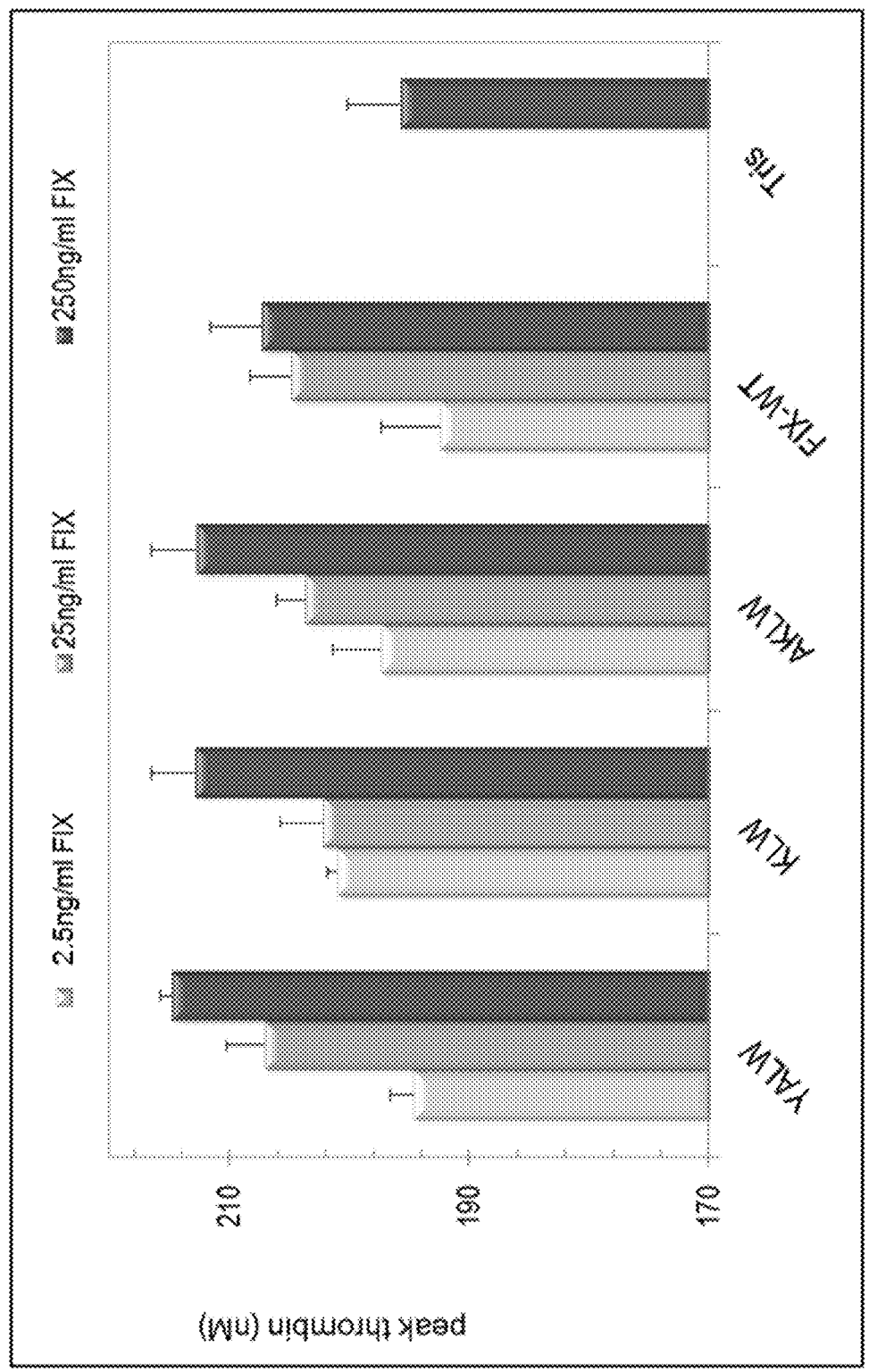
Figure 5C:
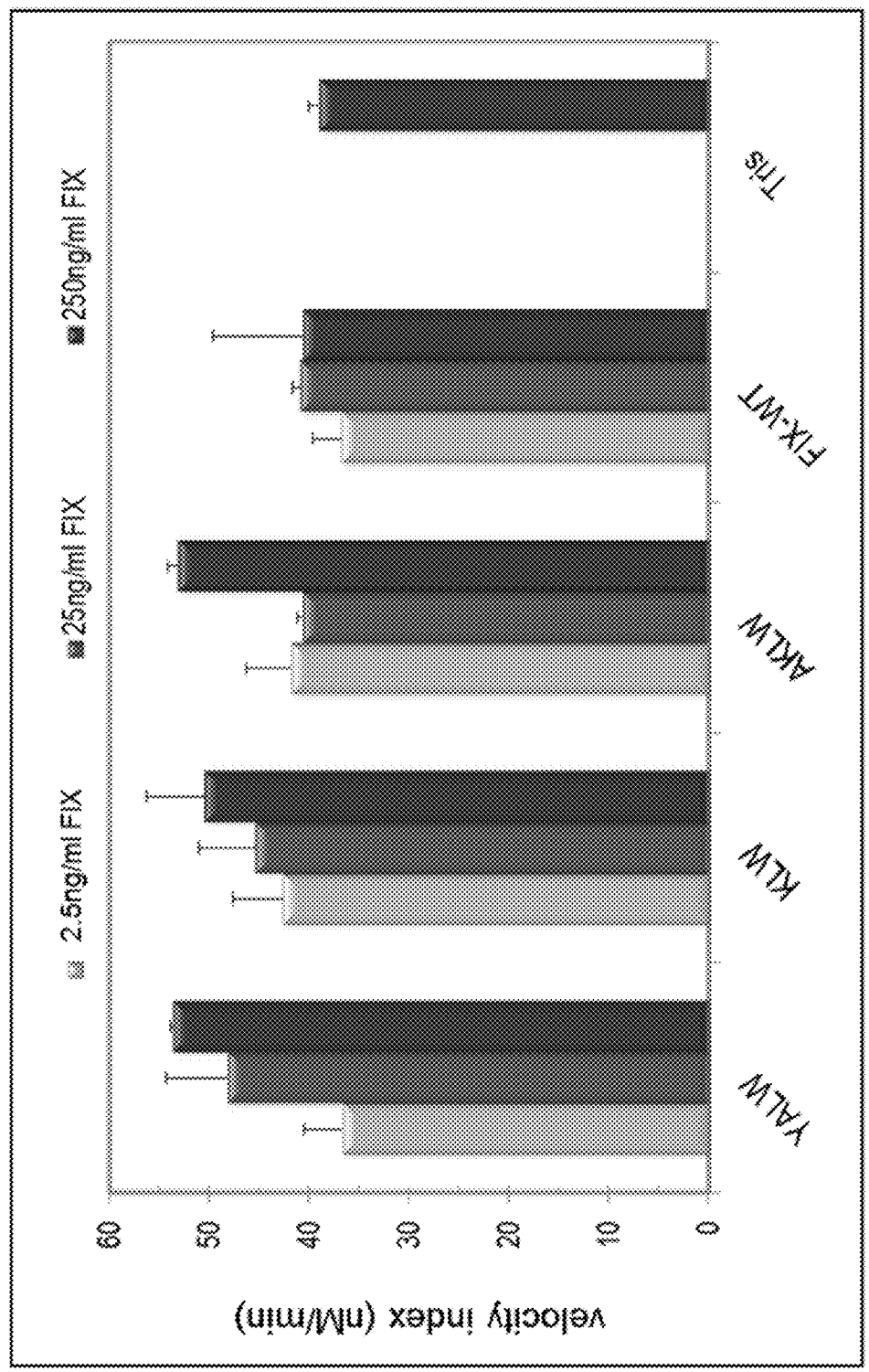
Figure 5D:
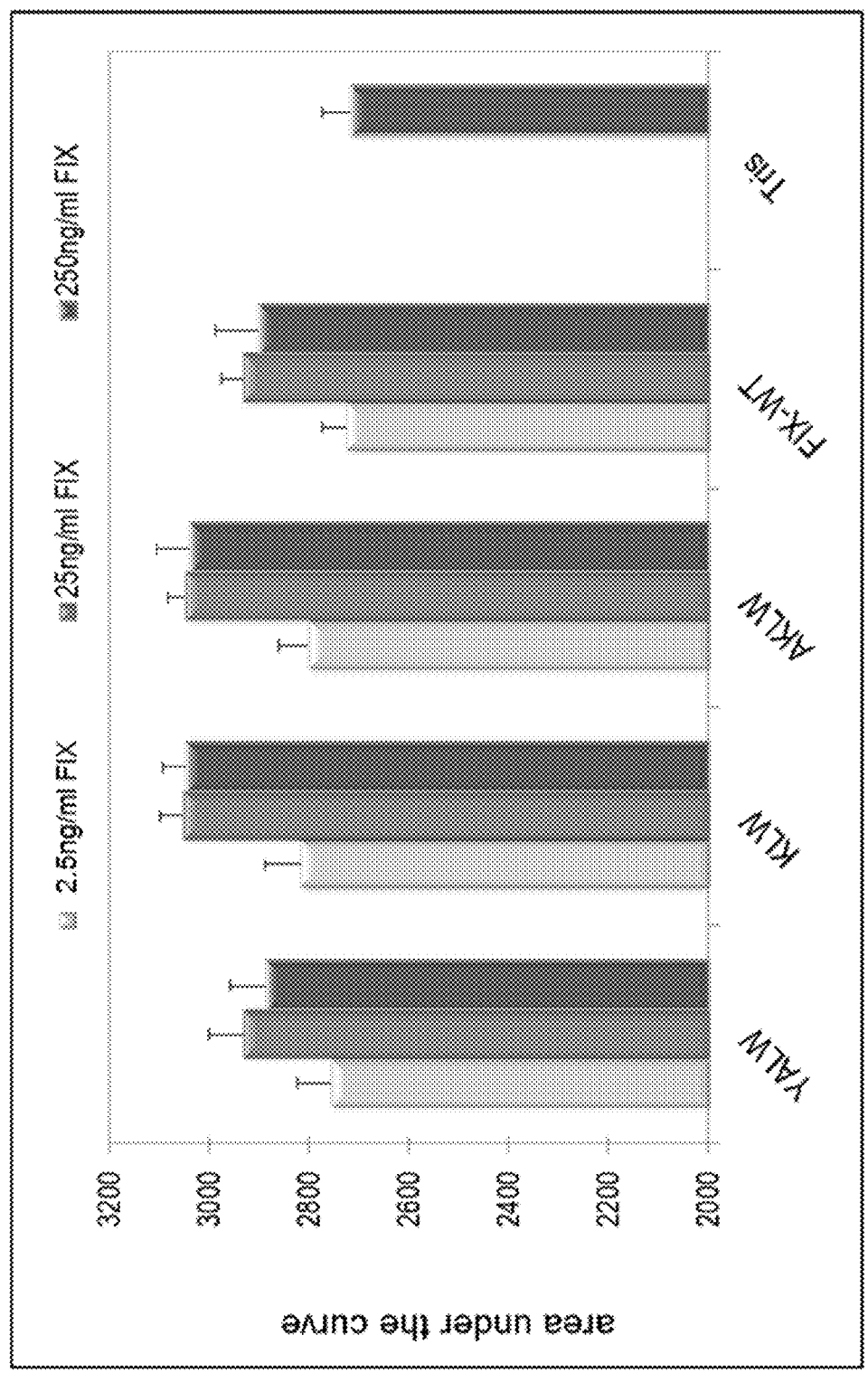
Figure 5E:
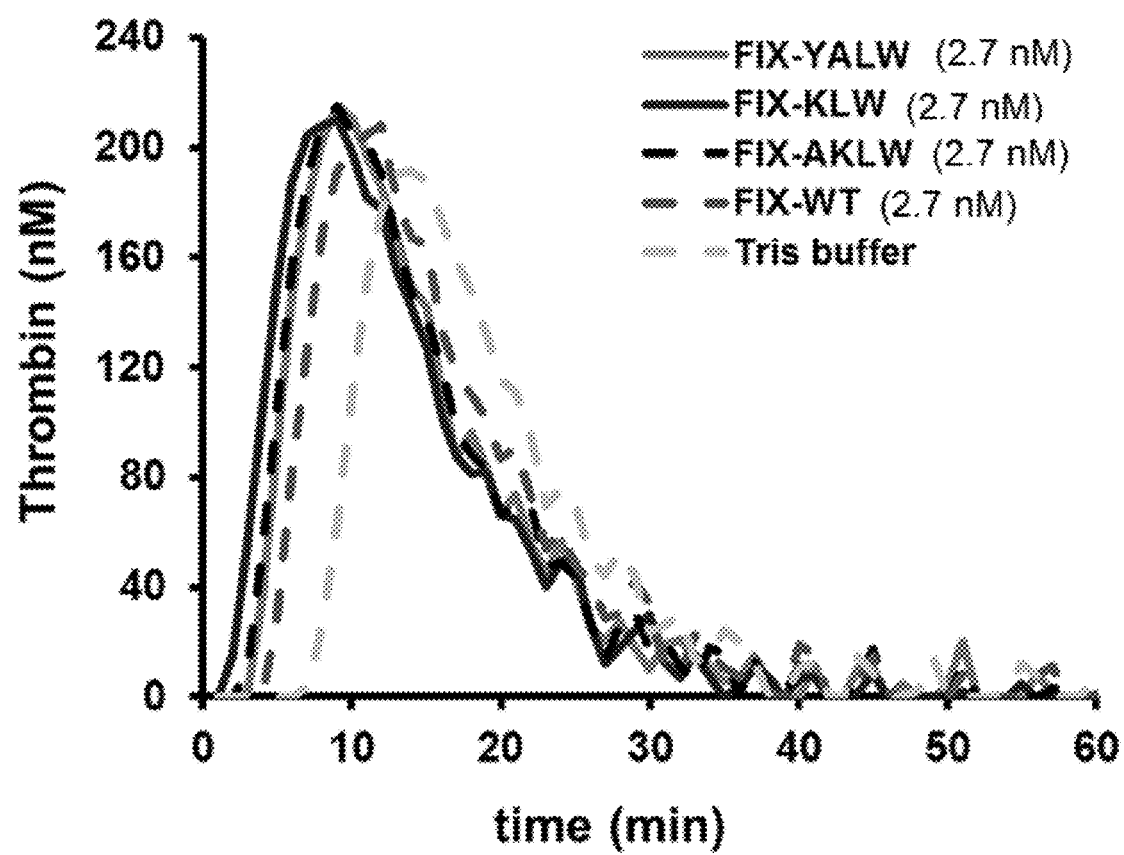
Figure 6A:
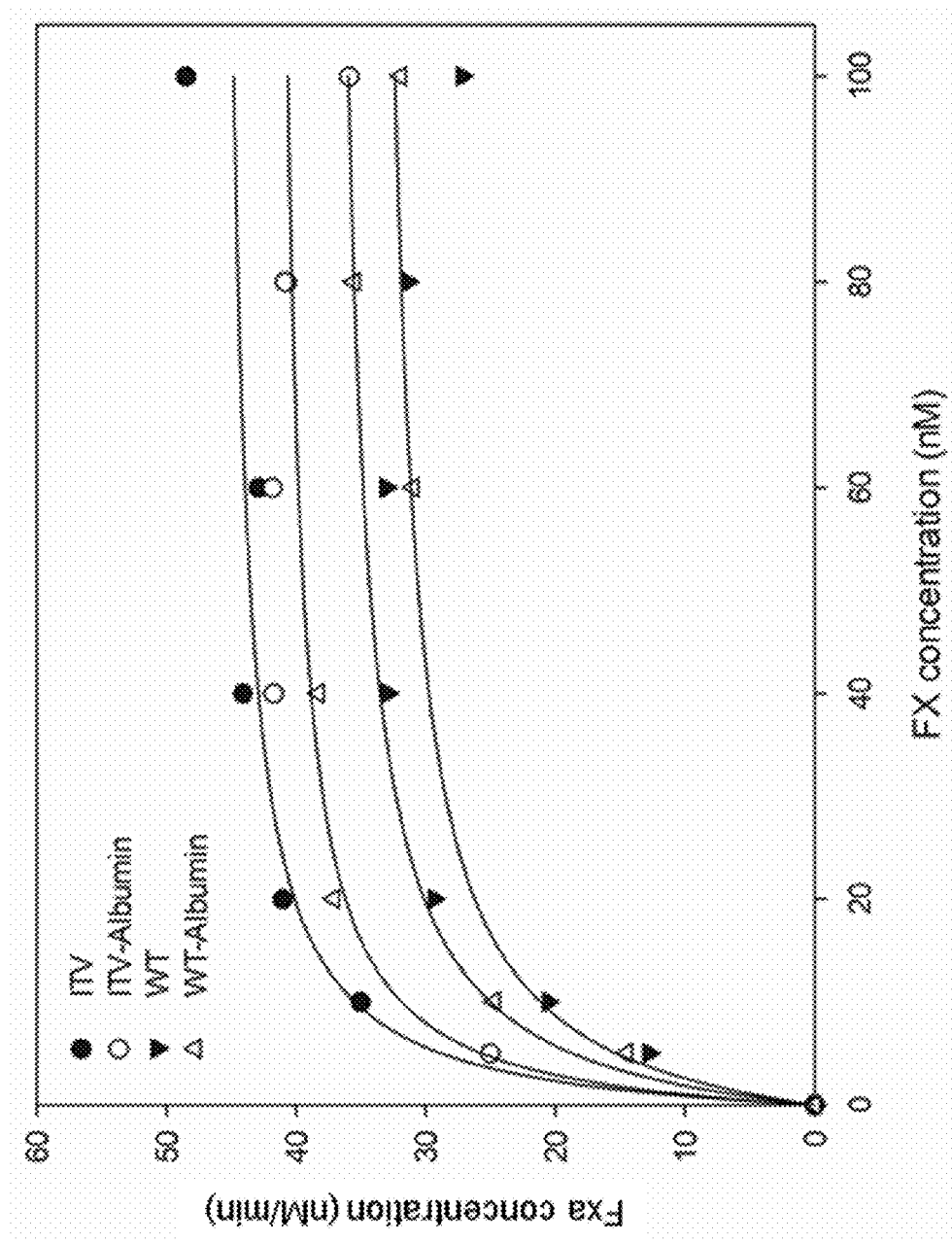
FIGS. 6A-6E F.X activation of
(6A) FIX variant ITV in the presence of F.VIII,
(6B) FIX variant ITV in the absence of F.VIII,
(6C) FIX variants with F.VIII-independent activity in the presence of F.VIII,
(6D) FIX variants with F.VIII-independent activity in the absence of F.VIII,
(6E) FIX variants with hyperfunctional F.IX activity in the presence of F.VIII.
Figure 6B:
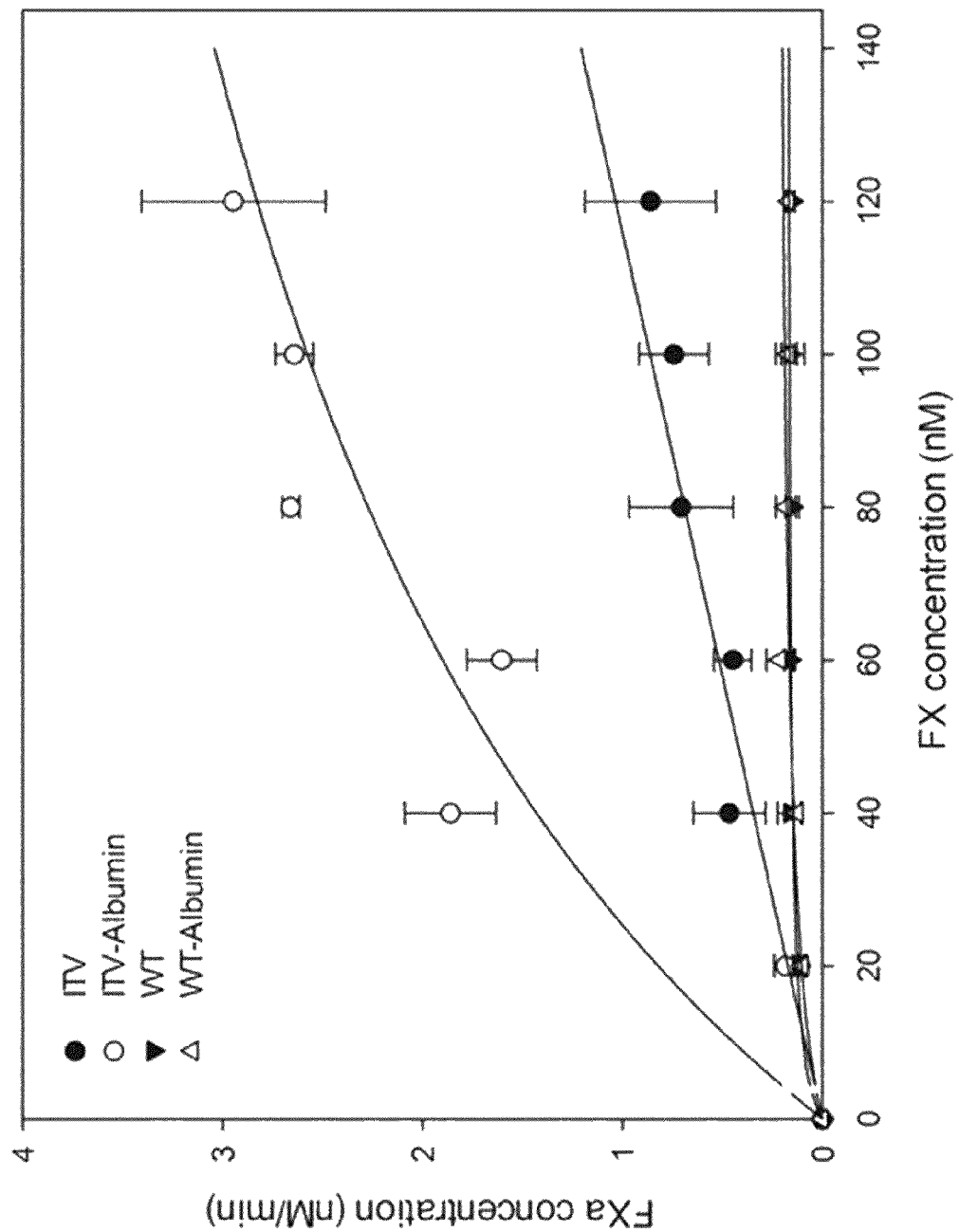
Figure 6C:
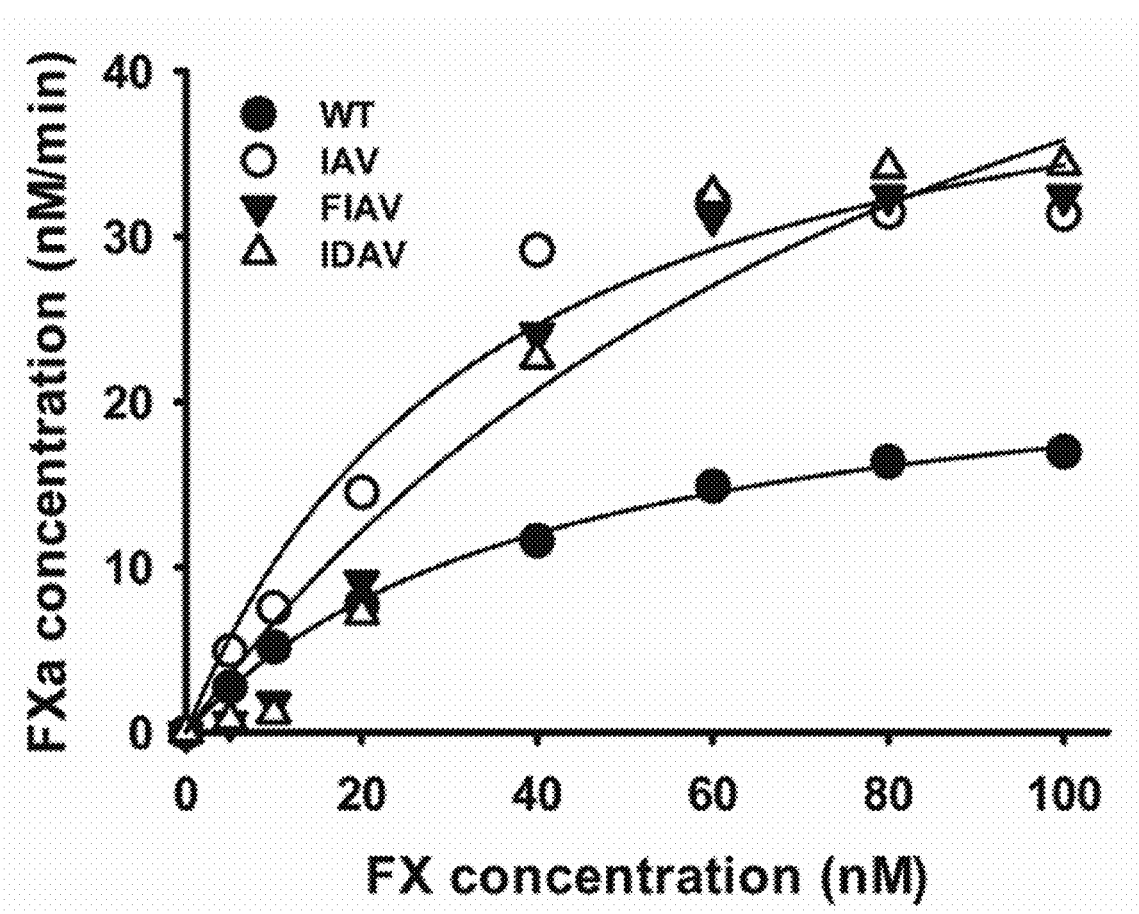
Figure 6D:
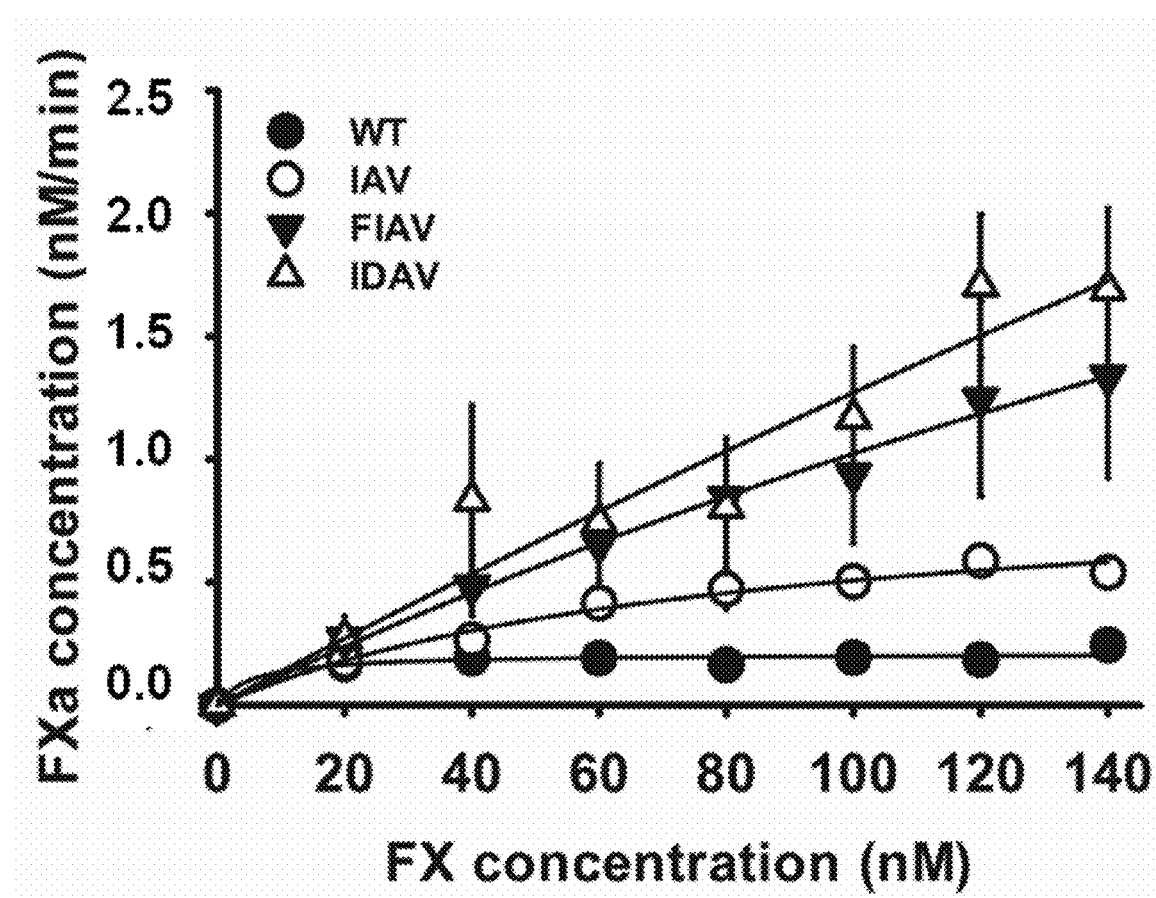
Figure 6E:
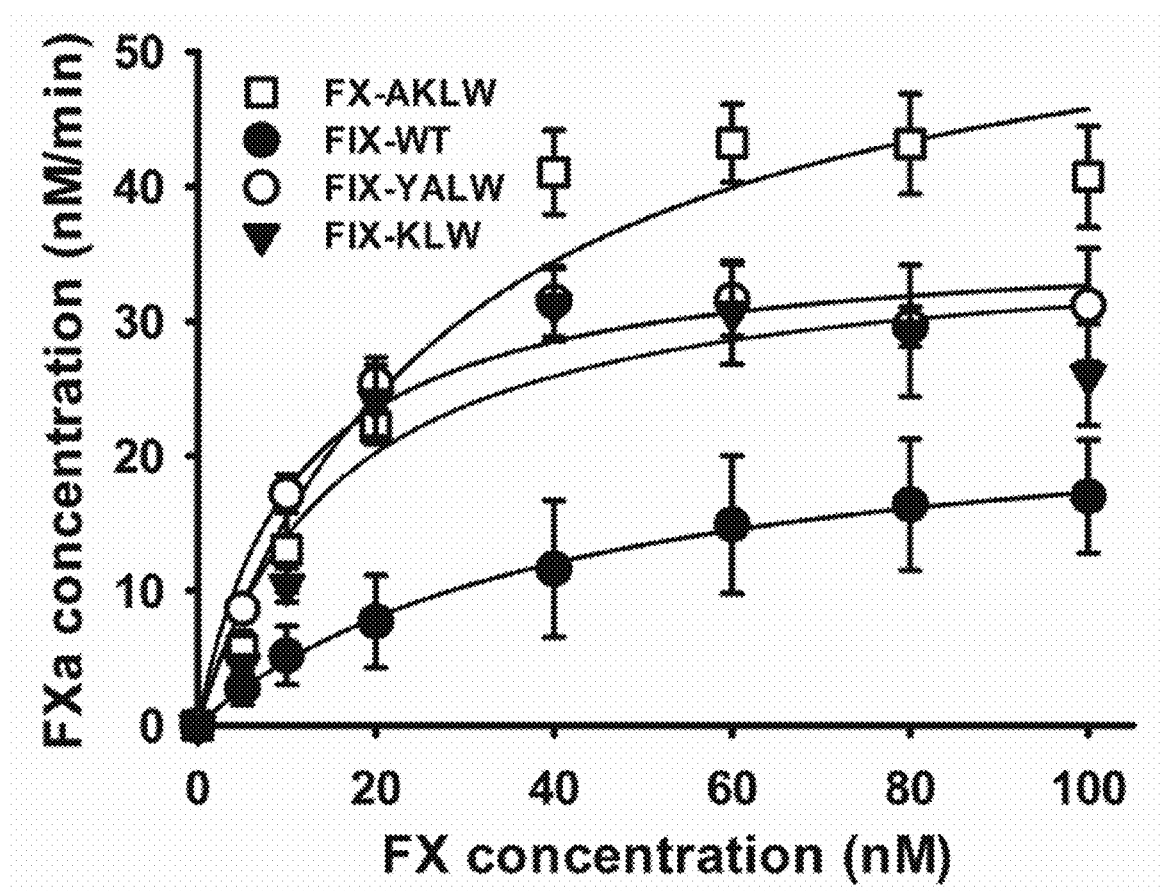
Figure 7B:
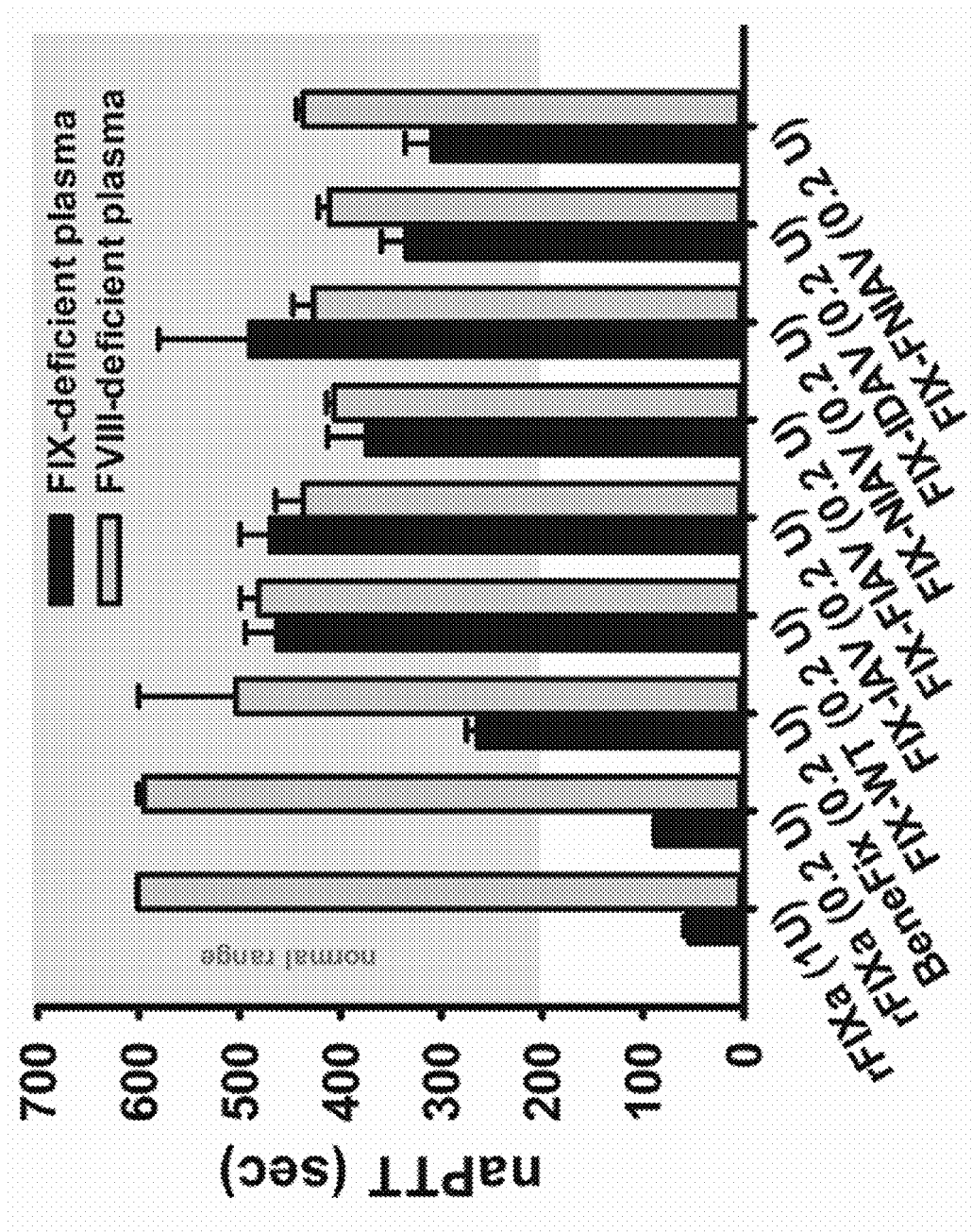
Figure 8A:
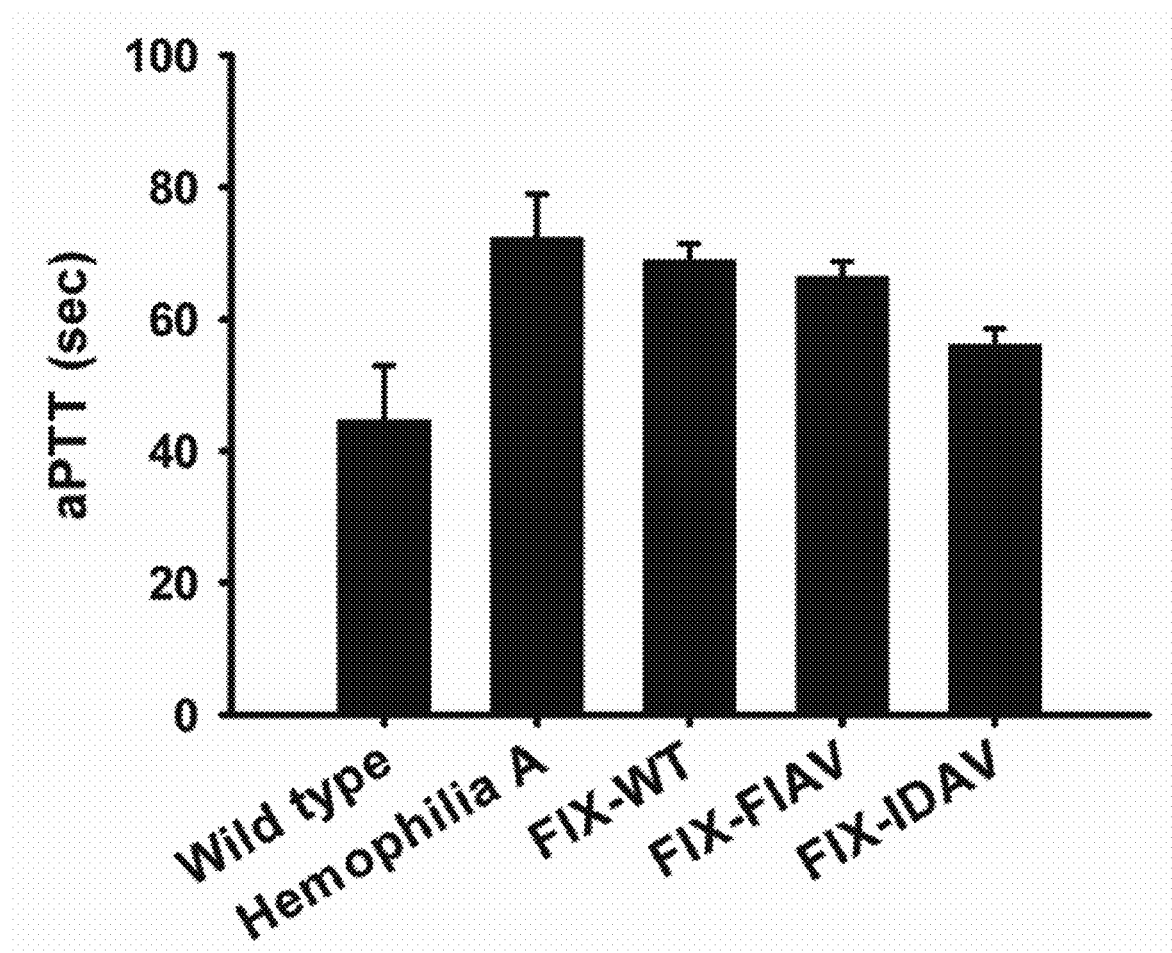
FIGS. 8A-8B In vivo efficacy of F.IX variants with F.VIII-independent activity
(8A) Clotting times in F.VIII-deficient mice after expression of F.IX variants with FVIII-independent activity.
(8B) Phenotype correction of F.VIII-deficient mice after expression of F.IX variants with FVIII-independent activity.
Figure 8B:
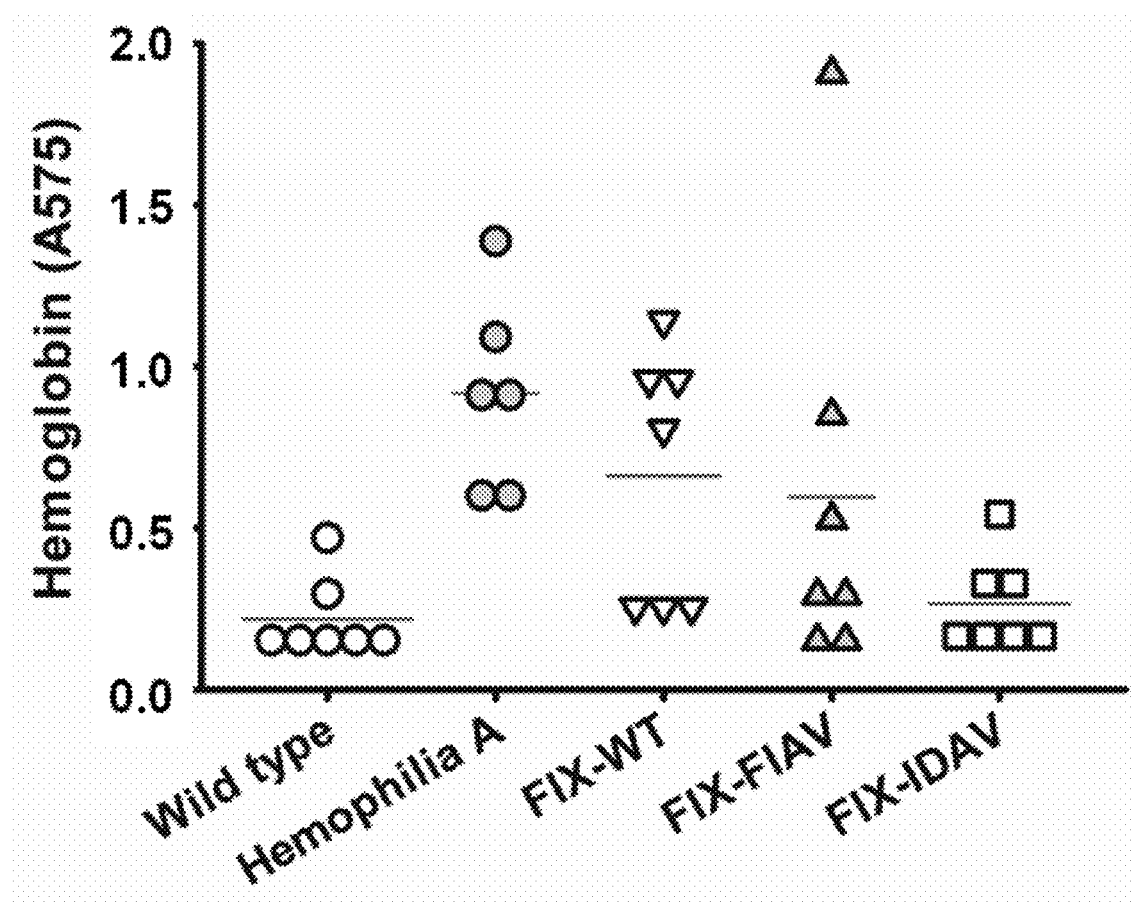

Material and Methods
Non-Viral Vectors
Plasmid pcDNA™ 3.1 (Invitrogen, Carlsbad, Calif., USA) contained a human FIX mini-gene including a 1.4 kb fragment of intron A under control of the cytomegalovirus (CMV) promoter/enhancer and a bovine growth hormone polyadenylation signal (Schuettrumpf et al., 2005). For in vivo expression, the human FIX expression cassette was introduced into the minicircle producer plasmid pMC.BE-SPX-MCS2 (System Biosciences) and controlled by the strong liver-specific enhancer/promoter HCR/hAAT (hepatic locus control region 1/human α-1-antitrypsin). Nucleotide substitutions were introduced in the hFIX cDNA using the QuickChange II XL site-directed mutagenesis kit (Agilent technologies) and confirmed by sequencing.

Random Screening for FIX Muteins

Random mutations were introduced into the hFIX expression cassette of pcDNA™ 3.1 possessing already the substitutions V181I, K265T and I383V (named FIX-ITV; Milanov et al., 2012) by the GeneMorph II EZClone Domain Mutagenesis Kit (Agilent technologies) as described by the manufacturer. Megaprimer synthesis was performed using

```
forward
                                         [SEQ ID NO. 3]
5' TCTGAATCGGCCAAAGAGG '3
and reverse
                                         [SEQ ID NO. 4]
5' CAGTTGACATACCGGGATACC '3
primers
``` which tense over exon 2 to 8 of hFIX cDNA amplifying a 1.2 kb fragment. Initial amount of target DNA was set to 750 ng to get a mutation frequency of 2.7 per 1 kb. Plasmid DNA was extracted from each individual transformed E. coli colony (total number: 1600) using the QIAprep 96 Turbo Miniprep Kit (Qiagen). HEK 293T cells were transfected with 2.5 µg plasmid DNA encoding FIX-WT, FIX-ITV or individual variant by lipofection (Lipofectamine; Invitrogen) in 96-well-plates, initial cell density was $5 \times 10^4$ cells/well. Protein expression in OptiMem medium supplemented with 10 µg/ml vitamin K was performed for 48 h. Collected supernatants of each variant were assayed for FIX- and FVIII-bypassing activity using a commercially available chromogenic assay (Biophen Faktor IX; Hyphen BioMed) with minor modifications in the presence and absence of FVIII, respectively. Normal human plasma (Control Plasma N; Siemens) was used for a standard curve and the engineered variant FIX-ITV was used as gold standard for comparison of activity levels. Promising variants/clones were sequenced to identify specific amino acids substitutions responsible for activity increase.

Recombinant Protein Production

HEK 293T cells were cultured in DMEM supplemented with 10% FBS, 1% Pen/Strep and 1% L-glutamine and plated 24 h prior to transfection into 6-well-plates with an initial cell density of $1 \times 10^6$ cells/well. For transient expression, cells were transfected with 15 µg of CMV-hFIX pcDNA™ 3.1 plasmids using the calcium phosphate-mediated precipitation method. Protein expression was performed in serum- and antibiotic-free Opti-MEM containing 10 µg/ml vitamin K. Supernatants were collected 24 h post-transfection and assayed for FIX activity, ELISA, kinetic parameters and thrombin generation.

Clotting Activity Assay and FIX Antigen

Clotting activity was determined by a modified one-stage activated partial thromboplastin time (aPTT) and nonactivated aPTT (naPTT) assay in FIX- or FVIII-deficient plasma, as described previously (Milanov et al., 2012). FIX specific activity was calculated by dividing the clotting activity by the antigen levels and normalized to wild type protein (set as 100%). FIX antigen levels were determined by ELISA as described (Schuettrumpf et al., 2005).

Thrombin Generation Assay

Thrombin generation was measured with a commercial assay (Technothrombin TGA; Technoclone) according to manufacturer's instructions. TGA RD buffer was used at a final dilution of 1:20 or 1:100 in FVIII- or FIX-deficient plasma, respectively. Final concentration of FIX protein was 0.05% to 5% of normal plasma levels, diluted in TGA buffer (Technoclone). Preparations of rhFIX (BeneFIX; Pfizer) or rhFVIII (Kogenate; Bayer) were used as controls. Analysis of thrombin generation was evaluated by the provided Technothrombin TGA evaluation software.

FX Activation by FIXa in the Presence or Absence of FVIIIa

FIX protein samples were activated to FIXa by activated FXI (Haematologic Technologies) in the presence of 5 mM $CaCl_2$ at a molar enzyme/substrate ratio of 1:100 for 5 h at room temperature. Then, FXIa was removed by affinity-purified goat anti-FXI IgG (Haemachromdiagnostica) coupled to Protein G coated magnetic beads (Dynabeads protein G; Invitrogen). FX activation was performed in the presence of 10 nM rhFVIII (Kogenate®; Bayer) and 1 nM FIX or in the absence of FVIII with 4 nM FIX, as described (7). The reaction was measured at 405 nm in 1-min intervals for 10 min at 37° C. in a microtiter plate reader. Absorbance values were converted into molar concentrations using a molar extinction coefficient of 9600 $M^{-1}$ $cm^{-1}$ for pNA and a path length of 0.5 cm for a total volume of 100 µl. Kinetic parameters were calculated by SigmaPlot version 12.0 following the Michaelis-Menten equation.

Animal Procedures

All animal procedures were approved by the local animal care, protection and use authorities (Regierungspräsidium Darmstadt). C57Bl/6 mice were purchased from Harlan Laboratories. FXIII-deficient mice containing a disruption in exon 16 of the FVIII gene were obtained from Charles River Laboratories. Mice were 9-12 weeks old at the onset of experiments. For liver-directed gene transfer, the non-viral vector MC.HCR/hAAT. FIX encoding FIX-WT or variant was administered hydrodynamically into the tail vein with a vector dose of 25 µg per mouse, as described previously (Milanov et al., 2012). Three days after injection blood samples were taken from the retro-orbital plexus. Tail-clip bleeding assay was performed as previously described (Milanov et al., 2012) and quantified by measuring the absorbance of hemoglobin at 575 nm. TAT complexes were measured by ELISA (Enzygnost TAT; Siemens) according to the manufacturer's instructions.

Statistics

Statistical evaluation of data was performed by analysis of variance (ANOVA) using SigmaPlot version 12.0 (Systat software Inc., San Jose, USA).

Results

To further improve the properties of the ITV and the IAV variant, the inventors introduced further mutations in order to generate F.IX molecules with different properties.

Tables 1 to 4 show the tested mutations and the activity of the variants in F.VIII.- or F.IX-deficient plasma.

TABLE 1

Clotting activities of factor IX variants showing a F.VIII-independent activity generated by random mutagenesis measured by a F.IX chromogenic assay in absence and presence of F.VIII. Values are shown relative to either wild type factor IX (WT-F.IX) or ITV. WT-F.IX refers to V181/K265/I383 and ITV refers to V181I/K265T/I383V. Standard deviation (S.D.).

| Variants | Activity without F.VIII relative to ITV | SD | Activity with F.VIII relative to WT-FIX | SD |
|---|---|---|---|---|
| WT-FIX | 0.38 | 0.07 | 1.00 | 0.32 |
| ITV | 1.00 | 0.028 | 0.73 | 0.27 |
| Single exchange | | | | |
| ITV + L336H | 0.72 | 0.45 | 0 | 0 |
| ITV + D154N | 1.09 | 0.89 | 0.34 | 0.08 |
| ITV + S102N | 1.07 | 0.18 | 0.65 | 0.28 |
| ITV + Q11R | 1.48 | 0.11 | 1.35 | 0.24 |
| ITV + E185D | 0.61 | 0.44 | 1 | 0.42 |
| ITV + I251V | 0.77 | 0.21 | 0.6 | 0.05 |
| ITV + F25V | 0.72 | 0.15 | 0.06 | 0.04 |
| ITV + V211I | 1.04 | 0.09 | 0.58 | 0.31 |
| ITV + F75V | 0.6 | 0.01 | 0.53 | 0.32 |
| ITV + V135A | 0.98 | 0.06 | 0.9 | 0.35 |
| ITV + K394 | 0.6 | 0.1 | 0.38 | 0.19 |
| ITV + Q44H | 1 | 0.01 | 0.85 | 0.65 |
| ITV + E243D | 0.84 | 0.35 | 1.25 | 1.58 |
| Double exchange | | | | |
| ITV + N89D + F302Y | 0.94 | 0.28 | 0.09 | 0.01 |
| ITV + E113V + G310R | 0.66 | 0.43 | 0.03 | 0.05 |
| ITV + L6F + W72R | 1.41 | 0.15 | 0.98 | 0.03 |
| ITV + N54D + Q139E | 1.46 | 0.87 | 0.63 | 0.18 |
| ITV + K392E + T399S | 1.11 | 0.83 | 0 | 0.16 |
| ITV + E125D + A219V | 0.83 | 0.23 | 0 | 0.01 |
| ITV + A262D + P368I | 2.75 | 1.61 | 0.62 | 0.79 |
| ITV + H268D + A334S | 1.12 | 1.06 | 0 | 0.19 |
| ITV + N105S + I383A | 0.2 | 0.05 | 0 | 0.05 |
| ITV + E224G + I263S | 1.05 | 0.27 | 0.55 | 0.03 |
| Triple exchange | | | | |
| ITV + V196I + C289R + G366R | 1.41 | 0.36 | 0.94 | 0.08 |
| ITV + C222Y + S304F + T386A | 0.96 | 0.54 | 0.09 | 0.06 |
| ITV + N260K + F299T + L330I | 1.24 | 1.54 | 0 | 0.01 |
| Quadruple exchange | | | | |
| ITV + K122R + R338E + I383A + T376A | 0.41 | 0.21 | 0.55 | 0.18 |
| ITV + Q195L + H236L + K319R + M391K | 1.58 | 1.22 | 0.18 | 0.22 |
| ITV + V86A + A262D + E119V + P368S | 0.88 | 0.23 | 0.09 | 0.12 |

TABLE 2

Clotting activities of factor IX variants generated by random mutagenesis measured by a F.IX chromogenic assay in presence of F.VIII. Values are shown relative to either wild type factor IX (WT-F.IX) or ITV. WT-F.IX refers to V181/K265/I383 and ITV refers to V181I/K265T/I383V. Standard deviation (S.D.).

| Variants | Activity with F.VIII relative to WT-FIX | SD |
|---|---|---|
| WT-FIX | 1.00 | 0.32 |
| ITV | 0.73 | 0.27 |
| Single exchange | | |
| ITV + E243D | 1.25 | 1.58 |
| ITV + T159S | 1.17 | 0.5 |
| ITV + Q11R | 1.35 | 0.24 |
| ITV + E185D | 1 | 0.42 |
| ITV + V135A | 0.9 | 0.35 |
| ITV + Q44H | 0.85 | 0.65 |
| Double exchange | | |
| ITV + L6F + W72R | 0.98 | 0.03 |
| ITV + E78D + D186E | 1.2 | 0.6 |
| ITV + A262D + P368I | 0.62 | 0.79 |
| ITV + E224G + I263S | 0.55 | 0.03 |
| Quadruple exchange | | |
| ITV + K122R + R338E + I383A T376A | 0.55 | 0.18 |
| ITV + T159S + H243R + N367D + R327S | 0.54 | 0.91 |

TABLE 3

Clotting activities of factor IX variants with single exchange showing a FVIII-independent activity measured by one stage aPTT in absence and presence of F.VIII. Values are shown in percent, being 100% the activity of wild type factor IX in normal human pool plasma with normal human levels of both F.IX and F.VIII. Standard error of mean (S.E.M.).

| Variants | Activity without F.VIII (%) | S.E.M. | Activity with F.VIII (%) | S.E.M. |
|---|---|---|---|---|
| WT-FIX | 1 | 0 | 100 | 7 |
| V181I + K265A + I383V (ITV) | 8.5 | 1 | 264 | 21 |
| ITV + L6F | 11 | 4 | 57 | 5 |
| ITV + W72R | 11 | 4 | 57 | 5 |
| ITV + N89D | 11 | 0 | 202 | 18 |
| ITV + S102N | 11 | 2 | 345 | 34 |
| ITV + N105S | 14 | 1 | 212 | 18 |
| ITV + K122R | 12 | 4 | 2083 | 197 |
| ITV + E185D | 9 | 3 | 300 | 44 |
| ITV + F302Y | 11 | 0 | 202 | 18 |
| ITV + R338E | 12 | 4 | 2083 | 197 |
| ITV + T376A | 12 | 4 | 2083 | 197 |

TABLE 4

Clotting activities of factor IX variants with multiple amino acid substitutions including substitution in the 99-loop of FIX in absence and presence of F.VIII measured by a one stage aPTT. Values are shown in percent, being 100% the activity of wild type factor IX in normal human pool plasma with normal human levels of both F.IX and F.VIII. Standard error of mean (S.E.M.).

| Variants | Activity (%) Without F.VIII | S.E.M. | Activity (%) With F.VIII | S.E.M. |
|---|---|---|---|---|
| Wild type | 0.85 | 0.07 | 102 | 5 |
| V181I + K265A + I383V (IAV) | 11.15 | 1.17 | 140 | 9 |
| IAV + L6F | 11.48 | 1.29 | 185 | 17 |
| IAV + W72R | 11.88 | 2.99 | 255 | 46 |
| IAV + S102N | 13.2 | 0.99 | 277 | 57 |
| IAV + K122R | 10.26 | 0.66 | 163 | 11 |
| IAV + E185D | 15.16 | 2.01 | 228 | 20 |
| IAV + E185F | 17.44 | 5.24 | 271 | 28 |
| IAV + E185K | 11.47 | 2.82 | 161.29 | 74 |
| IAV + E185Q | 16.57 | 4.62 | 233 | 4 |

TABLE 4-continued

Clotting activities of factor IX variants with multiple amino acid substitutions including substitution in the 99-loop of FIX in absence and presence of F.VIII measured by a one stage aPTT. Values are shown in percent, being 100% the activity of wild type factor IX in normal human pool plasma with normal levels of both F.IX and F.VIII. Standard error of mean (S.E.M.).

| Variants | Activity (%) Without F.VIII | S.E.M. | Activity (%) With F.VIII | S.E.M. |
|---|---|---|---|---|
| IAV + E185S | 17.10 | 4.17 | 181 | 60 |
| IAV + I263S | 11.90 | 1.16 | 244 | 26 |
| IAV + L6F + S102K | 13.02 | 1.18 | 361 | 41 |
| IAV + L6F + S102N | 14.27 | 0.82 | 219 | 46 |
| IAV + L6F + S102P | 14.72 | 2.18 | 237 | 49 |
| IAV + S102N + E185D | 14.05 | 0.85 | 266 | 10 |
| IAV + S102N + E185F | 8.6 | 0.89 | 312 | 24 |
| IAV + S102N + E185K | 6.42 | 0.25 | 204 | 44 |
| IAV + S102N + E185S | 9.11 | 0.99 | 392 | 37 |
| IAV + L6F + I263S | 13.57 | 0.57 | 311 | 9 |
| IAV + E185D + I263S | 10.38 | 0.96 | 166 | 5 |

Figure 9A:
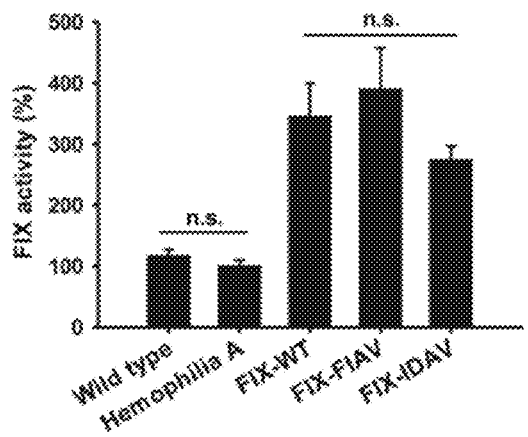
FIGS. 9A-9D In vivo efficacy of FIX variants with FVIII-independent activity in F.VIII-Knockout mice following hydrodynamic injection of 25 μg liver-directed minicircle vector encoding for FIX-WT (n=7), FIX-FIAV (n=7) and FIX-IDAV (n=7). Control groups include wild-type mice (n=7) and naïve mice (n=6).
F.IX activity (9A) and F.VIII-independent activity (9B) measured by one-stage coagulation assay in human F.IX- or F.VIII-deficient plasma, respectively, were analyzed three days post-injection.
(9C) Blood loss after tail dissection at 1.5 mm diameter terminated after 10 min.
(9D) TAT levels as a marker for hypercoagulopathy. Shown are means±SEM. *p<0.05 and ***p<0.001 according to ANOVA using Holm-Sidak test for multiple comparison with the wild type FIX group.
Figure 9B:
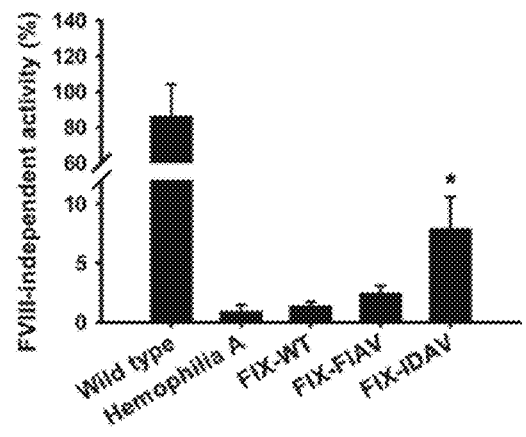
Figure 9C:
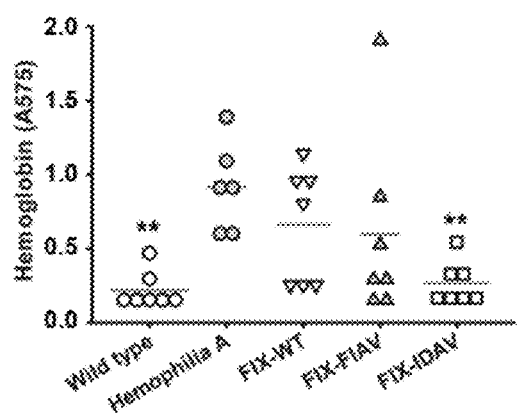
Figure 9D:
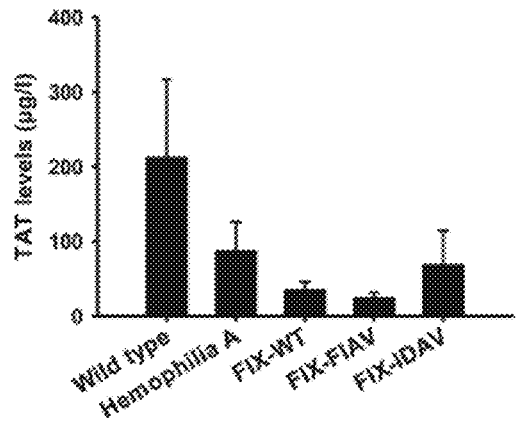

Hepatic Expression of F.IX Mutants with F.VIII-Independent Activity Provides Hemostasis in F.VIII-Knockout Mice To examine the potential of FIX mutants to improve in vivo clotting activity and correct the bleeding phenotype of HA mice, we hydrodynamically injected liver-directed mini-circles encoding FIX-WT or the variants FIX-FIAV (IAV+ L6F) or FIX-IDAV (IAV+E185D) at vector doses of 25 µg into the tail vein of FVIII-knockout mice. Three days after gene delivery, mutant FIX expression levels were similar in all treatment groups and reached plasma activity levels of around 300% of normal (FIG. 9A). Only mice treated with FIX-IDAV showed significantly shorter clotting times resulting in 10% of FVIII-independent activity when measured in FVIII-deficient plasma by one-stage aPTT assay (FIG. 9B). Nevertheless, both mutants, FIX-FIAV and -IDAV, partially corrected the hemophilic phenotype after a tail-clip bleeding assay (FIG. 9C) suggesting that low amounts of FVIII-bypassing activity are sufficient to initiate and restore the coagulation cascade. We also investigated the effect of FIX mutants on TAT complex levels, which represent a general activation marker of the coagulation system. TAT levels remained similar in all groups, albeit with high inter-individual variation (FIG. 9D).

Example 2

Material and Methods
Recombinant Protein Production and Measurement of Clotting Activity
See above, Example 1.
Thrombin Generation Assay
Thrombin generation was measured with a commercial assay (TechnothrombinTGA; Technoclone) according to manufacturer's instructions. TGA RD buffer was used at a final dilution of 1:20 or 1:100 in FVIII- or FIX-deficient plasma, respectively. Final concentration of FIX protein was 0.05% to 5% of normal plasma levels, diluted in TGA buffer (Technoclone). Preparations of rhFIX (BeneFIX; Pfizer) or rhFVIII (Kogenate; Pfizer) were used as controls. Analysis of thrombin generation was evaluated by the provided Technothrombin TGA evaluation software.
FX Activation by FIXa in Presence and Absence of FVIIIa
FIX protein samples were activated to FIXa by activated FXI (Haematologic Technologies) in presence of 5 mM $CaCl_2$ at a molar enzyme/substrate ratio of 1:100 for 5 h at room temperature. Then, FXIa was removed by affinity-purified goat anti-FXI IgG (Haemachrom diagnostica) coupled to Protein G coated magnetic beads (Dynabeads protein G; Invitrogen). FX activation was performed in the presence of 10 nM rhFVIII (Kogenate®, Bayer) and 1 nM FIX, as described (Hartmann et al., 2009). The reaction was measured at 405 nm in 1-min intervals for 10 min at 37° C. in a mircotiter plate reader. Absorbance values were converted into molar concentrations using a molar extinction coefficient of 9600 $M^{-1}$ $cm^{-1}$ for pNA and a path length of 0.5 cm for a total volume of 100 Kinetic parameters were calculated by SigmaPlot version 12.0 following the Michaelis-Menten equation.
Chitosan/DNA Nanoparticle Preparation
Nanoparticles were prepared by complex coacervation as described (Mao et al., 2001). High molecular weight chitosan with a deacetylation degree of >75% (Sigma-Aldrich) was dissolved in 50 mM NaOAc buffer to a 0.02% to 0.08% solution at pH 5.5. Chitosan and plasmid DNA solutions of 50 µg/ml or 100 µg/ml in 50 mM $Na_2SO_4$ buffer were heated separately to 55° C. Equal volumes (500 µl) of both solutions were mixed together under high-speed vortex for 30 sec. Nanoparticles were stored at room temperature until oral administration.
DNase I Protection Assay
Chitosan/DNA nanoparticles (20 µl, equivalent to 1 µg) or uncomplexed DNA (1 µg) were incubated with either 1, 100 or 300 mU of DNase I (ThermoFisher) for 1 h at 37° C. The reaction was stopped by heat-inactivation at 65° C. for 10 min in the presence of EDTA. Additional incubation with 0.8 U of chitosanase (Sigma-Aldrich) for 4 h at 37° C. released the DNA from nanoparticles. The integrity of vector DNA was examined by subsequent electrophoresis on a 0.8% agarose gel.
Animal Procedures
All animal procedures were approved by the local animal care, protection and use authorities (Regierungspräsidium Darmstadt). C57Bl/6 mice were purchased from Harlan Laboratories. FIX-deficient mice on a C57Bl/6 background (HB mice) were kindly provided by Katherine High (Children's Hospital of Philadelphia). Mice were 9-12 weeks old at the onset of experiments. For liver-directed gene transfer, the non-viral gene transfer vector MC.HCR/hAAT encoding FIX-WT or variant was administered hydrodynamically into the tail vein with a vector dose of 10 µg per mouse, as described previously (Milanov et al., 2012). For oral FIX gene delivery, mice were fed with CMV promoter driven vectors (pcDNA3.1 or MC) formulated as chitosan nanoparticles and mixed with baby cereal. Immunization of FIX-deficient mice was performed by two subcutaneous injections of 2 IU of rhFIX protein (BeneFIX®; Pfizer) in the presence of incomplete Freund's adjuvant at intervals of 2 weeks. Blood was taken from the retro-orbital plexus under isoflurane anesthesia into 1/10 volume of 3.8% sodium citrate buffer. Tail-clip bleeding assay was performed as previously described (Milanov et al., 2012) and quantified by measuring the absorbance of hemoglobin at 575 nm.
Immunohistochemistry
Serial cryosections (8-10 µm) were obtained from liver, spleen, small intestine, and colon for immunofluorescence staining. The antibodies used are listed in table S1. Images were captured using a confocal Laser Scanning Microscope (LSM, Zeiss) and analyzed with the Zeiss software LSM Image Browser.
RT-PCR for FIX Expression after Oral Administration of Nanoparticles
Total RNA was isolated from spleen, liver, duodenum/jejunum, ileum and colon using the High pure RNA isolation kit (Roche Diagnostics Deutschland GmbH). High capacity cDNA reverse transcriptase kit (Applied Biosystems) was used for translation of mRNA into cDNA. Quantitative real-time PCR was performed with Power SYBR Green (Applied Biosystems). Primer sequences are listed in table S2.

Statistics

Statistical evaluation of data was performed by analysis of variance (ANOVA) using SigmaPlot version 12.0 (Systat software Inc., San Jose, Calif.).

Results

To further improve the properties of the wild-type protein, the ITV and the IAV variant, the inventors introduced further mutations, single or in combination, in order to generate F.IX molecules with different properties.

Tables 5 and 6 show the tested mutations and the activity of the variants.

TABLE 5

Figures 11A, 11B, 11C:
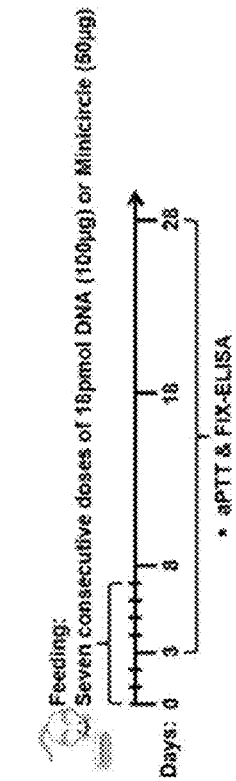
FIGS. 11A-11C Expression of functional FIX protein in small intestine after oral administration of chitosan-DNA nanoparticles.
(11A) Time schedule for feeding and blood collection.
(11B) Oral delivery of chitosan formulated pcDNA3.1 vectors containing FIX variants. Bars represent means±SEM, n=5/group.
(11C) Oral delivery of chitosan formulated minicircles containing FIX muteins with defective collagen IV binding sites.
Shown is mean±SEM, n=5-6/group. *p<0.05 according to ANOVA using Dunnett's test for multiple comparison with the chitosan/mock group.
Figure 12A:
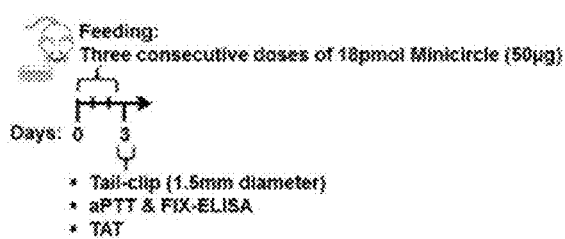
FIGS. 12A-12D Phenotype correction of HB mice after delivery chitosan formulated FIX muteins.
(12A) Time schedule.
(12B) Tail-clip experiment after tail dissection at 1.5 mm diameter after oral administration of formulated vector encoding FIX-WT (n=7), FIX-KLW (n=8) and FIX-AKLW (n=7). Control groups include wild-type mice (n=6) and naïve HB mice (n=7).
(12C) Coagulation time measured by one-stage aPTT.
(12D) TAT levels as a marker for hypercoagulopathy.
Shown are means±SEM. **p<0.01 according to ANOVA using Dunnett's test for multiple comparison with the HB group.
Figure 12B:
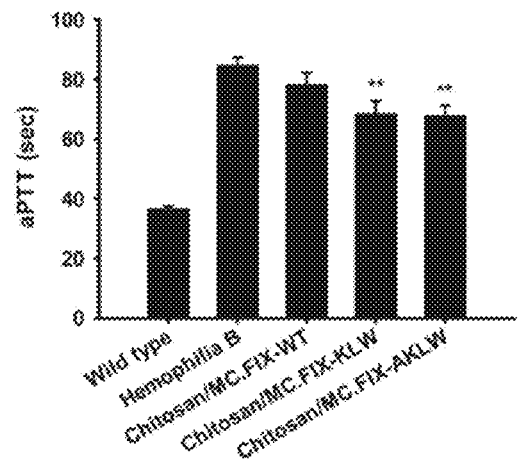
Figure 12C:
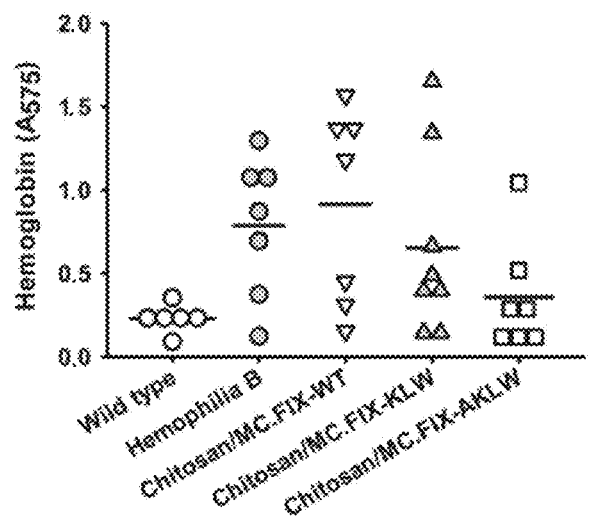
Figure 12D:
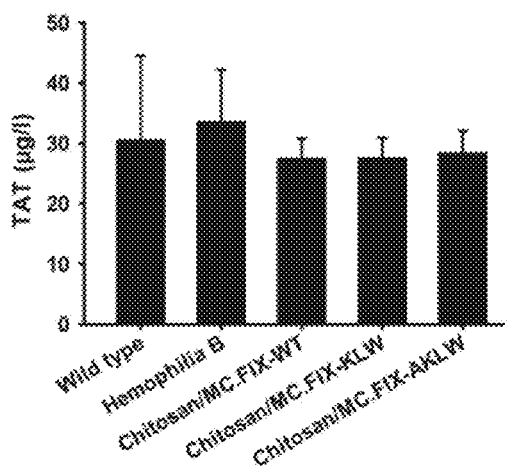

Clotting activities of factor IX variants including a single amino acid substitution introduced into the wild type F.IX expression cassette resulting in hyperfunctional variants in presence of F.VIII. Clotting activities were measured in FIX-deficient plasma by a one stage aPTT assay. Values are shown in percent, being 100% the activity of wild type factor IX in normal human pool plasma with normal human levels of F.IX. Standard error of mean (S.E.M.).

| Variants | specific FIX activity (%) | S.E.M. (%) |
|---|---|---|
| WT-FIX | 100.00 | 7.00 |
| K5F | 141.28 | 4.53 |
| L6F | 165.46 | 19.4 |
| V10F | 140.20 | 5.8 |
| V10R | 194.98 | 11.3 |
| Q11H | 285.39 | 15.02 |
| Q11K | 248.95 | 15.6 |
| Q11R | 126.45 | 26.21 |
| Q44H | 179.37 | 42.51 |
| W72R | 125.64 | 21.44 |
| F75V | 114.12 | 18.44 |
| S102N | 144.67 | 26.13 |
| N105S | 107 | 7 |
| K122R | 178 | 43 |
| E185D | 139.28 | 21.02 |
| E224G | 148.48 | 31.47 |
| E243D | 119 | 0.1 |
| I263S | 177.91 | 19.8 |
| R338E | 451.7 | 27.35 |
| T376A | 258.38 | 65.68 |

TABLE 6

Clotting activities of factor IX variants including multiple amino acid substitutions resulting in hyperfunctional variants in presence of F.VIII measured by a one stage aPTT assay. Values are shown in percent, being 100% the activity of wild type factor IX in normal human pool plasma with normal human levels of F.IX. Standard error of mean (S.E.M.).

| Variants | specific FIX activity (%) | S.E.M. (%) |
|---|---|---|
| WT-FIX | 100.00 | 4.00 |
| V10K | 170 | 8 |
| R338L | 735 | 36 |
| K5A + R338L | 491 | 36 |
| V10K + R338L | 607 | 22 |
| R338L + S377W | 1231 | 39 |
| K5A + R338L + S377W (ALW) | 881 | 33 |
| V10K + R338L + S377W (KLW) | 1920 | 97 |
| K5A + V10K + R338L + S377W (AKLW) | 1139 | 82 |
| KLW + L6F | 2212 | 448 |
| KLW + E243D | 2140 | 383 |
| KLW + E224G | 2021 | 451 |

TABLE 6-continued

Clotting activities of factor IX variants including multiple amino acid substitutions resulting in hyperfunctional variants in presence of F.VIII measured by a one stage aPTT assay. Values are shown in percent, being 100% the activity of wild type factor IX in normal human pool plasma with normal human levels of F.IX. Standard error of mean (S.E.M.).

| Variants | specific FIX activity (%) | S.E.M. (%) |
|---|---|---|
| KLW + L6F + E224G | 2008 | 400 |
| KLW + E224G + E243D | 2049 | 371 |
| KLW + K265T | 3396 | 151 |
| G4Y + V86A + R338L + S377W (YALW) | 1535 | 130 |
| YALW + K265T | 1581 | 136 |

Hepatic Expression of FIX Mutants Effectively Triggers Hemostasis

To examine the expression and clotting activity of FIX mutants in vivo, we hydrodynamically injected liver-directed minicircles encoding either FIX-KLW, -AKLW, -YALW or FIX-WT at vector doses of 10 μg into the tail vein of HB mice. Three days after gene delivery, FIX expression levels reached around 100% of normal plasma levels in all treated groups (data not shown). As expected, given the selection of hyperfunctional FIX mutants, the clotting activities of all three mutants were significantly higher up to 10-fold than that of FIX-WT (FIG. 8C). The ratio of activity and antigen revealed a 10- to 17-fold increase in specific FIX activity ($p<0.05$). Moreover, tail-cut bleeding assay revealed a complete normalization of the bleeding phenotype comparable to that of hemostatically normal mice (FIG. 8D).

Oral Gene Delivery

Oral Administration of Chitosan-DNA Nanoparticles Results in Production of FIX Protein in Small Intestines of HB Mice First, characterization of nanoparticle stability and transfection efficiency was performed in series of in vitro experiments (data not shown). Next, nanoparticles were administered orally (FIG. 10A). In vivo, GFP expression was successfully stained in small intestine after oral administration of a single dose of chitosan formulated eGFP to HB mice (FIG. 10B). No signal was detected in liver, spleen or colon (data not shown) and after administration of unformulated vector, as expected. Oral delivery of chitosan formulated FIX-WT revealed FIX presentation primarily located in microvilli around endothelial cells and partially in the extracellular matrix (ECM) (FIG. 10C, row 1). However, there was also a co-localization of FIX protein and collagen IV, a natural ligand for FIX, so that we hypothesized that collagen IV might interfere with release of FIX protein into the circulation (FIG. 10C, row 3). To overcome this obstacle, the FIX variants KLW or AKLW, both associated with reduced collagen IV affinity, were administered to HB mice. An overall similar expression pattern was observed, although extracellular collagen IV binding of FIX variants in the gut seemed slightly decreased (FIG. 10C, row 4-5). FIX mRNA expression was detected exclusively in the entire small intestine confirming the result obtained by immunohistochemical staining and indicating a preference for nanoparticle uptake in this area. Application of naked DNA and nanoparticles containing mock plasmid resulted in undetectable expression levels (FIG. 10D).

Repeated Oral Administration of Human FIX Mutants Provides Hemostasis in HB Mice HB mice received seven consecutive daily doses of hyperfunctional FIX variants mediated by chitosan formulated plasmid or MC vectors, as indicated in the experimental design schedule (FIG. 11A). FIX antigen expression remained below the detection limit of 1% (data not shown). However, FIX activities of mutants with impaired collagen IV binding (FIX-KLW and -AKLW vs. FIX-YALW) seemed to accumulate between day 3 and 8 and reached levels in the range up to 3% in plasmid treated (FIG. 11B) or 14% in MC treated group (FIG. 11C) on day 8 (longest time point of treatment). After discontinuation of the oral gene therapy, clotting activities of FIX mutants persisted for at least 3 weeks, albeit with significant variation which was not related to antibody formation (data not shown). By comparison, after oral delivery of chitosan formulated FIX-WT or mock clotting activity remained below the limit of detection (1%) (FIG. 11B+C). We further investigated in vivo efficacy in a tail-clip bleeding assay (FIG. 12A). The mice had significantly shorter in vitro clotting times after oral administration of FIX mutants measured by one-stage aPTT (FIG. 12B). In agreement with that observation, FIX-KLW and -AKLW expression partially corrected the bleeding phenotype of HB mice (FIG. 12C). TAT complex levels, which represent a general activation marker of the coagulation system and would, in the context of substitution therapy for hemophilia, indicate hyperfunctional or spontaneous coagulation, remained similar in all groups (FIG. 12D).

Here, we demonstrate the efficacy of oral gene delivery of FIX mutants based on the biopolymer chitosan for the treatment of HB. By combining oral gene delivery and hyperfunctional mutants, functional FIX levels can be achieved. Sensitization of mice to and hence, neutralizing Abs against human FIX were not observed with the regimens used. While the general principle of oral gene therapy has previously been described (e.g. Bowman et al., 2008), including for hemophilia A (HA), the significant progress marked by our present studies lies in the combination of function-optimized FIX and improved delivery system with this approach, as a result of which clinically relevant quantities of therapeutic protein are released. Therefore, the data provided not only reflect confirmatory proof-of-principle data but show the possibility of clinical beneficence of nanoparticle-based oral gene therapy.

The features disclosed in the foregoing description, in the claims and/or in the accompanying drawings may, both separately and in any combination thereof, be material for realizing the invention in diverse forms thereof.

REFERENCES

Arruda et al. *Blood* 2004, 104:85.
Bowman K, Leong K W. Chitosan nanoparticles for oral drug and gene delivery. *Int J Nanomedicine.* 2006; 1(2): 117-28.
Bowman K, Sarkar R, Raut S, Leong K W. Gene transfer to hemophilia A mice via oral delivery of FVIII-chitosan nanoparticles. *J Control Release.* 2008 Dec. 18; 132(3): 252-9.
Chang J, Jin J, Lollar P, Bode W, Brandstetter H, Hamaguchi N, Straight D L, Stafford D W. Changing residue 338 in human factor IX from arginine to alanine causes an increase in catalytic activity. *J Biol Chem.* 1998 May 15; 273(20):12089-94.
Chang Y J, Wu H L, Hamaguchi N, Hsu Y C, Lin S W. Identification of functionally important residues of the epidermal growth factor-2 domain of factor IX by alanine-scanning mutagenesis. Residues Asn(89)-Gly(93) are critical for binding factor VIIIa. *J Biol Chem.* 2002 Jul. 12; 277(28):25393-9.
Davie, E. W., Fujikawa, K., and Kisiel, W. (1991) *Biochemistry* 30, 10363-10370.
DiScipio, R. G., Hermodson, M. A., Yates, S. G., and Davie, E. W. (1977) *Biochemistry* 16, 698-706.
Di Scipio R G, Kurachi K and Davie E W (1978) Activation of human factor IX (Christmas factor). *J Clin Invest,* 61, 1528-1538.
Duffy E J and Lollar P (1992) Intrinsic pathway activation of factor X and its activation peptide-deficient derivative, factor Xdes-143-191. *J Biol Chem,* 267, 7821-7827.
Freedman S J, Blostein M D, Baleja J D, Jacobs M, Furie B C, Furie B. Identification of the phospholipid binding site in the vitamin K-dependent blood coagulation protein factor IX. *J Biol Chem.* 1996 Jul. 5; 271(27):16227-36.
Fujikawa, K., Legaz, M. E., Kato, H., and Davie, E. W. (1974) *Biochemistry* 13, 4508-4516.
Furie B and Furie B C (1988) The molecular basis of blood coagulation. *Cell,* 53, 505-518.
Giannelli, F., Green, P. M., Sommer, S. S., Poon, M., Ludwig, M., Schwaab, R., Reitsma, P. H., Goossens, M., Yoshioka, A., Figueiredo, M. S., and Brownlee, G. G. (1998) *Nucleic Acids Res.* 26, 265-268.
Hartmann R, Dockal M, Kammlander W, Panholzer E, Nicolaes G A, Fiedler C, Rosing J and Scheiflinger F. Factor IX mutants with enhanced catalytic activity. *J Thromb Haemost* 2009; 7: 1656-62.
Hopfner K P, Brandstetter H, Karcher A, Kopetzki E, Huber R, Engh R A, Bode W. (1997) *EMBO J.* 16(22):6626-35.
Kao C Y, Yang S J, Tao M H, Jeng Y M, Yu I S, Lin S W. Incorporation of the factor IX Padua mutation into FIX-Triple improves clotting activity in vitro and in vivo. *Thromb Haemost.* 2013 Jul. 29; 110(2):244-56.
Kurachi and Davie (1982) *PNAS* 79:6461-6464.
Langdell R D, Wagner R H, Brinkhous K M (1953). "Effect of antihemophilic factor on one-stage clotting tests; a presumptive test for hemophilia and a simple one-stage antihemophilic factor assay procedure". *J. Lab. Clin. Med.* 41 (4): 637-47.
Lindquist, P. A., Fujikawa, K., and Davie, E. W. (1978) *J. Biol. Chem.* 253, 1902-1909.
Mann et al. *Arterioscler Thromb Vasc Biol.* 2003; 23:17-25.
Mao H Q, Roy K, Troung-Le V L, Janes K A, Lin K Y, Wang Y, et al. Chitosan-DNA nanoparticles as gene carriers: synthesis, characterization and transfection efficiency. *J Control Release.* 2001 Feb. 23; 70(3):399-421.
McRae B J, Kurachi K, Heimark R L, Fujikawa K, Davie E W and Powers J C (1981) Mapping the active sites of bovine thrombin, factor IXa, factor Xa, factor XIa, factor XIIa, plasma kallikrein, and trypsin with amino acid and peptide thioesters: development of new sensitive substrates. *Biochemistry,* 20, 7196-7206.
Milanov P, Ivanciu L, Abriss D, Quade-Lyssy P, Miesbach W, Alesci S, Toon T, Grez M, Seifried E and Schüttrumpf J. Engineered factor IX variants bypass FVIII and correct haemophilia A phenotype in mice. *Blood* 2012 Jan. 12; 119(2):602-11.
Quade-Lyssy P, Milanov P, Schuettrumpf J (2012) Engineered Factor VII, Factor IX, and Factor X Variants for Hemophilia Gene Therapy. *J Genet Syndr Gene Ther* 2012, S1:013. doi:10.4172/2157-7412.S1-013.
Schuettrumpf J, Herzog R W, Schlachterman A, Kaufhold A, Stafford D W, Arruda V R. (2005) *Blood.* 105(6):2316-23.
Schuettrumpf J, Milanov P, Roth S, Seifried E, Tonn T. Non-viral gene transfer results in therapeutic factor IX levels in haemophilia B mice, *Haemost.* 2008; 1:S92-95.
Sichler K, Kopetzki E, Huber R, Bode W, Hopfner K P, Brandstetter H. Physiological fIXa activation involves a cooperative conformational rearrangement of the 99-loop. (2003) *J Biol Chem.* 278(6):4121-6.

Wilkinson F H, London F S, Walsh P N. Residues 88-109 of factor IXa are important for assembly of the factor X activating complex. *J Biol Chem*. 2002 Feb. 22; 277(8): 5725-33.

Wilkinson F H, Ahmad S S, Walsh P N. The factor IXa second epidermal growth factor (EGF2) domain mediates platelet binding and assembly of the factor X activating complex. J Biol Chem. 2002 Feb. 22; 277(8):5734-41.

The invention claimed is:

1. A nucleic acid encoding a variant of factor IX (F.IX) or variant of activated factor IX (F.IXa), wherein the F.IX comprises SEQ ID NO: 2, and wherein the variant F.IX or variant F.IXa comprises the amino acid substitution of L6F of SEQ ID NO: 2, and optionally further comprises the amino acid substitutions V181I, K265A, and I383V of SEQ ID NO: 2.

2. A pharmaceutical composition comprising the nucleic acid of claim 1 and optionally pharmaceutically acceptable carrier(s) and/or excipient(s).

3. A method for treating or preventing a disease in a subject, wherein the disease is bleeding or a bleeding disorder, said method comprising administering to the subject the nucleic acid of claim 1.

4. The method of claim 3, comprising administering the nucleic acid to the subject via cellular therapy, gene therapy or gene delivery.

5. The method of claim 4,
wherein the gene therapy or gene delivery comprises administering the nucleic acid in a viral vector construct or a non-viral vector construct.

6. The method of claim 5, wherein the viral vector construct or the non-viral vector construct is formulated in chitosan nanoparticles.

7. The nucleic acid encoding of claim 1, wherein the variant F.IX or variant F.IXa comprises the amino acid substitution of L6F, V181I, K265A, and I383V of SEQ ID NO: 2.

* * * * *

SEQUENCE LISTING

<160> NUMBER OF SEQ ID NOS: 4

<210> SEQ ID NO 1
<211> LENGTH: 1386
<212> TYPE: DNA
<213> ORGANISM: Homo sapiens

<400> SEQUENCE: 1

```
atgcagcgcg tgaacatgat catggcagaa tcaccaggcc tcatcaccat ctgcctttta      60
ggatatctac tcagtgctga atgtacagtt tttcttgatc atgaaaacgc caacaaaatt     120
ctgaatcggc caaagaggta taattcaggt aaattggaag agtttgttca agggaacctt     180
gagagagaat gtatggaaga aaagtgtagt tttgaagaag cacgagaagt ttttgaaaac     240
actgaaagaa caactgaatt ttggaagcag tatgttgatg gagatcagtg tgagtccaat     300
ccatgtttaa atggcggcag ttgcaaggat gacattaatt cctatgaatg ttggtgtccc     360
tttggatttg aaggaaagaa ctgtgaatta gatgtaacat gtaacattaa gaatggcaga     420
tgcgagcagt tttgtaaaaa tagtgctgat aacaaggtgg tttgctcctg tactgaggga     480
tatcgacttg cagaaaacca gaagtcctgt gaaccagcag tgccatttcc atgtggaaga     540
gtttctgttt cacaaacttc taagctcacc cgtgctgaga ctgttttttcc tgatgtggac     600 tatgtaaatt ctactgaagc tgaaaccatt ttggataaca tcactcaaag cacccaatca     660
tttaatgact tcacgcgtgt tgttggtgga gaagatgcca aaccaggtca attcccttgg     720
caggttgttt tgaatggtaa agttgatgca ttctgtggag gctctatcgt taatgaaaaa     780
tggattgtaa ctgctgccca ctgtgttgaa actggtgtta aaattacagt tgtcgccggc     840
gaacataata ttgaggagac agaacataca gagcaaaagc gaaatgtgat tcgaattatt     900
cctcaccaca actacaatgc agctattaat aagtacaacc atgacattgc ccttctggaa     960
ctggacgaac ccttagtgct aaacagctac gttacaccta tttgcattgc tgacaaggaa    1020
tacacgaaca tcttcctcaa atttggatct ggctatgtaa gtggctgggg aagagtcttc    1080
cacaaaggga gatcagcttt agttcttcag taccttagag ttccacttgt tgaccgagcc    1140
acatgtcttc gatctacaaa gttcaccatc tataacaaca tgttctgtgc tggcttccat    1200
gaaggaggta gagattcatg tcaaggagat agtgggggac ccatgttact gaagtggaa    1260 gggaccagtt tcttaactgg aattattagc tggggtgaag agtgtgcaat gaaaggcaaa    1320
tatggaatat ataccaaggt atcccggtat gtcaactgga ttaaggaaaa aacaaagctc    1380
acttaa                                                              1386
```

<210> SEQ ID NO 2
<211> LENGTH: 461
<212> TYPE: PRT
<213> ORGANISM: Homo sapiens

<400> SEQUENCE: 2

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30
```

```
Asp His Glu Asn Ala Asn Lys Ile Leu Asn Arg Pro Lys Arg Tyr Asn
             35                  40                  45

Ser Gly Lys Leu Glu Glu Phe Val Gln Gly Asn Leu Glu Arg Glu Cys
 50                  55                  60

Met Glu Glu Lys Cys Ser Phe Glu Glu Ala Arg Glu Val Phe Glu Asn
 65                  70                  75                  80

Thr Glu Arg Thr Thr Glu Phe Trp Lys Gln Tyr Val Asp Gly Asp Gln
                 85                  90                  95

Cys Glu Ser Asn Pro Cys Leu Asn Gly Gly Ser Cys Lys Asp Asp Ile
                100                 105                 110

Asn Ser Tyr Glu Cys Trp Cys Pro Phe Gly Phe Glu Gly Lys Asn Cys
                115                 120                 125

Glu Leu Asp Val Thr Cys Asn Ile Lys Asn Gly Arg Cys Glu Gln Phe
            130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
                180                 185                 190

Glu Thr Val Phe Pro Asp Val Asp Tyr Val Asn Ser Thr Glu Ala Glu
            195                 200                 205

Thr Ile Leu Asp Asn Ile Thr Gln Ser Thr Gln Ser Phe Asn Asp Phe
            210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
                260                 265                 270

Val Lys Ile Thr Val Val Ala Gly Glu His Asn Ile Glu Glu Thr Glu
            275                 280                 285

His Thr Glu Gln Lys Arg Asn Val Ile Arg Ile Ile Pro His His Asn
            290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
                340                 345                 350

Val Ser Gly Trp Gly Arg Val Phe His Lys Gly Arg Ser Ala Leu Val
            355                 360                 365

Leu Gln Tyr Leu Arg Val Pro Leu Val Asp Arg Ala Thr Cys Leu Arg
            370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430
```

```
Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr
    450                 455                 460

<210> SEQ ID NO 3
<211> LENGTH: 19
<212> TYPE: DNA
<213> ORGANISM: Artificial Sequence
<220> FEATURE:
<223> OTHER INFORMATION: Forward primer

<400> SEQUENCE: 3
tctgaatcgg ccaaagagg                                            19

<210> SEQ ID NO 4
<211> LENGTH: 21
<212> TYPE: DNA
<213> ORGANISM: Artificial Sequence
<220> FEATURE:
<223> OTHER INFORMATION: Reverse primer

<400> SEQUENCE: 4
cagttgacat accgggatac c                                         21
```